US008350034B2

(12) United States Patent
Griesgraber et al.

(10) Patent No.: US 8,350,034 B2
(45) Date of Patent: *Jan. 8, 2013

(54) SUBSTITUTED CHIRAL FUSED [1,2]IMIDAZO[4,5-C] RING COMPOUNDS

(75) Inventors: George W. Griesgraber, Eagan, MN (US); Tushar A. Kshirsagar, Woodbury, MN (US); Sarah J. Slania, Eagan, MN (US); Michael E. Danielson, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/196,131

(22) Filed: Aug. 2, 2011

(65) Prior Publication Data

US 2011/0293654 A1 Dec. 1, 2011

Related U.S. Application Data

(63) Continuation of application No. 11/813,052, filed as application No. PCT/US2005/047297 on Dec. 29, 2005, now Pat. No. 8,034,938.

(60) Provisional application No. 60/640,440, filed on Dec. 30, 2004, provisional application No. 60/697,256, filed on Jul. 7, 2005.

(51) Int. Cl.
*C07D 401/04* (2006.01)
*A61K 31/438* (2006.01)

(52) U.S. Cl. .......................................... 546/18; 514/278
(58) Field of Classification Search .................... 546/80; 514/290
See application file for complete search history.

(56) References Cited

U.S. PATENT DOCUMENTS

| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A * | 1/1996 | Lindstrom ..................... 514/183 |
| 5,494,916 A | 2/1996 | Lindstrom et al. |
| 5,525,612 A | 6/1996 | Gerster |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,756,747 A | 5/1998 | Gerster et al. |
| 5,886,006 A | 3/1999 | Nikolaides et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |
| 6,440,992 B1 | 8/2002 | Gerster et al. |
| 6,451,810 B1 | 9/2002 | Coleman et al. |
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |

(Continued)

FOREIGN PATENT DOCUMENTS

EP 0 394 026 10/1990

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102. pp. 511-513, Dec. 12, 1983. Brennan et al., "Automated Bioassay of Interferons in Micro-test Plates.", *Biotechniques*, Jun./Jul. 78, 1983.
Testerman et al., "Cytokine Induction by the Immunomodulators Imiquimod and S-27609.", *Journal of Leukocyte Biology*, vol. 58, pp. 365-372, Sep. 1995.
Bachman et al., "Synthesis of Substituted Quinolylamines. Derivatives of 4-Amino-7-Chloroquinoline.", *J. Org. Chem.* 15, pp. 1278-1284 (1950).
Jain et al., "Chemical and Pharmacological Investigations of Some ω-Substituted Alkylamino-3-aminopyridines.", *J. Med. Chem.*, 11, pp. 87-92 (1968).
Baranov et al., "Pyrazoles, Imidazoles, and Other 5-Membered Rings.", *Chem. Abs.* 85, 94362, (1976).
Berényi et al., "Ring Transformation of Condensed Dihydro-astriazines.", *J. Heterocyclic Chem.*, 18, pp. 1537-1540 (1981).

(Continued)

*Primary Examiner* — Rita Desai

(57) ABSTRACT

Substituted fused [1,2]imidazo[4,5-c] ring compounds (e.g., imidazo[4,5-c]quinolines, 6,7,8,9-tetrahydroimidazo[4,5-c] quinolines, imidazo[4,5-c]naphthyridines, and 6,7,8,9-tetrahydroimidazo[4,5-c]naphthyridines) with a —CH($R_1$)— group in the fused ring at the 1-position of the imidazo ring, wherein $R_1$ includes a functional group, for example, an amide, sulfonamide, urea, carbamate, ester, ketone, ether, a thio analog of the forgoing, sulfone, oxime, or hydroxylamine, pharmaceutical compositions containing the compounds, intermediates, methods of making the compounds, and methods of use of these compounds as immunomodulators, for inducing cytokine biosynthesis in animals and in the treatment of diseases including viral and neoplastic diseases, are disclosed.

15 Claims, No Drawings

U.S. PATENT DOCUMENTS

| | | |
|---|---|---|
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,225 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stoermer et al. |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 7,906,506 B2 * | 3/2011 | Griesgraber et al. ...... 514/229.5 |
| 7,943,609 B2 * | 5/2011 | Griesgraber et al. ...... 514/229.5 |
| 7,968,562 B2 | 6/2011 | Skwierczynski et al. |
| 7,968,563 B2 | 6/2011 | Kshirsagar et al. |
| 7,993,659 B2 | 8/2011 | Noelle et al. |
| 8,017,779 B2 | 9/2011 | Merrill et al. |
| 8,026,366 B2 | 9/2011 | Prince et al. |
| 8,034,938 B2 * | 10/2011 | Griesgraber et al. ........... 546/64 |
| 8,093,390 B2 * | 1/2012 | Rice et al. ...................... 546/64 |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0133913 A1 | 7/2003 | Tomai et al. |
| 2003/0139364 A1 | 7/2003 | Krieg et al. |
| 2004/0014779 A1 | 1/2004 | Gorden et al. |
| 2004/0132079 A1 | 7/2004 | Gupta et al. |
| 2004/0175336 A1 | 9/2004 | Egging et al. |
| 2004/0180919 A1 | 9/2004 | Lee et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0048072 A1 | 3/2005 | Kedl et al. |
| 2005/0059072 A1 | 3/2005 | Birmachu et al. |
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0239735 A1 | 10/2005 | Miller et al. |
| 2005/0245562 A1 | 11/2005 | Garcia-Echeverria et al. |
| 2006/0045885 A1 | 3/2006 | Kedl et al. |
| 2006/0045886 A1 | 3/2006 | Kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0155767 A1 | 7/2007 | Radmer et al. |
| 2007/0166384 A1 | 7/2007 | Zarraga et al. |

| | | | |
|---|---|---|---|
| 2007/0167479 A1 | 7/2007 | Busch et al. |
| 2007/0213355 A1 | 9/2007 | Capraro et al. |
| 2007/0219196 A1 | 9/2007 | Krepski et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0287725 A1 | 12/2007 | Moser et al. |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0070907 A1 | 3/2008 | Griesgraber et al. |
| 2008/0085895 A1 | 4/2008 | Griesgraber et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0269192 A1 | 10/2008 | Griesgraber et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |
| 2011/0021554 A1 | 1/2011 | Stoesz et al. |

FOREIGN PATENT DOCUMENTS

| | | |
|---|---|---|
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 2005/003064 | 1/2005 |
| WO | WO 2006/028451 | 3/2006 |
| WO | WO 2006/063072 | 6/2006 |
| WO | WO 2006/121528 | 11/2006 |
| WO | WO 2007/030775 | 3/2007 |

OTHER PUBLICATIONS

Chollet et al., "Development of a Topically Active Imiquimod Formulation.", *Pharmaceutical Development and Technology*, 4(1), pp. 35-43 (1999).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

\* cited by examiner

SUBSTITUTED CHIRAL FUSED [1,2]IMIDAZO[4,5-C] RING COMPOUNDS

CROSS REFERENCE TO RELATED APPLICATIONS

This application is a continuation of U.S. application Ser. No. 11/813,052, filed Jun. 28, 2007, now U.S. Pat. No. 8,034,938; which is the National Stage Filing of International Application No. PCT/US2005/047297, filed Dec. 29, 2005, which claims priority to U.S. Provisional Application No. 60/640,440, filed Dec. 30, 2004, and U.S. Provisional Application No. 60/697,256, filed Jul. 7, 2005, all of which are incorporated herein by reference.

BACKGROUND

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

There continues to be interest in and a need for compounds that have the ability to modulate the immune response, by induction of cytokine biosynthesis or other mechanisms.

SUMMARY

The present invention provides a new class of compounds that are useful in modulating cytokine biosynthesis in animals. Such compounds are of the following Formula I:

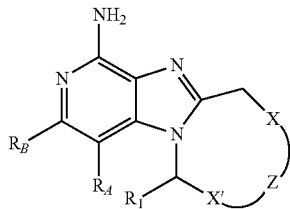

and, more particularly, compounds of the following Formulas II, IIa, II-1, and II-1a:

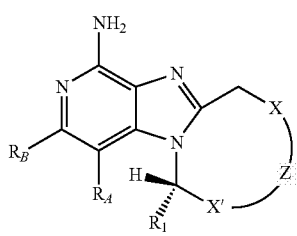

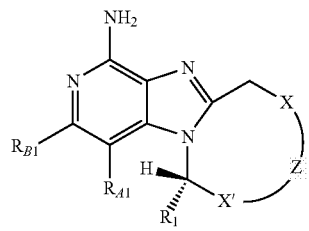

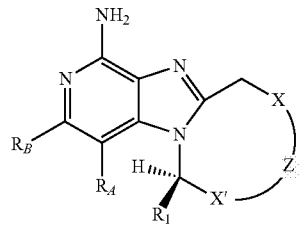

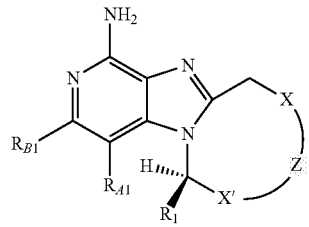

wherein: X, X', Z, $R_1$, $R_A$, $R_B$, $R_{A1}$, and $R_{B1}$ are as defined below.

The compounds of Formulas I, II, IIa, II-1, and II-1a are useful, for example, as immune response modifiers (IRMs) due to their ability to modulate cytokine biosynthesis (e.g., induce or inhibit the biosynthesis or production of one or more cytokines) and otherwise modulate the immune response when administered to animals. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

The invention further provides pharmaceutical compositions containing an effective amount of a compound of Formulas I, II, IIa, II-1, or II-1a and methods of inducing cytokine biosynthesis in an animal, treating a viral infection and/or treating a neoplastic disease in an animal by administering an effective amount of a compound of Formula II or Formula IIa to the animal.

In addition, methods of synthesizing compounds of Formulas I, II, IIa, II-1, and II-1a and intermediates useful in the synthesis of these compounds are provided.

As used herein, "a" "an" "the" "at least one", and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.
DETAILED DESCRIPTION OF ILLUSTRATIVE EMBODIMENTS OF THE INVENTION
The present invention provides compounds of the following Formulas I, II, II-1, IIa, II-1a, III, III-1, IV, IV-1, V, V-1, VI, VI-1, VII, and VII-1:
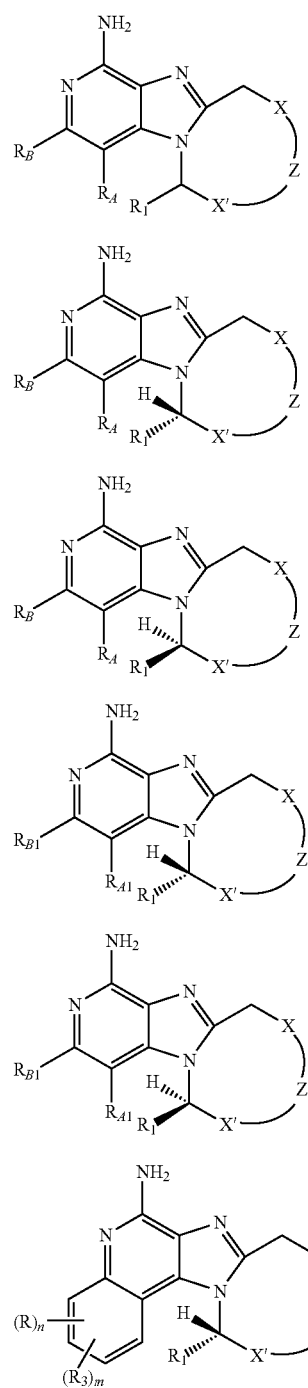
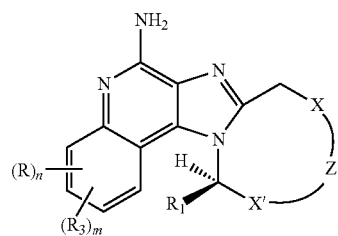
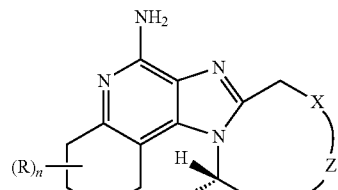
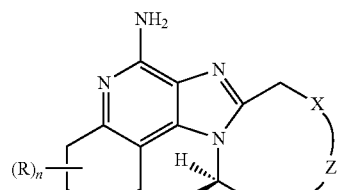
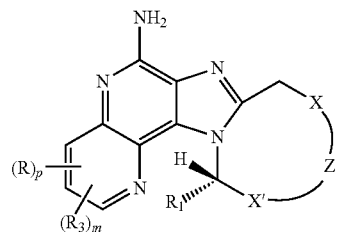
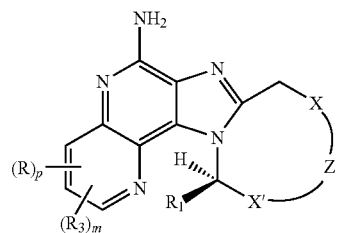
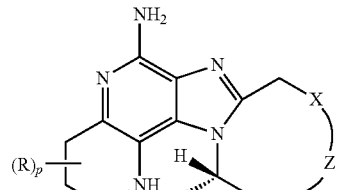

-continued

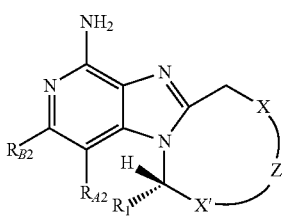

VII

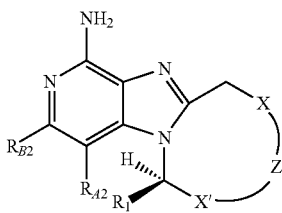

VII-1 as well as intermediates of the following Formulas X and X-1:

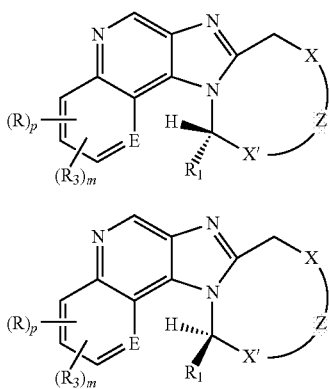

X

X-1 wherein: X, X', Z, R, $R_1$, $R_3$, $R_A$, $R_B$, $R_{A1}$, $R_{B1}$, $R_{A2}$, $R_{B2}$, E, m, n, and p are as defined below.

In one embodiment, the present invention provides a compound of Formula I:

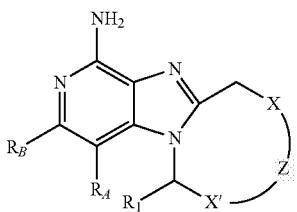

I wherein:

X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—$R_2$)—;

$R_1$ is selected from the group consisting of:
—$X_1$—Y'—$R_4$,
—$X_1$—Y'—X"—Y'—$R_4$, and
—$X_1$—$R_5$;

$R_A$ and $R_B$ are each independently selected from the group consisting of:
hydrogen,
halogen,
alkyl,
alkenyl,
alkoxy,
alkylthio, and
—N($R_9$)$_2$;

or when taken together, $R_A$ and $R_B$ form a fused aryl ring or heteroaryl ring containing one heteroatom selected from the group consisting of N and S, wherein the fused aryl or heteroaryl ring is unsubstituted or substituted by one or more W groups;

or when taken together, $R_A$ and $R_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—N($R_9$)$_2$;

R' is a non-interfering substituent;

$X_1$ is selected from the group consisting of alkylene and alkenylene, wherein the alkylene and alkenylene are optionally interrupted by one or more —O— groups, and optionally substituted by a hydroxy or methoxy group;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
a bond,
—S(O)$_2$—,
—S(O)$_2$—N($R_8$)—,
—C($R_6$)—,
—C($R_6$)—N($R_8$)—,
—C($R_6$)—N($R_8$)—C($R_6$)—,
—C($R_6$)—N($R_8$)—S(O)$_2$—, and
—C($R_6$)—O—;

Y' is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,

—C(=N—O—R$_8$)—,
—CH(—N(—O—R$_8$)-Q-R$_4$)—,

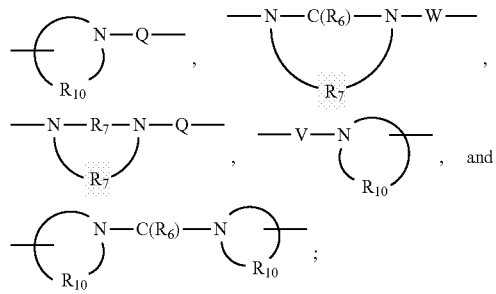

R$_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

R$_5$ is selected from the group consisting of:

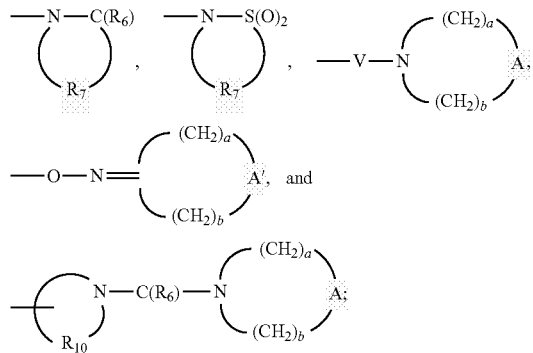

R$_6$ is selected from the group consisting of =O and =S;
R$_7$ is C$_{2-7}$ alkylene;

R$_8$ is selected from the group consisting of hydrogen, C$_{1-10}$alkyl, C$_{2-10}$alkenyl, hydroxy-C$_{1-10}$alkylenyl, C$_{1-10}$alkoxy-C$_{1-10}$alkylenyl, aryl-C$_{1-10}$alkylenyl, and heteroaryl-C$_{1-10}$alkylenyl;

R$_9$ is selected from the group consisting of hydrogen and alkyl;

R$_{10}$ is C$_{3-8}$ alkylene;

A is selected from the group consisting of —CH$_2$—, —O—, —C(O)—, —S(O)$_{0-2}$—, and —N(-Q-R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

with the proviso that X$_1$ can also be a bond when:
Y' is bonded to X$_1$ and Y' is —C(R$_6$)—, —C(R$_6$)—O—, —C(R$_6$)—N(R$_8$)—, —C(R$_6$)—N(OR$_9$)—, —C(=N—O—R$_8$)—, —CH(—N(—O—R$_8$)-Q-R$_4$)—,

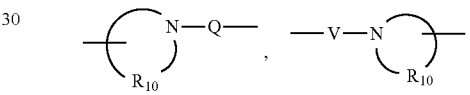

wherein V is —C(R$_6$)—, or

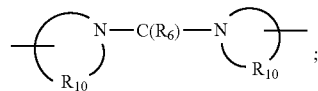

or
R$_5$ is bonded to X$_1$ and R$_5$ is

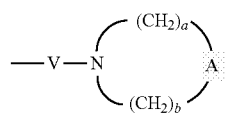

wherein V is —C(R$_6$)— or

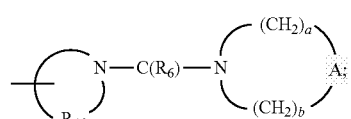

or a pharmaceutically acceptable salt thereof.

In another embodiment of Formula I, X$_1$ is selected from the group consisting of alkylene and alkenylene, wherein the alkylene and alkenylene are optionally interrupted by one or more —O— groups.

In one preferred embodiment, the present invention provides a compound of Formula II:

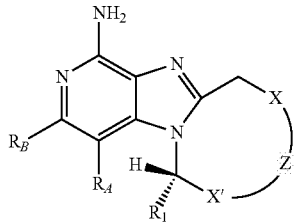

wherein:

X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—R$_2$)—;

R$_1$ is selected from the group consisting of:
—X$_1$—Y'—R$_4$,
—X$_1$—Y'—X"—Y'—R$_4$, and
—X$_1$—R$_5$;

R$_A$ and R$_B$ are each independently selected from the group consisting of:
hydrogen,
halogen,
alkyl,
alkenyl,
alkoxy,
alkylthio, and
—N(R$_9$)$_2$;

or when taken together, R$_A$ and R$_B$ form a fused aryl ring or heteroaryl ring containing one heteroatom selected from the group consisting of N and S, wherein the fused aryl or heteroaryl ring is unsubstituted or substituted by one or more W groups;

or when taken together, R$_A$ and R$_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—N(R$_9$)$_2$;

R' is a non-interfering substituent;

X$_1$ is selected from the group consisting of alkylene and alkenylene, wherein the alkylene and alkenylene are optionally interrupted by one or more —O— groups, and optionally substituted by a hydroxy or methoxy group;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
a bond,
—S(O)$_2$—,
—S(O)$_2$—N(R$_8$)—,
—C(R$_6$)—,
—C(R$_6$)—N(R$_8$)—,
—C(R$_6$)—N(R$_8$)—C(R$_6$)—,
—C(R$_6$)—N(R$_8$)—S(O)$_2$—, and
—C(R$_6$)—O—;

Y' is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

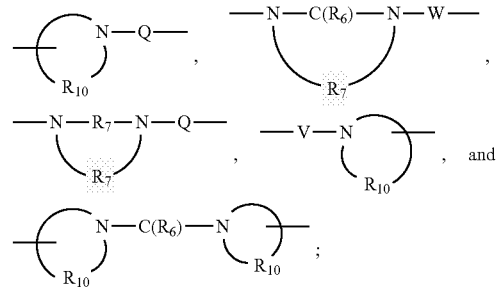

R$_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of

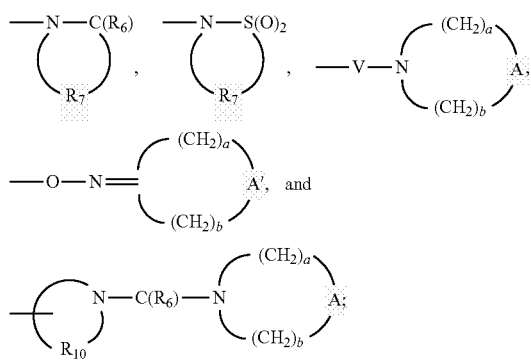

$R_6$ is selected from the group consisting of =O and =S;
$R_7$ is $C_{2-7}$ alkylene;
$R_8$ is selected from the group consisting of hydrogen, $C_{1-10}$alkyl, $C_{2-10}$alkenyl, hydroxy-$C_{1-10}$alkylenyl, $C_{1-10}$alkoxy-$C_{1-10}$alkylenyl, aryl-$C_{1-10}$alkylenyl, and heteroaryl-$C_{1-10}$alkylenyl;
$R_9$ is selected from the group consisting of hydrogen and alkyl;
$R_{10}$ is $C_{3-8}$ alkylene;
A is selected from the group consisting of —$CH_2$—, —O—, —C(O)—, —S(O)$_{0-2}$—, and —N(-Q-$R_4$)—;
A' is selected from the group consisting of —O—, —S(O)$_{0-2}$—, —N(-Q-$R_4$)—, and —$CH_2$—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≦7;

with the proviso that $X_1$ can also be a bond when:
Y' is bonded to $X_1$ and Y' is —C($R_6$)—, —C($R_6$)—O—, —C($R_6$)—N($R_8$)—, —C($R_6$)—N(O$R_9$)—, —C(=N—O—$R_8$)—, —CH(—N(—O—$R_8$)-Q-$R_4$)—,

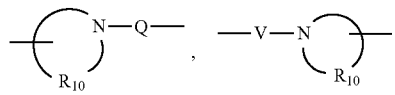

wherein V is —C($R_6$)—, or

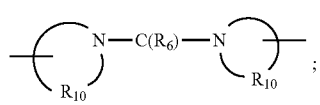

or
$R_5$ is bonded to $X_1$ and $R_5$ is

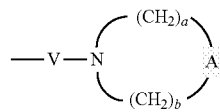

wherein V is —C($R_6$)— or

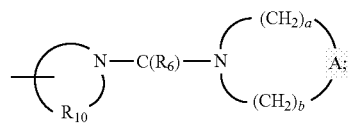

or a pharmaceutically acceptable salt thereof.

In another embodiment of Formula II, $X_1$ is selected from the group consisting of alkylene and alkenylene, wherein the alkylene and alkenylene are optionally interrupted by one or more —O— groups.

In other embodiments, the present invention provides a compound of Formula II-1:

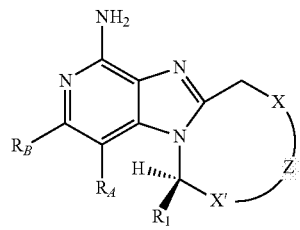

II-1 wherein X, X', Z, $R_1$, $R_A$, and $R_B$ are as defined in any one of the embodiments of Formula II above; or a pharmaceutically acceptable salt thereof.

In one preferred embodiment, the present invention provides a compound of Formula IIa:

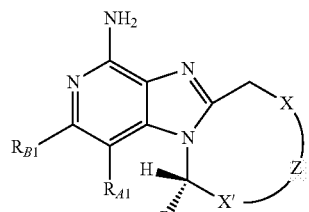

IIa wherein:
X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;
X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;
X and X' are further characterized in that the sum of the ring carbon atoms contributed by X and X' is 1, 2, or 3;

Z is selected from the group consisting of —O— and —N(—Y—R$_2$)—;

R$_1$ is selected from the group consisting of:
—X$_1$—Y'—R$_4$,
—X$_1$—Y'—X"—Y'—R$_4$, and
—X$_1$—R$_5$;

R$_{A1}$ and R$_{B1}$ are each independently selected from the group consisting of:
hydrogen,
halogen,
alkyl,
alkenyl,
alkoxy,
alkylthio, and
—N(R$_9$)$_2$;

or when taken together, R$_{A1}$ and R$_{B1}$ form a fused aryl ring or heteroaryl ring containing one heteroatom selected from the group consisting of N and S, wherein the aryl or heteroaryl ring is unsubstituted or substituted by one or more R groups, or substituted by one R$_3$ group, or substituted by one R$_3$ group and one R group;

or when taken together, R$_{A1}$ and R$_{B1}$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
alkenyl,
haloalkyl,
alkoxy,
alkylthio, and
—N(R$_9$)$_2$;

R$_3$ is selected from the group consisting of:
—Z'—R$_4$,
—Z'—X"—R$_4$,
—Z'—X"—Y'—R$_4$,
—Z'—X"—Y'—X"—Y'—R$_4$, and
—Z'—X"—R$_5$;

X$_1$ is selected from the group consisting of alkylene and alkenylene, wherein the alkylene and alkenylene are optionally interrupted by one or more —O— groups, and optionally substituted by a hydroxy or methoxy group;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
a bond,
—S(O)$_2$—,
—S(O)$_2$—N(R$_8$)—,
—C(R$_6$)—,
—C(R$_6$)—N(R$_8$)—,
—C(R$_6$)—N(R$_8$)—C(R$_6$)—,
—C(R$_6$)—N(R$_8$)—S(O)$_2$—, and
—C(R$_6$)—O—;

Y' is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

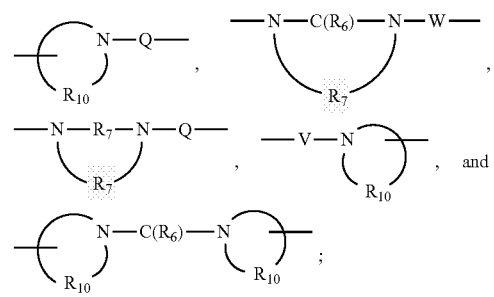

Z' is a bond or —O—;

R$_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

R$_5$ is selected from the group consisting of:

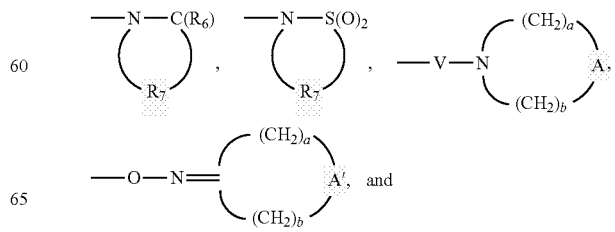

-continued

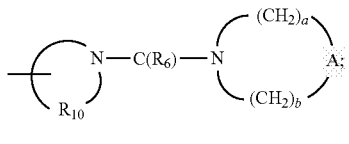

$R_6$ is selected from the group consisting of =O and =S;

$R_7$ is $C_{2-7}$ alkylene;

$R_8$ is selected from the group consisting of hydrogen, $C_{1-10}$alkyl, $C_{2-10}$alkenyl, hydroxy-$C_{1-10}$alkylenyl, $C_{1-10}$alkoxy-$C_{1-10}$alkylenyl, aryl-$C_{1-10}$alkylenyl, and heteroaryl-$C_{1-10}$alkylenyl;

$R_9$ is selected from the group consisting of hydrogen and alkyl;

$R_{10}$ is $C_{3-8}$ alkylene;

A is selected from the group consisting of —$CH_2$—, —O—, —C(O)—, —S(O)$_{0-2}$—, and —N(-Q-$R_4$)—;

A' is selected from the group consisting of —O—, —S(O)$_{0-2}$—, —N(-Q-$R_4$)—, and —$CH_2$—;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;

V is selected from the group consisting of —C($R_6$)—, —O—C($R_6$)—, —N($R_8$)—C($R_6$)—, and —S(O)$_2$—;

W is selected from the group consisting of a bond, —C(O)—, and —S(O)$_2$—; and a and b are independently integers from 1 to 6 with the proviso that a+b is ≦7;

with the proviso that $X_1$ can also be a bond when:

Y' is bonded to $X_1$ and Y' is —C($R_6$)—, —C($R_6$)—O—, —C($R_6$)—N($R_8$)—, —C($R_6$)—N(O$R_9$)—, —C(=N—O—$R_8$)—, —CH(—N(—O—$R_8$)-Q-$R_4$)—,

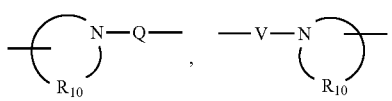

wherein V is —C($R_6$)—, or

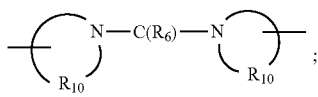

or $R_5$ is bonded to $X_1$ and $R_5$ is

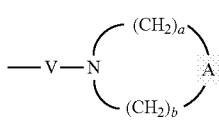

wherein V is —C($R_6$)— or

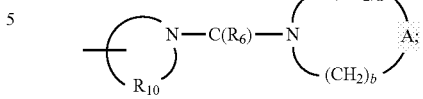

or a pharmaceutically acceptable salt thereof.

In another embodiment of Formula IIa, $X_1$ is selected from the group consisting of alkylene and alkenylene, wherein the alkylene and alkenylene are optionally interrupted by one or more —O— groups.

In other embodiments, the present invention provides a compound of Formula II-1a:

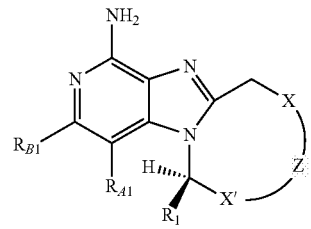

II-1a wherein X, X', Z, $R_1$, $R_{A1}$, and $R_{B1}$ are as defined in any one of the embodiments of Formula IIa above; or a pharmaceutically acceptable salt thereof.

In one preferred embodiment, there is provided a compound of Formula III:

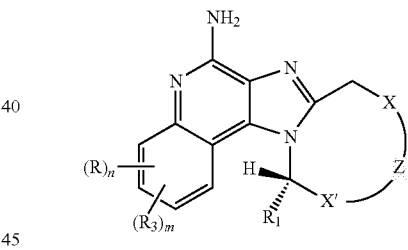

III wherein:

X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—$R_2$)—;

$R_1$ is selected from the group consisting of:
—$X_1$—Y'—$R_4$,
—$X_1$—Y'—X"—Y'—$R_4$, and
—$X_1$—$R_5$;

R is selected from the group consisting of:
halogen,
hydroxy,
alkyl,
alkenyl, haloalkyl,
alkoxy,
alkylthio, and
—N($R_9$)$_2$;
$R_3$ is selected from the group consisting of:
—Z'—$R_4$,
—Z'—X"—$R_4$,
—Z'—X"—Y'—$R_4$,
—Z'—X"—Y'—X"—Y'—$R_4$, and
—Z'—X"—$R_5$;
n is an integer from 0 to 4;
m is 0 or 1; with the proviso that when m is 1, then n is 0 or 1;
$X_1$ is selected from the group consisting of alkylene and alkenylene, wherein the alkylene and alkenylene are optionally interrupted by one or more —O— groups, and optionally substituted by a hydroxy or methoxy group;
X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
Y is selected from the group consisting of:
a bond,
—S(O)$_2$—,
—S(O)$_2$—N($R_8$)—,
—C($R_6$)—,
—C($R_6$)—N($R_8$)—,
—C($R_6$)—N($R_8$)—C($R_6$)—,
—C($R_6$)—N($R_8$)—S(O)$_2$—, and
—C($R_6$)—O—;
Y' is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N═C($R_4$)—,
—C(═N—O—$R_8$)—,
—CH(—N(—O—$R_8$)-Q-$R_4$)—,

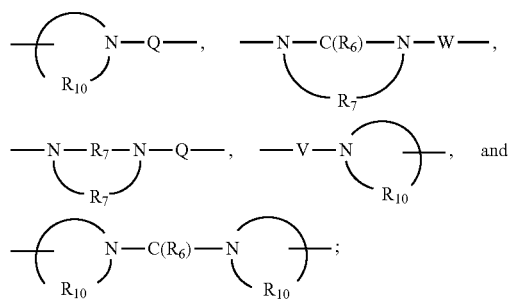

Z' is a bond or —O—;
$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;
$R_5$ is selected from the group consisting of:

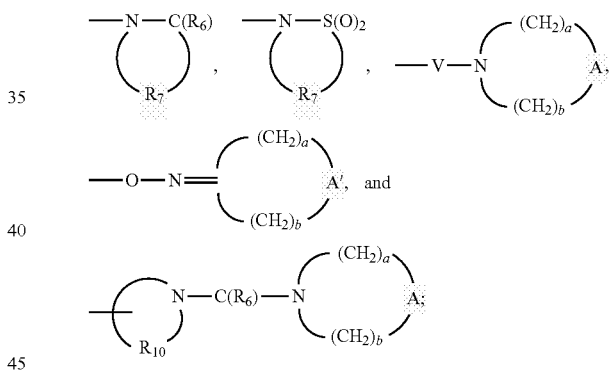

$R_6$ is selected from the group consisting of ═O and ═S;
$R_7$ is $C_{2-7}$ alkylene;
$R_8$ is selected from the group consisting of hydrogen, $C_{1-10}$alkyl, $C_{2-10}$alkenyl, hydroxy-$C_{1-10}$alkylenyl, $C_{1-10}$alkoxy-$C_{1-10}$alkylenyl, aryl-$C_{1-10}$alkylenyl, and heteroaryl-$C_{1-10}$alkylenyl;
$R_9$ is selected from the group consisting of hydrogen and alkyl;
$R_{10}$ is $C_{3-8}$ alkylene;
A is selected from the group consisting of —CH$_2$—, —O—, —C(O)—, —S(O)$_{0-2}$—, and —N(-Q-$R_4$)—;
A' is selected from the group consisting of —O—, —S(O)$_{0-2}$—, —N(-Q-$R_4$)—, and —CH$_2$—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and a and b are independently integers from 1 to 6 with the proviso that a+b is ≦7;

with the proviso that $X_1$ can also be a bond when:

Y' is bonded to $X_1$ and Y' is —C($R_6$)—, —C($R_6$)—O—, —C($R_6$)—N($R_8$)—, —C($R_6$)—N($OR_9$)—, —C(=N—O—$R_8$)—, —CH(—N(—O—$R_8$)-Q-$R_4$)—,

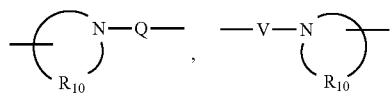

wherein V is —C($R_6$)—, or

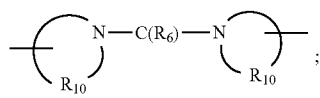

or $R_5$ is bonded to $X_1$ and $R_5$ is

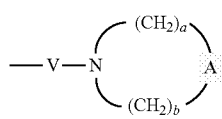

wherein V is —C($R_6$)— or

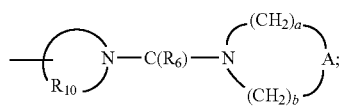

or a pharmaceutically acceptable salt thereof.

In another embodiment of Formula III, $X_1$ is selected from the group consisting of alkylene and alkenylene, wherein the alkylene and alkenylene are optionally interrupted by one or more —O— groups.

In other embodiments, there is provided a compound of Formula III-1:

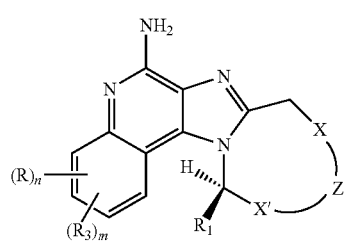

wherein X, X', Z, $R_1$, R, $R_3$, m, and n are as defined in any one of the embodiments of Formula III above; or a pharmaceutically acceptable salt thereof.

In one preferred embodiment, the present invention provides a compound of Formula IV:

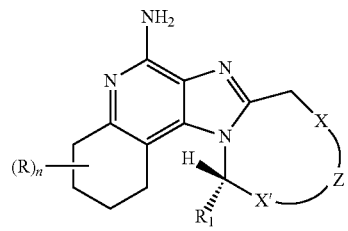

wherein:

X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—$R_2$)—;

$R_1$ is selected from the group consisting of:
  —$X_1$—Y'—$R_4$,
  —$X_1$—Y'—X"—Y'—$R_4$, and
  —$X_1$—$R_5$;

R is selected from the group consisting of:
  halogen,
  hydroxy,
  alkyl,
  alkenyl,
  haloalkyl,
  alkoxy,
  alkylthio, and
  —N($R_9$)$_2$;

n is an integer from 0 to 4;

$X_1$ is selected from the group consisting of alkylene and alkenylene, wherein the alkylene and alkenylene are optionally interrupted by one or more —O— groups, and optionally substituted by a hydroxy or methoxy group;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
  a bond,
  —S(O)$_2$—,
  —S(O)$_2$—N($R_8$)—,
  —C($R_6$)—,
  —C($R_6$)—N($R_8$)—,
  —C($R_6$)—N($R_8$)—C($R_6$)—,
  —C($R_6$)—N($R_8$)—S(O)$_2$—, and
  —C($R_6$)—O—;

Y' is selected from the group consisting of:
  —O—,
  —S(O)$_{0-2}$—,
  —S(O)$_2$—N($R_8$)—,
  —C($R_6$)—,
  —C($R_6$)—O—, —C(R$_6$)—, —O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—,
—CH(—N(—O—R$_8$)-Q-R$_4$)—,

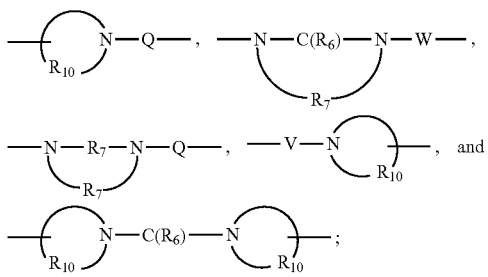

R$_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

R$_5$ is selected from the group consisting of:

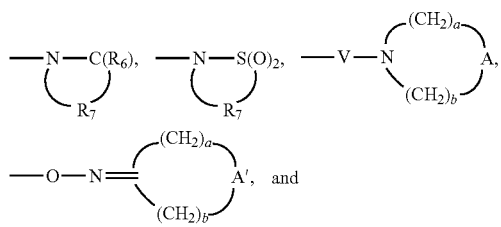

-continued

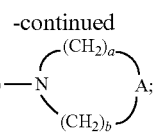

R$_6$ is selected from the group consisting of =O and =S;
R$_7$ is C$_{2-7}$ alkylene;
R$_8$ is selected from the group consisting of hydrogen, C$_{1-10}$alkyl, C$_{2-10}$alkenyl, hydroxy-C$_{1-10}$alkylenyl, C$_{1-10}$alkoxy-C$_{1-10}$alkylenyl, aryl-C$_{1-10}$alkylenyl, and heteroaryl-C$_{1-10}$alkylenyl;
R$_9$ is selected from the group consisting of hydrogen and alkyl;
R$_{10}$ is C$_{3-8}$ alkylene;
A is selected from the group consisting of —CH$_2$—, —O—, —C(O)—, —S(O)$_{0-2}$—, and —N(-Q-R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
with the proviso that X$_1$ can also be a bond when:
Y' is bonded to X$_1$ and Y' is —C(R$_6$)—, —C(R$_6$)—O—, —C(R$_6$)—N(R$_8$)—, —C(R$_6$)—N(OR$_9$)—, —C(=N—O—R$_8$)—, —CH(—N(—O—R$_8$)-Q-R$_4$)—,

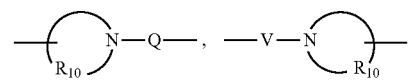

wherein V is —C(R$_6$)—, or

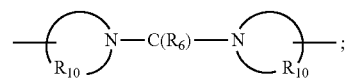

or
R$_5$ is bonded to X$_1$ and R$_5$ is

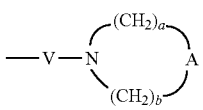

wherein V is —C(R$_6$)— or

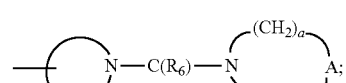

or a pharmaceutically acceptable salt thereof.

In another embodiment of Formula IV, $X_1$ is selected from the group consisting of alkylene and alkenylene, wherein the alkylene and alkenylene are optionally interrupted by one or more —O— groups.

In other embodiments, there is provided a compound of Formula IV-1:

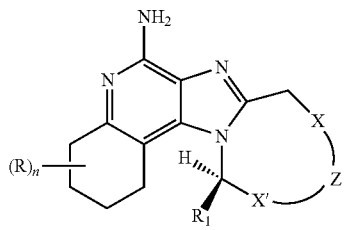

IV-1 wherein X, X', Z, $R_1$, R, and n are as defined in any one of the embodiments of Formula IV above;
or a pharmaceutically acceptable salt thereof.

In one preferred embodiment, there is provided a compound of Formula V:

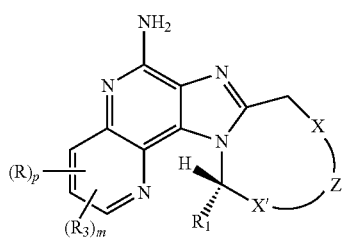

V wherein:
X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;
X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;
X and X' are further characterized in that the sum of the ring carbon atoms contributed by X and X' is 1, 2, or 3;
Z is selected from the group consisting of —O— and —N(—Y—$R_2$)—;
$R_1$ is selected from the group consisting of:
—$X_1$—Y'—$R_4$,
—$X_1$—Y'—X"—Y'—$R_4$, and
—$X_1$—$R_5$;
R is selected from the group consisting of:
halogen,
hydroxy,
alkyl,
alkenyl,
haloalkyl,
alkoxy,
alkylthio, and
—N($R_9$)$_2$;
$R_3$ is selected from the group consisting of:
—Z'—$R_4$,
—Z'—X"—$R_4$,
—Z'—X"—Y'—$R_4$,
—Z'—X"—Y'—X"—Y'—$R_4$, and
—Z'—X"—$R_5$;
p is an integer from 0 to 3;
m is 0 or 1; with the proviso that when m is 1, then p is 0 or 1;
$X_1$ is selected from the group consisting of alkylene and alkenylene, wherein the alkylene and alkenylene are optionally interrupted by one or more —O— groups, and optionally substituted by a hydroxy or methoxy group;
X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
Y is selected from the group consisting of:
a bond,
—S(O)$_2$—,
—S(O)$_2$—N($R_8$)—,
—C($R_6$)—,
—C($R_6$)—N($R_8$)—,
—C($R_6$)—N($R_8$)—C($R_6$)—,
—C($R_6$)—N($R_8$)—S(O)$_2$—, and
—C($R_6$)—O—;
Y' is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

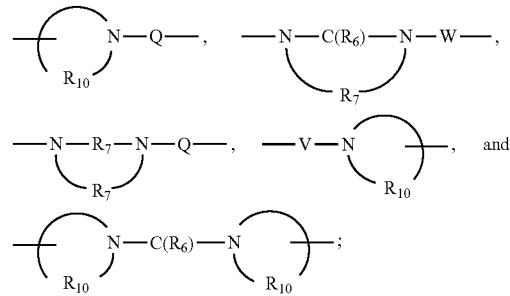

Z' is a bond or —O—;
$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro;

hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

R$_5$ is selected from the group consisting of:

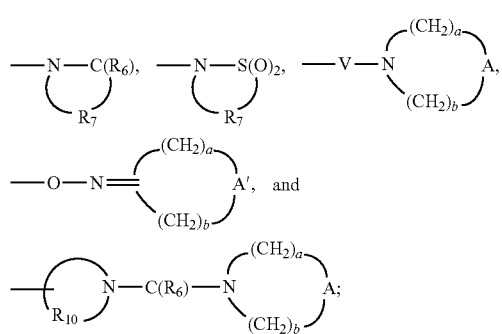

R$_6$ is selected from the group consisting of =O and =S;

R$_7$ is C$_{2-7}$ alkylene;

R$_8$ is selected from the group consisting of hydrogen, C$_{1-10}$alkyl, C$_{2-10}$alkenyl, hydroxy-C$_{1-10}$alkylenyl, C$_{1-10}$alkoxy-C$_{1-10}$alkylenyl, aryl-C$_{1-10}$alkylenyl, and heteroaryl-C$_{1-10}$alkylenyl;

R$_9$ is selected from the group consisting of hydrogen and alkyl;

R$_{10}$ is C$_{3-8}$ alkylene;

A is selected from the group consisting of —CH$_2$—, —O—, —C(O)—, —S(O)$_{0-2}$—, and —N(-Q-R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

with the proviso that X$_1$ can also be a bond when:

Y' is bonded to X$_1$ and Y' is —C(R$_6$)—, —C(R$_6$)—O—, —C(R$_6$)—N(R$_8$)—, —C(R$_6$)—N(OR$_9$)—, —C(=N—O—R$_8$)—, —CH(—N(—O—R$_8$)-Q-R$_4$)—,

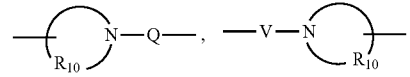

wherein V is —C(R$_6$)—, or

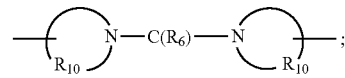

or

R$_5$ is bonded to X$_1$ and R$_5$ is

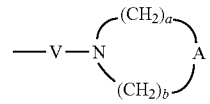

wherein V is —C(R$_6$)— or

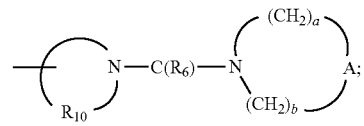

or a pharmaceutically acceptable salt thereof.

In another embodiment of Formula V, X$_1$ is selected from the group consisting of alkylene and alkenylene, wherein the alkylene and alkenylene are optionally interrupted by one or more —O— groups.

In other embodiments, there is provided a compound of Formula V-1:

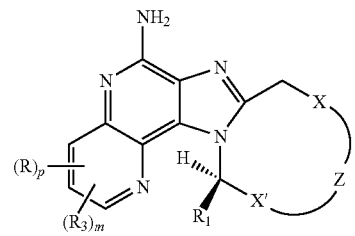

V-1 wherein X, X', Z, R$_1$, R, R$_3$, m, and p are as defined in any one of the embodiments of Formula V above; or a pharmaceutically acceptable salt thereof.

In one preferred embodiment, there is provided a compound of Formula VI:

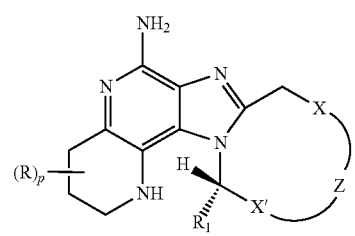

VI wherein:

X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X' is a straight or branched chain $C_{1-8}$alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—$R_2$)—;

$R_1$ is selected from the group consisting of:
—$X_1$—Y'—$R_4$,
—$X_1$—Y'—X"—Y'—$R_4$, and
—$X_1$—$R_5$;

R is selected from the group consisting of:
halogen,
hydroxy,
alkyl,
alkenyl,
haloalkyl,
alkoxy,
alkylthio, and
—N($R_9$)$_2$;

p is an integer from 0 to 3;

$X_1$ is selected from the group consisting of alkylene and alkenylene, wherein the alkylene and alkenylene are optionally interrupted by one or more —O— groups, and optionally substituted by a hydroxy or methoxy group;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
a bond,
—S(O)$_2$—,
—S(O)$_2$—N($R_8$)—,
—C($R_6$)—,
—C($R_6$)—N($R_8$)—,
—C($R_6$)—N($R_8$)—C($R_6$)—,
—C($R_6$)—N($R_8$)—S(O)$_2$—, and
—C($R_6$)—O—;

Y' is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

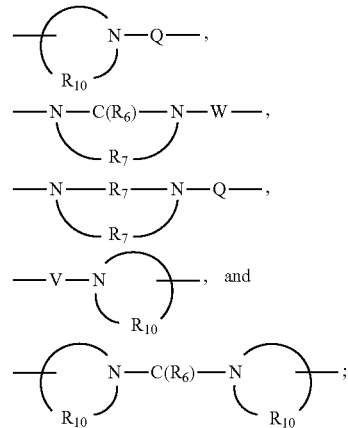

$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

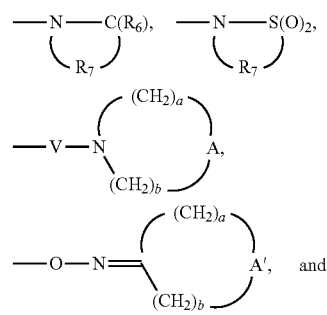

-continued

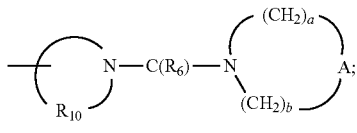

$R_6$ is selected from the group consisting of =O and =S;

$R_7$ is $C_{2-7}$ alkylene;

$R_8$ is selected from the group consisting of hydrogen, $C_{1-10}$alkyl, $C_{2-10}$alkenyl, hydroxy-$C_{1-10}$alkylenyl, $C_{1-10}$alkoxy-$C_{1-10}$alkylenyl, aryl-$C_{1-10}$alkylenyl, and heteroaryl-$C_{1-10}$alkylenyl;

$R_9$ is selected from the group consisting of hydrogen and alkyl;

$R_{10}$ is $C_{3-8}$ alkylene;

A is selected from the group consisting of —CH$_2$—, —O—, —C(O)—, —S(O)$_{0-2}$—, and —N(-Q-R$_4$)—;

A' is selected from the group consisting of —O—, —S(O)$_{0-2}$—, —N(-Q-R$_4$)—, and —CH$_2$—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≦7;

with the proviso that X$_1$ can also be a bond when:

Y' is bonded to X$_1$ and Y' is —C(R$_6$)—, —C(R$_6$)—O—, —C(R$_6$)—N(R$_8$)—, —C(R$_6$)—N(OR$_9$)—, —C(=N—O—R$_8$)—, —CH(—N(—O—R$_8$)-Q-R$_4$)—,

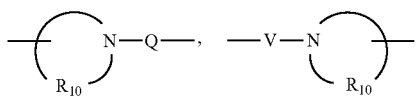

wherein V is —C(R$_6$)—, or

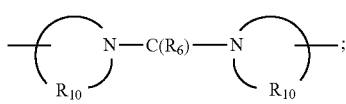

or

R$_5$ is bonded to X$_1$ and R$_5$ is

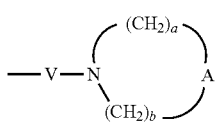

wherein V is —C(R$_6$)— or

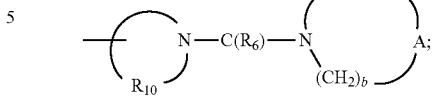

or a pharmaceutically acceptable salt thereof.

In another embodiment of Formula VI, X$_1$ is selected from the group consisting of alkylene and alkenylene, wherein the alkylene and alkenylene are optionally interrupted by one or more —O— groups.

In other embodiments, there is provided a compound of Formula VI-1:

VI-1

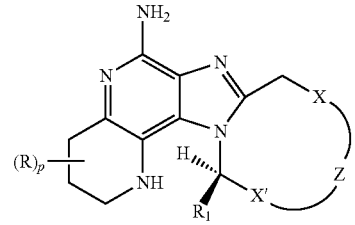

wherein X, X', Z, R$_1$, R, and p are as defined in any one of the embodiments of Formula VI above;

or a pharmaceutically acceptable salt thereof.

In one preferred embodiment, there is provided a compound of Formula VII:

VII

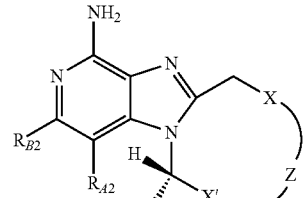

wherein:

X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;

Z is selected from the group consisting of —O— and —N(—Y—R$_2$)—;

R$_1$ is selected from the group consisting of:
—X$_1$—Y'—R$_4$,
—X$_1$—Y'—X"—Y'—R$_4$, and
—X$_1$—R$_5$;

R$_{A2}$ and R$_{B2}$ are each independently selected from the group consisting of:
hydrogen,
halogen,
alkyl, alkenyl,
alkoxy,
alkylthio, and
—N($R_9$)$_2$;

$X_1$ is selected from the group consisting of alkylene and alkenylene, wherein the alkylene and alkenylene are optionally interrupted by one or more —O— groups, and optionally substituted by a hydroxy or methoxy group;

X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:
a bond,
—S(O)$_2$—,
—S(O)$_2$—N($R_8$)—,
—C($R_6$)—,
—C($R_6$)—N($R_8$)—,
—C($R_6$)—N($R_8$)—C($R_6$)—,
—C($R_6$)—N($R_8$)—S(O)$_2$—, and
—C($R_6$)—O—;

Y' is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

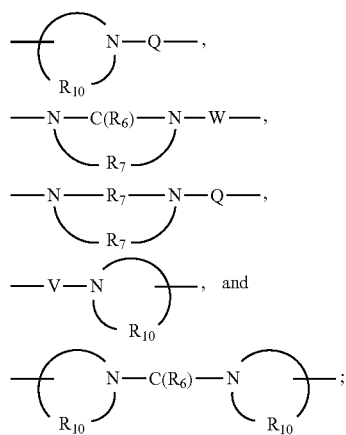

$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

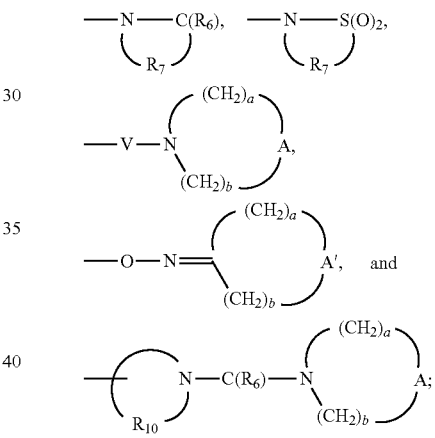

$R_6$ is selected from the group consisting of =O and =S;
$R_7$ is $C_{2-7}$ alkylene;
$R_8$ is selected from the group consisting of hydrogen, $C_{1-10}$alkyl, $C_{2-10}$alkenyl, hydroxy-$C_{1-10}$alkylenyl, $C_{1-10}$alkoxy-$C_{1-10}$alkylenyl, aryl-$C_{1-10}$alkylenyl, and heteroaryl-$C_{1-10}$alkylenyl;
$R_9$ is selected from the group consisting of hydrogen and alkyl;
$R_{10}$ is $C_{3-8}$ alkylene;
A is selected from the group consisting of —CH$_2$—, —O—, —C(O)—, —S(O)$_{0-2}$—, and —N(-Q-$R_4$)—;
A' is selected from the group consisting of —O—, —S(O)$_{0-2}$—, —N(-Q-$R_4$)—, and —CH$_2$—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and a and b are independently integers from 1 to 6 with the proviso that a+b is ≦7;

with the proviso that $X_1$ can also be a bond when:

Y' is bonded to $X_1$ and Y' is —C($R_6$)—, —C($R_6$)—O—, —C($R_6$)—N($R_8$)—, —C($R_6$)—N(O$R_9$)—, —C(=N—O—$R_8$)—, —CH(—N(—O—$R_8$)-Q-$R_4$)—,

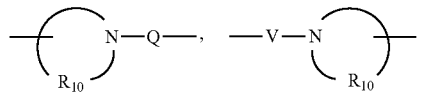

wherein V is —C($R_6$)—, or

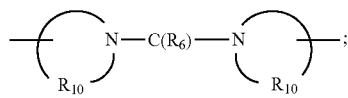

or $R_5$ is bonded to $X_1$ and $R_5$ is

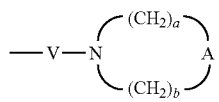

wherein V is —C($R_6$)— or

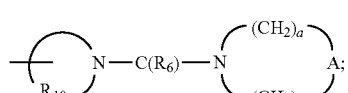

or a pharmaceutically acceptable salt thereof.

In another embodiment of Formula VII, $X_1$ is selected from the group consisting of alkylene and alkenylene, wherein the alkylene and alkenylene are optionally interrupted by one or more —O— groups.

In other embodiments, there is provided a compound of Formula VII-1:

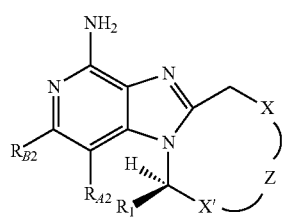

wherein X, X', Z, $R_1$, $R_{A2}$ and $R_{B2}$ are as defined in any one of the embodiments of Formula VII above; or a pharmaceutically acceptable salt thereof.

For certain embodiments, the present invention provides a compound (which is a prodrug) of the Formula VIII:

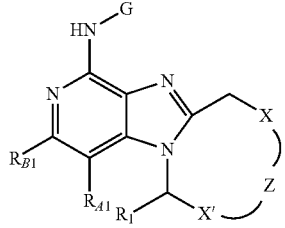

wherein:

G is selected from the group consisting of:
—C(O)—R",
α-aminoacyl,
α-aminoacyl-α-aminoacyl,
—C(O)—O—R",
—C(O)—N(R''')R",
—C(=NY")—R",
—CH(OH)—C(O)—OY",
—CH(O$C_{1-4}$alkyl)$Y_0$,
—$CH_2Y_1$, and
—CH($CH_3$)$Y_1$;

R" and R''' are independently selected from the group consisting of $C_{1-10}$alkyl, $C_{3-7}$cycloalkyl, and benzyl, each of which may be unsubstituted or substituted by one or more substitutents selected from the group consisting of halogen, hydroxy, nitro, cyano, carboxy, $C_{1-6}$ alkyl, $C_{1-4}$alkoxy, aryl, heteroaryl, aryl$C_{1-4}$alkylenyl, heteroaryl$C_{1-4}$alkylenyl, halo$C_{1-4}$alkylenyl, halo$C_{1-4}$alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$, with the proviso that R''' can also be hydrogen;

α-aminoacyl is an acyl group derived from an amino acid selected from the group consisting of racemic, D-, and L-amino acids;

Y" is selected from the group consisting of hydrogen, $C_{1-6}$ alkyl, and benzyl;

$Y_0$ is selected from the group consisting of $C_{1-6}$ alkyl, carboxy$C_{1-6}$alkylenyl, amino$C_{1-4}$alkylenyl, mono-N—$C_{1-6}$ alkylamino$C_{1-4}$alkylenyl, and di-N,N—$C_{1-6}$alkylamino$C_{1-4}$ alkylenyl;

$Y_1$ is selected from the group consisting of mono-N—$C_{1-6}$ alkylamino, di-N,N—$C_{1-6}$alkylamino, morpholin-4-yl, piperidin-1-yl, pyrrolidin-1-yl, and 4-$C_{1-4}$alkylpiperazin-1-yl; and X, X', Z, $R_1$, $R_{A1}$, and $R_{B1}$ are as defined in Formula IIa above;

or a pharmaceutically acceptable salt thereof.

For certain embodiments, there is provided a compound (which is a prodrug) of the Formula IX:

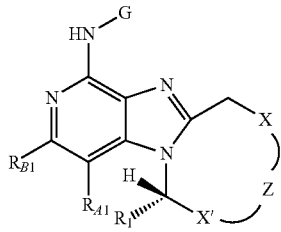

wherein G, X, X', Z, $R_1$, $R_{A1}$, and $R_{B1}$ are as defined in Formula VIII above;
or a pharmaceutically acceptable salt thereof.

For other embodiments of Formula VIII or IX, $X_1$ is selected from the group consisting of alkylene and alkenylene, wherein the alkylene and alkenylene are optionally interrupted by one or more —O— groups.

For certain embodiments, there is provided a compound (which is a prodrug) of the Formula IX-1:

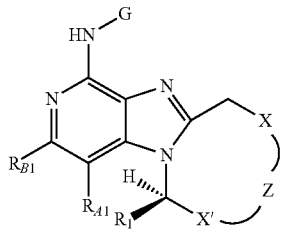

wherein G, X, X', Z, $R_1$, $R_{A1}$, and $R_{B1}$ are as defined in any one of the embodiments of Formula VIII above; or a pharmaceutically acceptable salt thereof.

In one embodiment, the present invention provides an intermediate compound of the following Formula X:

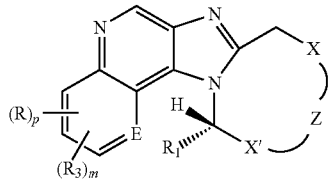

wherein:
E is selected from the group consisting of CH, CR, $CR_3$, and N, with the proviso that when E is $CR_3$, m is 0, and p is 0 or 1, and with the further proviso that when E is CR and m is 1, p is 0;
X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms;
X' is a straight or branched chain $C_{1-8}$ alkylene optionally having a substituent at a carbon atom other than a carbon atom adjacent to a heteroatom, wherein the substituent is hydroxy, alkoxy, or one or more halogen atoms;

X and X' are further characterized in that the sum of the ring carbon atoms contributed by X and X' is 1, 2, or 3;
Z is selected from the group consisting of —O— and —N(—Y—$R_2$)—;
$R_1$ is selected from the group consisting of:
—$X_1$—Y'—$R_4$,
—$X_1$—Y'—X"—Y'—$R_4$, and
—$X_1$—$R_5$;
R is selected from the group consisting of:
halogen,
hydroxy,
alkyl,
alkenyl,
haloalkyl,
alkoxy,
alkylthio, and
—N($R_9$)$_2$;
$R_3$ is selected from the group consisting of:
—Z'—$R_4$,
—Z'—X"—$R_4$,
—Z'—X"—Y'—$R_4$,
—Z'—X"—Y'—X"—Y'—$R_4$, and
—Z'—X"—$R_5$;
p is an integer from 0 to 3;
m is 0 or 1; with the proviso that when m is 1, then p is 0 or 1;
$X_1$ is selected from the group consisting of alkylene and alkenylene, wherein the alkylene and alkenylene are optionally interrupted by one or more —O— groups, and optionally substituted by a hydroxy or methoxy group;
X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;
Y is selected from the group consisting of:
a bond,
—S(O)$_2$—,
—S(O)$_2$—N($R_8$)—,
—C($R_6$)—,
—C($R_6$)—N($R_8$)—,
—C($R_6$)—N($R_8$)—C($R_6$)—,
—C($R_6$)—N($R_8$)—S(O)$_2$—, and
—C($R_6$)—O—;
Y' is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N═C($R_4$)—,
—C(═N—O—$R_8$)—,
—CH(—N(—O—$R_8$)-Q-$R_4$)—,

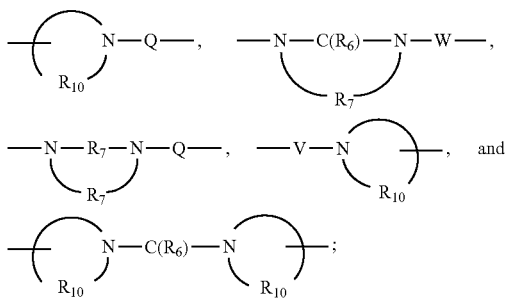

Z' is a bond or —O—;

$R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo;

$R_5$ is selected from the group consisting of:

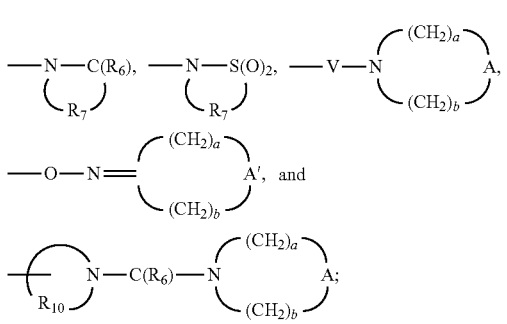

$R_6$ is selected from the group consisting of =O and =S;
$R_7$ is $C_{2-7}$ alkylene;
$R_8$ is selected from the group consisting of hydrogen, $C_{1-10}$alkyl, $C_{2-10}$alkenyl, hydroxy-$C_{1-10}$alkylenyl, $C_{1-10}$alkoxy-$C_{1-10}$alkylenyl, aryl-$C_{1-10}$alkylenyl, and heteroaryl-$C_{1-10}$alkylenyl;

$R_9$ is selected from the group consisting of hydrogen and alkyl;

$R_{10}$ is $C_{3-8}$ alkylene;

A is selected from the group consisting of —$CH_2$—, —O—, —C(O)—, —S(O)$_{0-2}$—, and —N(-Q-$R_4$)—;

A' is selected from the group consisting of —O—, —S(O)$_{0-2}$—, —N(-Q-$R_4$)—, and —$CH_2$—;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;

V is selected from the group consisting of —C($R_6$)—, —O—C($R_6$)—, —N($R_8$)—C($R_6$)—, and —S(O)$_2$—;

W is selected from the group consisting of a bond, —C(O)—, and —S(O)$_2$—; and a and b are independently integers from 1 to 6 with the proviso that a+b is ≦7;

with the proviso that $X_1$ can also be a bond when:

Y' is bonded to $X_1$ and Y' is —C($R_6$)—, —C($R_6$)—O—, —C($R_6$)—N($R_8$)—, —C($R_6$)—N(O$R_9$)—, —C(=N—O—$R_8$)—, —CH(—N(—O—$R_8$)-Q-$R_4$)—,

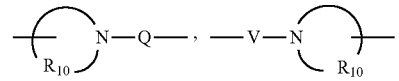

wherein V is —C($R_6$)—, or

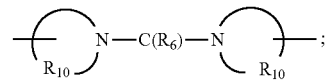

or $R_5$ is bonded to $X_1$ and $R_5$ is

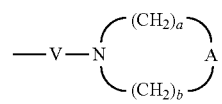

wherein V is —C($R_6$)— or

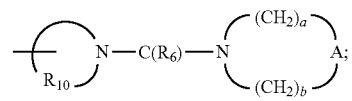

or a pharmaceutically acceptable salt thereof.

In another embodiment of Formula X, $X_1$ is selected from the group consisting of alkylene and alkenylene, wherein the alkylene and alkenylene are optionally interrupted by one or more —O— groups.

In other embodiments, there is provided an intermediate compound of Formula X-1:

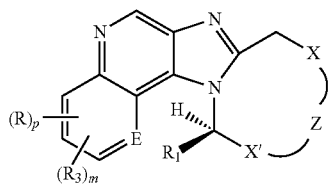

wherein X, X', Z, R₁, E, R, R₃, m, and p are as defined in any one of the embodiments of Formula X above; or a pharmaceutically acceptable salt thereof.

Herein, "non-interfering" means that the ability of the compound or salt, which includes a non-interfering substituent, to modulate the biosynthesis of one or more cytokines is not destroyed by the non-interfering substitutent. For certain embodiments, R' is a non-interfering substituent. Illustrative non-interfering R' groups include those described above for R and R₃.

As used herein, the terms "alkyl," "alkenyl," "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. The terms, "alkylenyl," "alkenylenyl," and "alkynylenyl" are used when "alkylene," "alkenylene," and "alkynylene," respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. In some embodiments, the term "heteroaryl" includes one ring that contains 2-5 carbon atoms, 1-3 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. In some embodiments, the term "heterocyclyl" includes one ring that contains 2-5 carbon atoms, 1-3 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicylic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. The terms, "arylenyl," "heteroarylenyl," and "heterocyclylenyl" are used when "arylene," "heteroarylene," and "heterocyclylene," respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno.

The term "fused heteroaryl ring" includes the fused forms of 5 or 6 membered aromatic rings that contain one heteroatom selected from S and N. Examples of fused heteroaryl rings include pyrido and thieno.

The term "fused 5 to 7 membered saturated ring" includes rings which are fully saturated except for the bond where the ring is fused. In one example, the ring is a cyclohexene ring. In other examples wherein one heteroatom (N or S) is present, the ring is tetrahydropyrido or dihydrothieno.

When a group (or substituent or variable) is present more than once in any Formula described herein, each group (or substituent or variable) is independently selected, whether explicitly stated or not. For example, for the formula —N(R₉)₂ each R₉ group is independently selected. In another example, when a Y and a Y' group are both present and both contain an R₈ group, each R₈ group is independently selected. In a further example, when more than one Y' group is present (i.e., R₁ and R₃ each contains a Y' group) and each Y' group contains one or more R₇ groups, then each Y' group is independently selected, and each R₇ group is independently selected.

The invention is inclusive of the compounds described herein (including intermediates) in any of their pharmaceutically acceptable forms, including isomers (e.g., diastereomers and enantiomers), salts, solvates, polymorphs, prodrugs, and the like. In particular, the invention specifically includes mixtures of the compound with its enantiomer in any ratio as well as the racemic mixture. Ratios of the compound to its enantiomer include, for example, 50:50 or higher, 90:10 or higher, 95:5 or higher, 99:1 or higher, 99.9:0.1 or higher, or 100:0. It should be understood that the term "compound" includes any or all of such forms, whether explicitly stated or not (although at times, "salts" are explicitly stated).

The term "prodrug" means a compound that can be transformed in vivo to yield an immune response modifying compound in any of the salt, solvated, polymorphic, or isomeric forms described above. The prodrug, itself, may be an immune response modifying compound in any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., X, X', $X_1$, Z, R, $R_1$, $R_3$, $R_4$, $R_B$, $R_{A1}$, $R_{B1}$, $R_{A2}$, $R_{B2}$, E, m, n, and p and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, R is selected from the group consisting of halogen, hydroxy, alkyl, alkenyl, haloalkyl, alkoxy, alkylthio, and —N($R_9$)$_2$.

For certain embodiments, R is halogen or hydroxy.

For certain embodiments, $R_1$ is selected from the group consisting of —$X_1$—Y'—$R_4$, —$X_1$—Y'—X"—Y'—$R_4$, and —$X_1$—$R_5$.

For certain embodiments, $R_1$ is —$X_1$—Y'—$R_4$.

For certain embodiments, $R_1$ is —$X_1$—Y'—X"—Y'—$R_4$.

For certain embodiments, $R_1$ is —$X_1$—$R_5$.

For certain embodiments, $R_2$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; alkylthio; alkanoyl; alkanoyloxy; alkoxycarbonyl; hydroxyalkyl; haloalkyl; haloalkoxy; halogen; nitro; hydroxy; mercapto; cyano; aryl; aryloxy; arylthio; arylalkyleneoxy; heteroaryl; heteroaryloxy; heteroarylalkyleneoxy; heterocyclyl; amino; alkylamino; dialkylamino; (dialkylamino)alkyleneoxy; in the case of alkyl, alkenyl, alkynyl, and heterocyclyl, oxo; and, in the case of aryl, methylenedioxy.

For certain embodiments, $R_2$ is alkyl.

For certain embodiments, $R_2$ is methyl.

For certain embodiments, $R_3$ is selected from the group consisting of —Z'—$R_4$, —Z'—X"—$R_4$, —Z'—X"—Y'—$R_4$, —Z'—X"—Y'—X"—Y'—$R_4$, and —Z'—X"—$R_5$.

For certain embodiments, $R_3$ is selected from the group consisting of benzyloxy which is unsubstituted or substituted by halogen or haloalkyl, 3-pyrrolylpropoxy, 2-(4-methoxyphenyl)-2-oxoethoxy, aryl, and heteroaryl, wherein aryl and heteroaryl are unsubstituted or substituted by one or more substituents independently selected from the group consisting of alkyl, hydroxy, hydroxyalkyl, alkoxy, halogen, dialkylamino, alkylcarbonylamino, alkylaminocarbonyl, dialkylaminocarbonyl, and heterocyclylcarbonyl. In certain of these embodiments, heterocyclylcarbonyl is pyrrolidinylcarbonyl or morpholinylcarbonyl.

For certain embodiments, $R_3$ is phenyl substituted by pyrrolidinylcarbonyl or morpholinylcarbonyl.

For certain embodiments, $R_3$ is benzyloxy.

For certain embodiments, $R_3$ is at the 3-position with the positions numbered as follows:

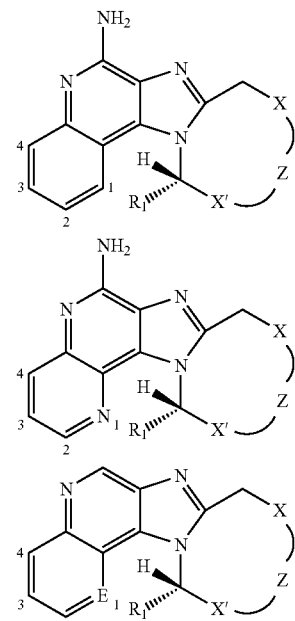

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; nitro; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl, alkenyl, alkynyl, and heterocyclyl, oxo.

For certain embodiments, $R_4$ is alkyl, arylalkylenyl, aryl, or heteroaryl wherein arylalkylenyl, aryl, or heteroaryl are optionally substituted by alkyl.

For certain embodiments, $R_4$ is hydrogen, alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino.

For certain embodiments, $R_4$ is hydrogen, alkyl, alkenyl, aryl, arylalkylenyl, heteroaryl, or heterocyclyl wherein alkyl, alkenyl, aryl, arylalkylenyl, heteroaryl, and heterocyclyl are unsubstituted or substituted by one or more substituents independently selected from the group consisting of hydroxy, halogen, alkoxy, alkyl, and haloalkyl.

For certain embodiments, $R_4$ is alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino.

For certain embodiments, $R_4$ is aryl which is unsubstituted or substituted by one or more substituents independently selected from the group consisting of alkyl, alkoxy, halogen, and dialkylamino.

For certain embodiments, $R_4$ is alkyl or aryl.

For certain embodiments, $R_4$ is alkyl.

For certain embodiments, $R_5$ is selected from the group consisting of:

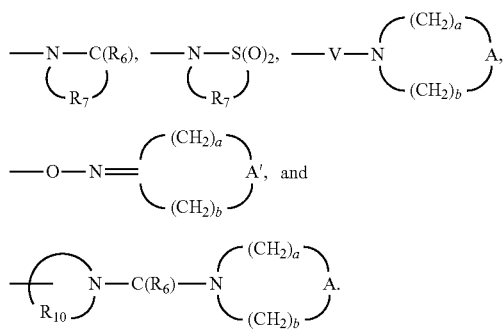

For certain embodiments, $R_5$ is selected from the group consisting of:

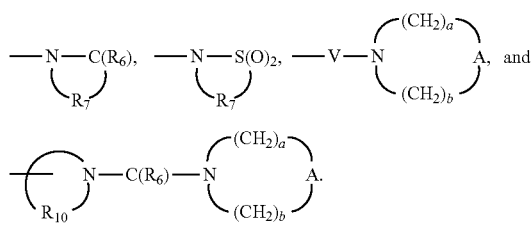

For certain embodiments, $R_5$ is selected from the group consisting of:

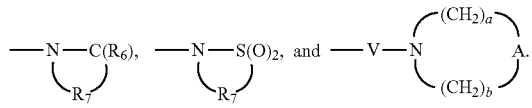

For certain embodiments, $R_5$ is

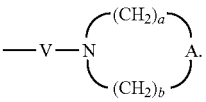

For certain of these embodiments, A is —CH$_2$—, —O—, or —N(-Q-R$_4$)—, and V is —C(O)—. For certain of these embodiments, A is —CH$_2$—, and V is —C(O)—.

For certain embodiments, $R_6$ is selected from the group consisting of =O and =S. For certain embodiments, $R_6$ is =O.

For certain embodiments, $R_7$ is $C_{2-7}$ alkylene.

For certain embodiments, $R_7$ is $C_{2-3}$ alkylene.

For certain embodiments, $R_7$ is propylene.

For certain embodiments, $R_8$ is selected from the group consisting of hydrogen, $C_{1-10}$alkyl, $C_{2-10}$alkenyl, hydroxy-$C_{1-10}$alkylenyl, $C_{1-10}$alkoxy-$C_{1-10}$alkylenyl, aryl-$C_{1-10}$alkylenyl, and heteroaryl-$C_{1-10}$alkylenyl.

For certain embodiments, $R_8$ is selected from the group consisting of hydrogen, $C_{1-10}$alkyl, $C_{2-10}$alkenyl, $C_{1-10}$alkoxy-$C_{1-10}$alkylenyl, and aryl-$C_{1-10}$alkylenyl.

For certain embodiments, $R_8$ is independently selected from the group consisting of hydrogen, $C_{1-4}$alkyl, hydroxy$C_{1-4}$alkyl, and $C_{1-4}$alkoxy$C_{1-4}$alkyl.

For certain embodiments, $R_8$ is hydrogen, methyl, ethyl, 2-hydroxyethyl, or 2-methoxyethyl.

For certain embodiments, $R_8$ is hydrogen or $C_{1-4}$alkyl.

For certain embodiments, $R_8$ is hydrogen or methyl.

For certain embodiments, $R_8$ is hydrogen.

For certain embodiments, $R_9$ is selected from the group consisting of hydrogen and alkyl.

For certain embodiments, $R_9$ is alkyl.

For certain embodiments, $R_9$ is hydrogen.

For certain embodiments, $R_{10}$ is $C_{3-8}$ alkylene.

For certain embodiments, $R_{10}$ is $C_{4-6}$ alkylene.

For certain embodiments, $R_{10}$ is pentylene.

For certain embodiments, $R_A$ and $R_B$ are each independently selected from the group consisting of hydrogen, halogen, alkyl, alkenyl, alkoxy, alkylthio, and —N(R$_9$)$_2$; or when taken together, $R_A$ and $R_B$ form a fused aryl ring or heteroaryl ring containing one heteroatom selected from the group consisting of N and S, wherein the fused aryl or heteroaryl ring is unsubstituted or substituted by one or more W groups; or when taken together, $R_A$ and $R_B$ form a fused 5 to 7 membered saturated ring, optionally containing one heteroatom selected from the group consisting of N and S, and unsubstituted or substituted by one or more R groups.

For certain embodiments, $R_A$ and $R_B$ are each independently selected from the group consisting of hydrogen, halogen, alkyl, alkenyl, alkoxy, alkylthio, and —N(R$_9$)$_2$.

For certain embodiments, $R_A$ and $R_B$ form a fused aryl ring or heteroaryl ring.

For certain embodiments, $R_A$ and $R_B$ form a fused 5 to 7 membered saturated ring, optionally containing one heteroatom.

For certain embodiments, $R_{A1}$ and $R_{B1}$ are each independently selected from the group consisting of hydrogen, halogen, alkyl, alkenyl, alkoxy, alkylthio, and —N(R$_9$)$_2$; or when taken together, $R_{A1}$ and $R_{B1}$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group; or when taken together, $R_{A1}$ and $R_{B1}$ form a fused 5 to 7 membered saturated ring, optionally containing one heteroatom selected from the group consisting of N and S, and unsubstituted or substituted by one or more R groups.

For certain embodiments, $R_{A1}$ and $R_{B1}$ form a benzo ring which is unsubstituted or substituted by one or more R groups, or substituted by one $R_3$ group, or substituted by one $R_3$ group and one R group. For certain embodiments, $R_{A1}$ and $R_{B1}$ form a benzo ring which is unsubstituted.

For certain embodiments, $R_{A1}$ and $R_{B1}$ form a pyrido ring which is unsubstituted or substituted by one or more R groups, or substituted by one $R_3$ group, or substituted by one $R_3$ group and one R group. For certain embodiments, $R_{A1}$ and $R_{B1}$ form a pyrido ring which is unsubstituted. For certain embodiments, the pyrido ring is

wherein the highlighted bond indicates the position where the ring is fused.

For certain embodiments, $R_{A1}$ and $R_{B1}$ form a fused 5 to 7 membered saturated ring, optionally containing one heteroatom selected from the group consisting of N and S, wherein the ring is unsubstituted. For certain embodiments, $R_{A1}$ and $R_{B1}$ form a fused cyclohexene ring that is unsubstituted or substituted by one, two, three, or four R groups. For certain embodiments, $R_{A1}$ and $R_{B1}$ form a fused cyclohexene ring that is unsubstituted.

For certain embodiments, $R_{A1}$ and $R_{B1}$ form a tetrahydropyrido ring that is unsubstituted or substituted on one or more ring carbon atoms by one, two, or three R groups. For certain embodiments, $R_{A1}$ and $R_{B1}$ form a tetrahydropyrido ring that is unsubstituted. For certain embodiments, the tetrahydropyrido ring is

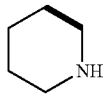

wherein the highlighted bond indicates the position where the ring is fused.

For certain embodiments, $R_{A2}$ and $R_{B2}$ are each independently selected from the group consisting of hydrogen, halogen, alkyl, alkenyl, alkoxy, alkylthio, and $—N(R_9)_2$. For certain embodiments, $R_{A2}$ and $R_{B2}$ are each methyl.

For certain embodiments, A is selected from the group consisting of $—CH_2—$, $—O—$, $—C(O)—$, $—S(O)_{0-2}—$, and $—N(\text{-}Q\text{-}R_4)—$.

For certain embodiments, A is selected from the group consisting of $—CH_2—$, $—O—$, and $—N(\text{-}Q\text{-}R_4)—$.

For certain embodiments, A is $—O—$.
For certain embodiments, A is $—CH_2—$.
For certain embodiments, A is $—N(\text{-}Q\text{-}R_4)—$.

For certain embodiments, E is selected from the group consisting of CH, CR, $CR_3$, and N, with the proviso that when E is $CR_3$, m is 0, and p is 0 or 1, and with the further proviso that when E is CR and m is 1, p is 0. For certain embodiments, E is CH. For certain embodiments, E is N. For certain embodiments, E is CR. For certain embodiments, E is $CR_3$.

For certain embodiments, Q is selected from the group consisting of a bond, $—C(R_6)—$, $—C(R_6)—C(R_6)—$, $—S(O)_2—$, $—C(R_6)—N(R_8)—W—$, $—S(O)_2—N(R_8)—$, $—C(R_6)—O—$, $—C(R_6)—S—$, and $—C(R_6)—N(OR_9)—$.

For certain embodiments, Q is selected from the group consisting of a bond, $—C(R_6)—$, $—C(R_6)—C(R_6)—$, $—S(O)_2—$, $—C(R_6)—N(R_8)—W—$, $—S(O)_2—N(R_8)—$, $—C(R_6)—O—$, and $—C(R_6)—N(OR_9)—$.

For certain embodiments, Q is a bond, $—S(O)_2—$, $—C(O)—$, $—C(O)—O—$, $—C(O)—N(R_8)—$, $—C(S)—N(R_8)—$, or $—S(O)_2—N(R_8)—$.

For certain embodiments, Q is a bond, $—C(O)—$, $—S(O)_2—$, $—S(O)_2—N(R_8)—$, $—C(O)—N(R_8)—$, $C(S)—N(R_8)—$, or $—C(O)—O—$.

For certain embodiments, Q is $—C(O)—$, $—S(O)_2$, $—S(O)_2—N(R_8)—$, or $—C(O)—N(R_8)—$. For certain embodiments, Q is $—C(R_6)—$.

For certain embodiments, Q is $—S(O)_2—$.
For certain embodiments, Q is $—C(R_6)—N(R_8)—W—$.
For certain embodiments, Q is a bond.

For certain embodiments, V is selected from the group consisting of $—C(R_6)—$, $—O—C(R_6)—$, $—N(R_8)—C(R_6)—$, and $—S(O)_2—$.

For certain embodiments, V is $—C(R_6)—$.
For certain embodiments, V is $—C(O)—$.
For certain embodiments, V is $N(R_8)—C(R_6)—$.
For certain embodiments, V is $—N(R_8)—C(O)—$.

For certain embodiments, W is selected from the group consisting of a bond, $—C(O)—$, and $—S(O)_2—$.

For certain embodiments, W is a bond.

For certain embodiments, X is a bond or a straight or branched chain $C_{1-8}$ alkylene optionally having a substituent at a carbon atom other than a carbon atom adjacent to a heteroatom, wherein the substituent is hydroxy, alkoxy, or one or more halogen atoms.

For certain embodiments, X is a bond.

For certain embodiments, X is a straight or branched chain $C_{1-8}$ alkylene optionally having a substituent at a carbon atom other than a carbon atom adjacent to a heteroatom, wherein the substituent is hydroxy, alkoxy, or one or more halogen atoms.

For certain embodiments, X' contributes one ring carbon atom.

For certain embodiments, X' is $C_{1-2}$alkylene.
For certain embodiments, X' is methylene.
For certain embodiments, X' contributes two ring carbon atoms.

In each of the above embodiments of X and X', X and X' are further characterized in that the sum of the ring carbon atoms contributed by X and X is 1, 2, or 3.

For certain embodiments, $X_1$ is selected from the group consisting of alkylene and alkenylene, wherein the alkylene and alkenylene are optionally interrupted by one or more $—O—$ groups, and optionally substituted by a hydroxy or methoxy group.

For certain embodiments, $X_1$ is selected from the group consisting of alkylene and alkenylene, wherein the alkylene and alkenylene are optionally interrupted by one or more $—O—$ groups.

For certain embodiments, $X_1$ is alkylene.
For certain embodiments, $X_1$ is $C_{1-4}$alkylene.
For certain embodiments, $X_1$ is $C_{1-3}$ alkylene optionally substituted by a hydroxy or methoxy group.
For certain embodiments, $X_1$ is $—(CH_2)_{1-3}—$.
For certain embodiments, $X_1$ is $C_{2-3}$alkylene substituted by one hydroxy group.

For certain embodiments, $X_1$ is a bond, and the Y' bonded to $X_1$ is —C($R_6$)—, —C($R_6$)—O—, —C($R_6$)—N($R_8$)—, —C($R_6$)—N(O$R_9$)—, —C(=N—O—$R_8$)—, —CH(—N(—O—$R_8$)-Q-$R_4$)—,

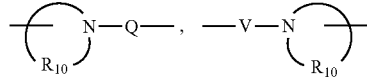

wherein V is —C($R_6$)—, or

For certain embodiments, $X_1$ is a bond, $R_5$ is bonded to $X_1$, and $R_5$ is

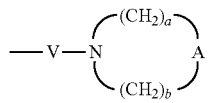

wherein V is —C($R_6$)— or

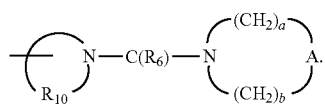

For certain embodiments, X" is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups.

For certain embodiments, X" is alkylene.

For certain embodiments, Y is selected from the group consisting of a bond, —S(O)$_2$—, —S(O)$_2$—N($R_8$)—, —C($R_6$)—, —C($R_6$)—N($R_8$)—, —C($R_6$)—N($R_8$)—C($R_6$)—, —C($R_6$)—N($R_8$)—S(O)$_2$—, and —C($R_6$)—O—.

For certain embodiments, Y is selected from the group consisting of —C(O)—, —S(O)$_2$—, and —C(O)NH—.

For certain embodiments, Y is —S(O)$_2$—.

For certain embodiments, Y' is selected from the group consisting of —O—, —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N(O$R_9$)—, —O—N($R_8$)-Q-, —O—N=C($R_4$)—, —C(=N—O—$R_8$)—, —CH(—N(—O—$R_8$)-Q-$R_4$)—,

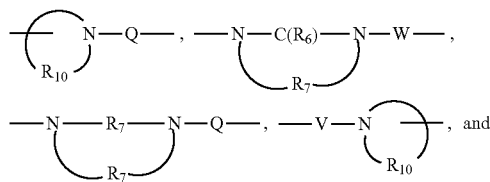

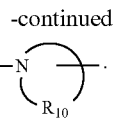

For certain embodiments, Y' is selected from the group consisting of —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N(O$R_9$)—, —O—N($R_8$)-Q-, —O—N=C($R_4$)—, —C(=N—O—$R_8$)—, —CH(—N(—O—$R_8$)-Q-$R_4$)—,

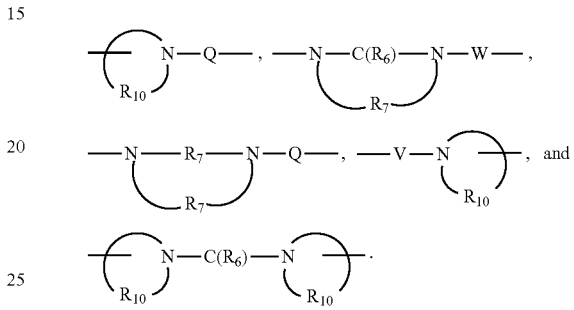

For certain embodiments, Y' is —C(O)—, —S(O)$_2$—, —N($R_8$)-Q-, or —C(O)—NH—.

For certain embodiments, Y' is —S—, —S(O)$_2$—, or N($R_8$)-Q-.

For certain embodiments, Y' is —NH—S(O)$_2$—, —NH—C(O)—, —NH—S(O)$_2$—N($R_8$)—, —NH—C(O)—N($R_8$)—, —NH—C(S)—N($R_8$)—, —NH—C(O)—O—, or —N($R_8$)—.

For certain embodiments, Y' is —S— or —S(O)$_2$—.

For certain embodiments, Y' is —S(O)$_2$—.

For certain embodiments, Y' is —C(O)—.

For certain embodiments, Y' is —O—.

For certain embodiments, Y' is

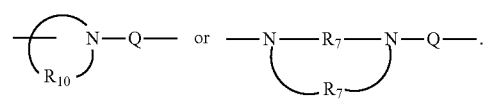

For certain embodiments, Y' is

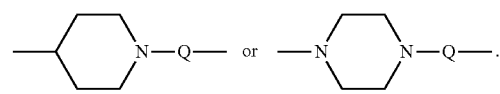

For certain embodiments, Y' is

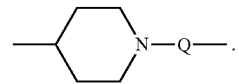

For certain embodiments, Y' is

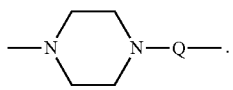

For certain embodiments, Z is selected from the group consisting of —O— and —N(Y—R$_2$)—.
For certain preferred embodiments, Z is —O—.
For certain embodiments, Z is —N(—Y—R$_2$)—.
For certain embodiments, Z' is a bond or —O—.
For certain embodiments, Z' is a bond.
For certain embodiments, Z' is —O—.
For certain embodiments, a and b are independently integers from 1 to 6 with the proviso that a+b is ≦7.
For certain embodiments, a and b are each 2 or 3.
For certain embodiments, a and b are each 2.
For certain embodiments, m is 0 or 1.
For certain embodiments, m is 0.
For certain embodiments, m is 1.
For certain embodiments, n is an integer from 0 to 4.
For certain embodiments, n is 0 or 1.
For certain embodiments, n is 0.
For certain embodiments, n is 1.
For certain embodiments, n is 2.
For certain embodiments, n is 3 or 4.
For certain embodiments, p is an integer from 0 to 3.
For certain embodiments, p is 0 or 1.
For certain embodiments, p is 0.
For certain embodiments, p is 1.
For certain embodiments, m is 1 and n is 0.
For certain embodiments, m is 0 and n is 0.
For certain embodiments, m is 1 and p is 0.
For certain embodiments, m is 0 and p is 0.

In some embodiments, particularly embodiments of Formulas I, II, or II-1, the one or more W groups are one or more R groups, or one R$_3$ group, or one R$_3$ group and one R group; wherein R and R$_3$ are as defined in Formula IIa or are any one of the embodiments of R and/or R$_3$ defined above.

In some embodiments, particularly embodiments of Formula I, R$_A$ and R$_B$ form a benzo ring which is unsubstituted or substituted by one or more R groups, or substituted by one R$_3$ group, or substituted by one R$_3$ group and one R group. For certain embodiments, R$_A$ and R$_B$ form a benzo ring which is unsubstituted.

In some embodiments, particularly embodiments of Formula I, R$_A$ and R$_B$ form a pyrido ring which is unsubstituted or substituted by one or more R groups, or substituted by one R$_3$ group, or substituted by one R$_3$ group and one R group. For certain embodiments, R$_A$ and R$_B$ form a pyrido ring which is unsubstituted. For certain embodiments, the pyrido ring is

wherein the highlighted bond indicates the position where the ring is fused.

In some embodiments, particularly embodiments of Formula I, R$_A$ and R$_B$ form a fused 5 to 7 membered saturated ring, optionally containing one heteroatom selected from the group consisting of N and S, wherein the ring is unsubstituted.

For certain embodiments, R$_A$ and R$_B$ form a fused cyclohexene ring that is unsubstituted or substituted by one, two, three, or four R groups. For certain embodiments, R$_A$ and R$_B$ form a fused cyclohexene ring that is unsubstituted. For certain embodiments, R$_A$ and R$_B$ form a tetrahydropyrido ring that is unsubstituted or substituted on one or more ring carbon atoms by one, two, or three R groups. For certain embodiments, R$_A$ and R$_B$ form a tetrahydropyrido ring that is unsubstituted. For certain embodiments, the tetrahydropyrido ring is

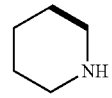

wherein the highlighted bond indicates the position where the ring is fused.

In some embodiments, particularly embodiments of Formula I, R$_A$ and R$_B$ are each independently selected from the group consisting of hydrogen, halogen, alkyl, alkenyl, alkoxy, alkylthio, and —N(R$_9$)$_2$. For certain embodiments, R$_A$ and R$_B$ are each methyl.

In some embodiments, particularly embodiments of Formulas VII or VII-1, R$_{A2}$ and R$_{B2}$ are each independently selected from the group consisting of hydrogen, halogen, alkyl, alkenyl, alkoxy, alkylthio, and —N(R$_9$)$_2$. In certain of these embodiments, R$_{A2}$ and R$_{B2}$ are each methyl.

In some embodiments, particularly embodiments of Formulas III, III-1, IV, or IV-1, n is an integer from 0 to 4. In certain of these embodiments, n is 0.

In some embodiments, particularly embodiments of Formulas V, V-1, VI, or VI-1, p is an integer from 0 to 3. In certain of these embodiments, p is 0.

In some embodiments, particularly embodiments of Formulas III or III-1, n is an integer from 0 to 4 and m is 0 or 1; with the proviso that when m is 1, then n is 0 or 1. In certain of these embodiments, n and m are 0.

In some embodiments, particularly embodiments of Formulas V or V-1, p is an integer from 0 to 3, and m is 0 or 1; with the proviso that when m is 1, then p is 0 or 1. In certain of these embodiments, p and m are 0.

In some embodiments, particularly embodiments of Formulas X or X-1, E is CH or N, p is 0, and m is 0 or 1. In certain of these embodiments, p and m are 0.

In some embodiments, particularly embodiments of Formulas IIa, II-1a, III, III-1, V, V-1, VIII, IX, IX-1, X, or X-1, R$_3$ is selected from the group consisting of benzyloxy which is unsubstituted or substituted by halogen or haloalkyl, 3-pyrrolylpropoxy, 2-(4-methoxyphenyl)-2-oxoethoxy, aryl, and heteroaryl, wherein aryl and heteroaryl are unsubstituted or substituted by one or more substituents independently selected from the group consisting of alkyl, hydroxy, hydroxyalkyl, alkoxy, halogen, dialkylamino, alkylcarbonylamino, alkylaminocarbonyl, dialkylaminocarbonyl, and heterocyclylcarbonyl.

For certain embodiments, particularly embodiments of Formulas IIa, II-1a, III, III-1, V, V-1, VIII, IX, IX-1, X, or X-1, R$_3$ is phenyl substituted by pyrrolidinylcarbonyl or morpholinylcarbonyl.

In certain embodiments, particularly embodiments of Formulas IIa, II-1a, III, III-1, V, V-1, VIII, IX, IX-1, X, or X-1, R$_3$ is benzyloxy.

In some embodiments, particularly embodiments of Formulas I, II, II-1, IIa, II-1a, III, III-1, IV, IV-1, V, V-1, VI, VI-1, VIII, IX, IX-1, X, or X-1, R is halogen or hydroxy.

In certain embodiments, particularly embodiments of Formulas IIa, II-1a, III, III-1, V, V-1, VIII, IX, IX-1, X, or X-1, wherein $R_3$ is benzyloxy, R is halogen or hydroxy.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments, Z is —N(—Y—$R_2$)—.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments (except where Z is —N(—Y—$R_2$)—), Z is —O—.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments (except where Z is —O—), Y is selected from the group consisting of —C(O)—, —S(O)$_2$—, and —C(O)—NH—. In certain of these embodiments, Y is —S(O)$_2$— and $R_2$ is methyl.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments, $R_1$ is —$X_1$—Y'—$R_4$.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments (except where $R_1$ is —$X_1$—Y'—$R_4$), $R_1$ is —$X_1$—Y'—X'—Y'—$R_4$.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments (except where $R_1$ is —$X_1$—Y'—$R_4$ or —$X_1$—Y'—X"—Y'—$R_4$), $R_1$ is —$X_1$—$R_5$.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments, $X_1$ is $C_{1-4}$alkylene.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments wherein Y' is present, Y' is —C(O)—, —S(O)$_2$—, —N($R_8$)-Q-, or —C(O)—NH—. In certain of these embodiments, Q is —C(O)—, —S(O)$_2$, —S(O)$_2$—N($R_8$)—, or —C(O)—N($R_8$)—.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments wherein $R_4$ is present, $R_4$ is alkyl, aryl, arylalkylenyl, or heteroaryl, wherein aryl, arylalkylenyl, and heteroaryl are optionally substituted by alkyl.

Alternatively, for certain embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments wherein $R_1$ is —$X_1$—Y'—$R_4$, Y' is —S—, —S(O)$_2$—, or N($R_8$)-Q- wherein Q is a bond, —S(O)$_2$—, —C(O)—, —C(O)—O—, —C(O)—N($R_8$)—, —C(S)—N($R_8$)—, or —S(O)$_2$—N($R_8$)—; each $R_8$ is independently selected from the group consisting of hydrogen, $C_{1-4}$alkyl, hydroxy$C_{1-4}$alkyl, and $C_{1-4}$alkoxy$C_{1-4}$alkyl; and $R_4$ is hydrogen, alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino; except for the above embodiments which do not include this definition. For certain of these embodiments, Y' is —NH—S(O)$_2$—, —NH—C(O)—, —NH—S(O)$_2$—N($R_8$)—, —NH—C(O)—N($R_8$)—, —NH—C(S)—N($R_8$)—, —NH—C(O)—O—, or —N($R_8$)—; and $R_8$ is hydrogen, methyl, ethyl, 2-hydroxyethyl, or 2-methoxyethyl. For certain of these embodiments, Y' is —N($R_8$)—; $R_4$ is hydrogen, methyl, ethyl, n-propyl, n-butyl, 2-hydroxyethyl, 2-methoxyethyl, phenyl, benzyl, pyridin-2-yl, pyridin-3-yl, or pyridin-4-yl; and $R_8$ is hydrogen. For certain of these embodiments, Y' is —NH—C(O)—, and $R_4$ is methyl, ethyl, n-propyl, n-butyl, 2-methylpropyl, cyclopropyl, cyclopentyl, cyclohexyl, or pyridin-3-yl. For certain of these embodiments, Y' is —NH—S(O)$_2$—, and $R_4$ is methyl, ethyl, n-propyl, n-butyl, 1-methylethyl, 2,2,2-trifluoroethyl, phenyl, or benzyl. For certain of these embodiments, Y' is —NH—C(O)—N($R_8$)—; $R_4$ is methyl, ethyl, n-propyl, 1-methylethyl, n-butyl, cyclopropyl, cyclopentyl, cyclohexyl, phenyl, benzyl, pyrrolidin-1-yl, piperidin-1-yl, or morpholin-4-yl; and $R_8$ is hydrogen. For certain of these embodiments, Y' is —NH—C(S)—N($R_8$)—; $R_4$ is methyl, ethyl, n-propyl, 1-methylethyl, cyclopropyl, n-butyl, 2-methylpropyl, methylcyclopropyl, or pyridin-3-yl; and $R_8$ is hydrogen. For certain of these embodiments, Y' is —NH—C(O)—O—, and $R_4$ is methyl, ethyl, n-propyl, n-butyl, t-butyl, phenyl or benzyl. Alternatively, for certain of these embodiments, Y' is —S— or —S(O)$_2$—; and $R_4$ is alkyl or aryl. For certain of these embodiments, $R_4$ is methyl, ethyl, n-propyl, n-butyl, or phenyl. For certain of these embodiments, $X_1$ is $C_{1-3}$ alkylene optionally substituted by a hydroxy or methoxy group; except for the above embodiments which do not include a hydroxy or methoxy group as a substituent in $X_1$. For certain of these embodiments, $X_1$ is —(CH$_2$)$_{1-3}$—. Alternatively, for certain of these embodiments, $X_1$ is $C_{2-3}$ alkylene substituted by one hydroxy group.

Alternatively, for certain embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments wherein $R_1$ is —$X_1$—Y'—$R_4$, Y' is

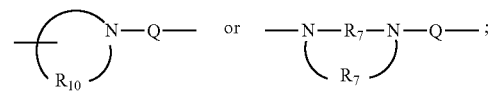

Q is a bond, —C(O)—, —S(O)$_2$—, —S(O)$_2$—N($R_8$)—, —C(O)—N($R_8$)—, C(S)—N($R_8$)—, or —C(O)—O—; $R_7$ is $C_{2-3}$ alkylene; $R_8$ is hydrogen or $C_{1-4}$alkyl; $R_{10}$ is $C_{4-6}$alkylene; and $R_4$ is hydrogen, alkyl, alkenyl, aryl, arylalkylenyl, heteroaryl, or heterocyclyl wherein alkyl, alkenyl, aryl, arylalkylenyl, heteroaryl, and heterocyclyl are unsubstituted or substituted by one or more substituents independently selected from the group consisting of hydroxy, halogen, alkoxy, alkyl, and haloalkyl. For certain of these embodiments, Y' is

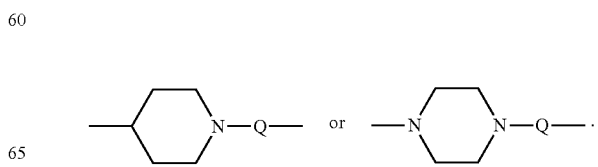

For certain of these embodiments, $X_1$ is a bond or —$CH_2$—, and Y' is

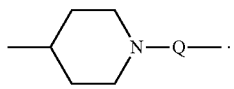

Alternatively, for certain of these embodiments, $X_1$ is a —$CH_2$— or —$(CH_2)_2$—, and Y' is

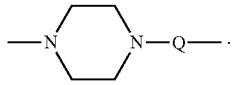

For certain of these embodiments, Q is a bond, and $R_4$ is hydrogen, methyl, ethyl, n-propyl, n-butyl, 2-hydroxyethyl, 2-methoxyethyl, phenyl, benzyl, pyridin-2-yl, pyridin-3-yl, or pyridin-4-yl. For certain of these embodiments, Q is —C(O)—, and $R_4$ is methyl, ethyl, n-propyl, n-butyl, 2-methylpropyl, cyclopropyl, cyclopentyl, cyclohexyl, or pyridin-3-yl. For certain of these embodiments, Q is —$S(O)_2$—, and $R_4$ is methyl, ethyl, n-propyl, n-butyl, 1-methylethyl, 2,2,2-trifluoroethyl, phenyl, or benzyl. For certain of these embodiments, Q is —C(O)—N($R_8$)—; $R_4$ is methyl, ethyl, n-propyl, 1-methylethyl, n-butyl, cyclopropyl, cyclopentyl, cyclohexyl, phenyl, benzyl, pyrrolidin-1-yl, piperidin-1-yl, or morpholin-4-yl; and $R_8$ is hydrogen. For certain of these embodiments, Q is —C(S)—N($R_8$)—; $R_4$ is methyl, ethyl, n-propyl, 1-methylethyl, cyclopropyl, n-butyl, 2-methylpropyl, methylcyclopropyl, or pyridin-3-yl; and $R_8$ is hydrogen. For certain of these embodiments, Q is —C(O)—O—, and $R_4$ is methyl, ethyl, n-propyl, n-butyl, t-butyl, phenyl or benzyl.

Alternatively, for certain embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments wherein $R_1$ is —$X_1$—Y'—$R_4$, Y' is —O—, and $R_4$ is aryl which is unsubstituted or substituted by one or more substituents independently selected from the group consisting of alkyl, alkoxy, halogen, and dialkylamino. For certain of these embodiments, $R_4$ is phenyl, 2-methylphenyl, 3-methylphenyl, 4-methylphenyl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-(dimethylamino)phenyl, 3-(dimethylamino)phenyl, or 4-dimethylaminophenyl. For certain of these embodiments, $X_1$ is —$CH_2$—.

Alternatively, for certain embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments wherein $R_1$ is —$X_1$—Y'—$R_4$, Y' is —C(O)—; and $R_4$ is alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino. For certain of these embodiments, $X_1$ is a bond.

For embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments where $R_1$ is —$X_1$—Y'—X"—Y'—$R_4$, $R_1$ is —$X_1$—Y'$_a$—X"—Y'$_b$—$R_4$; Y'$_a$ is —O—; X" is arylene; Y'$_b$ is —C(O)—N($R_8$)—; $R_4$ is hydrogen, alkyl, or aryl which is unsubstituted or substituted by one or more substituents independently selected from the group consisting of alkyl, alkoxy, halogen, and dialkylamino; and $R_8$ is hydrogen or $C_{1-4}$alkyl. For certain of these embodiments, arylene is phenylene. For certain of these embodiments, $R_4$ is hydrogen. For certain of these embodiments, $R_8$ is hydrogen.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments wherein $R_5$ is present, $R_5$ is

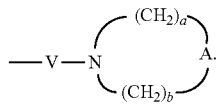

In certain of these embodiments, V is —C(O)— and A is —$CH_2$—, —O—, or —N(-Q-$R_4$)—. In certain of these embodiments, A is —$CH_2$—. Alternatively, for certain of these embodiments, V is N($R_8$)—C($R_6$)—; A is —O—; a and b are each 2 or 3; and $R_8$ is hydrogen or $C_{1-4}$ alkyl. For certain of these embodiments, $R_6$ is =O. For certain of these embodiments, a and b are each 2.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments, X is a bond.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments, X contributes one ring carbon atom.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments, X is $C_{1-2}$alkylene. In certain of these embodiments, X is methylene.

In some embodiments, particularly embodiments of Formulas I, II, II-1, IIa, II-1a, III, III-1, IV, IV-1, V, V-1, VI, VI-1, VII, VII-1, VIII, IX, IX-1, X, or X-1, or any one of the above embodiments (except where X contributes one ring carbon atom or X is methylene), X' contributes two ring carbon atoms.

For certain embodiments of the compounds of Formulas I, II, II-1, IIa, II-1a, III, III-1, IV, IV-1, V, V-1, VI, VI-1, VII, or VII-1, or any one of the above embodiments of these Formulas, the —$NH_2$ group can be replaced by an —NH-G group, as shown in the compounds of Formulas VIII, IX, and IX-1, to form prodrugs. In such embodiments, G is selected from the group consisting of: —C(O)—R", α-aminoacyl, α-aminoacyl-α-aminoacyl, —C(O)—O—R", —C(O)—N(R''')R", —C(=NY")—R", —CH(OH)—C(O)—OY", —CH(O$C_{1-4}$alkyl)$Y_0$, —$CH_2Y_1$, and —$CH(CH_3)Y_1$. For certain embodiments, G is selected from the group consisting of —C(O)—R", α-aminoacyl, α-aminoacyl-α-aminoacyl, and —C(O)—O—R". Preferably, R" and R''' are independently selected from the group consisting of $C_{1-10}$alkyl, $C_{3-7}$cycloalkyl, and benzyl, each of which may be unsubstituted or substituted by one or more substitutents selected from the group consisting of halogen, hydroxy, nitro, cyano, carboxy, $C_{1-6}$alkyl, $C_{1-4}$alkoxy, aryl, heteroaryl, aryl$C_{1-4}$alkylenyl, heteroaryl$C_{1-4}$alkylenyl, halo$C_{1-4}$alkylenyl, halo$C_{1-4}$alkoxy, —O—C(O)—$CH_3$, —C(O)—O—$CH_3$, —C(O)—$NH_2$, —O—$CH_2$—C(O)—$NH_2$, —$NH_2$, and —$S(O)_2$—$NH_2$, with the proviso that R''' can also be hydrogen. Preferably, α-aminoacyl is an acyl group derived from an amino acid selected from the group consisting of racemic, D-, and L-amino acids. Preferably, Y" is selected from the group consisting of hydrogen, $C_{1-6}$ alkyl, and benzyl. Preferably, $Y_0$ is selected from the group consisting of $C_{1-6}$ alkyl, carboxy$C_{1-6}$ alkylenyl, amino$C_{1-4}$alkylenyl, mono-N—$C_{1-6}$ alkylamino$C_{1-4}$alkylenyl, and di-N,N—$C_{1-6}$ alkylamino$C_{1-4}$alkylenyl. Preferably, $Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$alkylpiperazin-1-yl.

In some embodiments, the present invention provides a pharmaceutical composition comprising a therapeutically effective amount of a compound or salt of any one of Formulas I, II, II-1, IIa, II-1a, III, III-1, IV, IV-1, V, V-1, VI, VI-1, VII, VII-1, VIII, IX, or IX-1 or any one of the above embodiments and a pharmaceutically acceptable carrier.

In some embodiments, the present invention provides a method of inducing cytokine biosynthesis in an animal comprising administering an effective amount of a compound or salt of any one of Formulas II, IIa, III, IV, V, VI, VII, IX, or any one of the above embodiments of these Formulas or administering any one of the above pharmaceutical compositions containing a compound or salt of any one of Formulas II, IIa, III, IV, V, VI, VII, IX, or any one of the above embodiments of these Formulas to the animal.

In some embodiments, the present invention provides a method of treating a viral disease in an animal in need thereof comprising administering a therapeutically effective amount of a compound or salt of any one of Formulas II, IIa, III, IV, V, VI, VII, IX, or any one of the above embodiments of these Formulas or administering any one of the above pharmaceutical compositions containing a compound or salt of any one of Formulas II, IIa, III, IV, V, VI, VII, IX, or any one of the above embodiments of these Formulas to the animal.

In some embodiments, the present invention provides a method of treating a neoplastic disease in an animal in need thereof comprising administering a therapeutically effective amount of a compound or salt of any one of Formulas II, IIa, III, IV, V, VI, VII, IX, or any one of the above embodiments of these Formulas or administering any one of the above pharmaceutical compositions containing a compound or salt of any one of Formulas II, IIa, III, IV, V, VI, VII, IX, or any one of the above embodiments of these Formulas to the animal.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates.

For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can be prepared according to Reaction Scheme I, wherein R, $X_1$, X, and X' are as defined above; Hal is chloro, bromo, or iodo; E is carbon (imidazoquinolines) or nitrogen (imidazonaphthyridines); n is an integer from 0 to 4 (imidazoquinoline ring) or 0 to 3 (imidazonaphthyridine ring); P is a hydroxy protecting group; Boc is tert-butoxycarbonyl; and $R_{1a}$ is —$X_1$—N($R_8$)-Q-$R_4$ or —$X_1$—$R_{5a}$, wherein $R_{5a}$ is

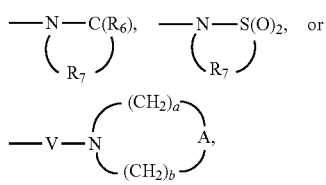

wherein V is —N($R_8$)—C($R_6$)—.

In step (1) of Reaction Scheme I, a 4-chloro-3-nitroquinoline or 4-chloro-3-nitro[1,5]naphthyridine of Formula XV is treated with compound of Formula XVI to provide a compound of Formula XVII. Compounds of Formula XVI can be prepared by conventional synthetic methods from chiral, enantiomerically pure, commercially available starting materials such as L-ornithine hydrochloride and D-serine methyl ester hydrochloride. For example, the two amino groups of L-ornithine can be protected with two different protecting groups, such as a Boc group and a benzyloxycarbonyl group (Masiukiewicz, *Org. Prep. Proced. Int.* 34, 531-537, (2002)), and then the carboxylic acid group can be reduced to a hydroxy group. The hydroxy group can then be protected. A number of suitable hydroxy protecting groups can be used; in particular, protecting groups that would survive the reduction in step (2) are preferred. Suitable protecting groups include but are not limited to silyl groups such as the tert-butyl dimethylsilyl group. One of the amino groups can then be selectively deprotected for reaction in step (1). The methods described in Pickersgill, I. F. and Rapoport, H., *J. Org. Chem.*, 65, pp. 4048-4057, (2000) can also be used to prepare compounds of Formula XVI.

The reaction in step (1) is conveniently carried out by adding the protected amino alcohol of Formula XVI to a solution of 4-chloro-3-nitroquinoline or 4-chloro-3-nitro[1,5]naphthyridine of Formula XV in a suitable solvent such as dichloromethane in the presence of a tertiary amine such as triethylamine. The reaction can be carried out at ambient temperature or at an elevated temperature such as, for example, the reflux temperature of the solvent. Many compounds of Formula XV are known or can be prepared using known synthetic methods, see for example, U.S. Pat. Nos. 4,689,338; 5,175,296; 5,367,076; 5,389,640; 6,194,425; and U.S. Patent Publication Application No. US 2004/0147543 and the documents cited therein.

In step (2) of Reaction Scheme I, a 3-nitroquinolin-4-amine or 3-nitro[1,5]naphthyridin-4-amine of Formula XVII is reduced to provide a quinoline-3,4-diamine or [1,5]naphthyridine-3,4-diamine of Formula XVIII. The reaction can be carried out by hydrogenation using a heterogeneous hydrogenation catalyst such as platinum on carbon. The hydrogenation is conveniently carried out in a Parr apparatus in a suitable solvent such as toluene, methanol, isopropanol, ethyl acetate, or acetonitrile. The reaction can be carried out at ambient temperature.

In step (3) of Reaction Scheme I, a quinoline-3,4-diamine or [1,5]naphthyridine-3,4-diamine of Formula XVIII is reacted with a carboxylic acid equivalent, which is selected such that it will provide the desired —X-Hal substituent in a 1H-imidazo[4,5-c]quinoline or 1H-imidazo[4,5-c][1,5]naphthyridine of Formula XIX. Suitable carboxylic acid equivalents include ortho esters, acid halides, imidates and imidate salts.

When the carboxylic acid equivalent is an imidate of formula Hal-$CH_2$—X—C(=NH)—O-alkyl or a salt thereof, the reaction is conveniently carried out by combining a quinoline-3,4-diamine or [1,5]naphthyridine-3,4-diamine of Formula XVIII with the imidate in a suitable solvent such 1,2-dichloroethane or chloroform. The reaction can be carried out at an elevated temperature such as 80° C. or the reflux temperature of the solvent. Some imidates of formula Hal-$CH_2$—X—C(=NH)—O-alkyl are known; others can be prepared by known methods. Ethyl chloroacetimidate hydrochloride, which can be used to provide a compound of Formula XIX in which X is a bond, is a known compound that can be prepared according to the literature procedure: Stillings, M. R. et al., *J. Med. Chem.*, 29, pp. 2280-2284 (1986).

When the carboxylic acid equivalent is an acid halide of formula Hal-$CH_2$—X—C(O)Cl or Hal-$CH_2$—X—C(O)Br, the reaction is conveniently carried out by adding the acid halide to a solution of a quinoline-3,4-diamine or [1,5]naphthyridine-3,4-diamine of Formula XVIII in a suitable solvent such as dichloromethane or 1,2-dichloroethane in the presence of a tertiary amine such as triethylamine. The reaction can be carried out at ambient temperature or at a sub-ambient temperature.

The reaction with an acid halide of formula Hal-$CH_2$—X—C(O)Cl or Hal-$CH_2$—X—C(O)Br may be carried out in two parts, which include (i) adding the acid halide to a solution of a quinoline-3,4-diamine or [1,5]naphthyridine-3,4-diamine of Formula XVIII in a suitable solvent such as dichloromethane or 1,2-dichloroethane optionally in the presence of a tertiary amine such as triethylamine to afford an amide intermediate and (ii) cyclizing to provide a 1H-imidazo[4,5-c]quinoline or 1H-imidazo[4,5-c][1,5]naphthyridine of Formula XIX. The amide intermediate from part (i) can be optionally isolated using conventional techniques. The cyclization in part (ii) may be carried out by heating the amide intermediate from part (i) in a suitable solvent such as toluene. The cyclization in part (ii) can also be carried out in the presence of a base such as triethylamine.

In step (4) of Reaction Scheme I, the hydroxy protecting group on a 1H-imidazo[4,5-c]quinoline or 1H-imidazo[4,5-c][1,5]naphthyridine of Formula XIX is removed to reveal the hydroxy group in a product of Formula XX. The deprotection reaction can be carried out using a variety of conventional methods, depending on the protecting group used. When P is a silyl group such as tert-butyldimethylsilyl, the deprotection can be carried out by adding tetrabutylammonium fluoride to a 1H-imidazo[4,5-c]quinoline or 1H-imidazo[4,5-c][1,5]naphthyridine of Formula XIX in a suitable solvent such as tetrahydrofuran (THF). The reaction can be carried out at ambient temperature or may be carried out at a sub-ambient temperature, such as −78° C., and then warmed to ambient temperature. When the reaction is carried out in dichloromethane, a product of Formula XXI is typically isolated, and the reaction shown in step (5) may be obviated.

In step (5) of Reaction Scheme I, a 1H-imidazo[4,5-c]quinoline or 1H-imidazo[4,5-c][1,5]naphthyridine of Formula XX is cyclized by an intramolecular displacement of the halogen under basic conditions. The reaction is conveniently carried out by adding a base such as potassium tert-butoxide to a solution of a compound of Formula XX in a suitable solvent such as THF. The reaction can be carried out at ambient temperature or at an elevated temperature.

In step (6) of Reaction Scheme I, a 1H-imidazo[4,5-c]quinoline or 1H-imidazo[4,5-c][1,5]naphthyridine of Formula XXI is oxidized to provide a 1H-imidazo[4,5-c]quinoline-5N-oxide or 1H-imidazo[4,5-c][1,5]naphthyridine-5N-oxide of Formula XXII using a conventional oxidizing agent capable of forming N-oxides. The reaction is conveniently carried out by adding 3-chloroperoxybenzoic acid to a solution of a compound of Formula XXI in a solvent such as chloroform or dichloromethane. The reaction can be carried out at ambient temperature.

In step (7) of Reaction Scheme I, a 1H-imidazo[4,5-c]quinoline-5N-oxide or 1H-imidazo[4,5-c][1,5]naphthyridine-5N-oxide of Formula XXII is aminated to provide a 1H-imidazo[4,5-c]quinolin-6-amine or 1H-imidazo[4,5-c][1,5]naphthyridin-6-amine of Formula XXIII, a subgenus of Formulas I, II, and IIa. Step (7) involves the activation of an N-oxide of Formula XXII by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XXII in a suitable solvent such as dichloromethane or chloroform and then adding p-toluenesulfonyl chloride. The reaction can be carried out at ambient temperature.

Alternatively, the oxidation and amination can be carried out as a one-pot procedure without isolating the N-oxide of Formula XXII by adding 3-chloroperoxybenzoic acid to a solution of a compound of Formula XXI in a solvent such as dichloromethane or chloroform and then adding ammonium hydroxide and p-toluenesulfonyl chloride.

In step (8) of Reaction Scheme I, a 1H-imidazo[4,5-c]quinolin-6-amine or 1H-imidazo[4,5-c][1,5]naphthyridin-6-amine of Formula XXIII is treated with acid to effect a removal of the Boc group to provide a compound of Formula XXIV. The reaction is conveniently carried out by treating the compound of Formula XXIII with hydrogen chloride in a suitable solvent such as ethanol. The reaction can be carried out at ambient temperature or at an elevated temperature, such as the reflux temperature of the solvent.

In step (9) of Reaction Scheme I, the amino group of a compound of Formula XXIV, revealed in step (8), or a salt thereof is converted to an amide, sulfonamide, sulfamide, or urea of Formula XXV using conventional methods. For example, a compound of Formula XXIV or a salt thereof can react with an acid chloride of Formula $R_4C(O)Cl$ to provide a compound of Formula XXV in which $R_{1a}$ is —$X_1$—$N(R_8)$-Q-$R_4$, and Q is —C(O)—. In addition, a compound of Formula XXIV can react with sulfonyl chloride of Formula $R_4S(O)_2Cl$ or a sulfonic anhydride of Formula $(R_4S(O)_2)_2O$ to provide a compound of Formula XXV in which $R_{1a}$ is —$X_1$—$N(R_8)$-Q-$R_4$ and Q is —$S(O)_2$—. Numerous acid chlorides of Formula $R_4C(O)Cl$, sulfonyl chlorides of Formula $R_4S(O)_2Cl$, and sulfonic anhydrides of Formula $(R_4S(O)_2)_2O$ are commercially available; others can be readily prepared using known synthetic methods. The reaction is conveniently carried out by adding the acid chloride of Formula $R_4C(O)Cl$, sulfonyl chloride of Formula $R_4S(O)_2Cl$, or sulfonic anhydride of Formula $(R_4S(O)_2)_2O$ to a solution of the compound of Formula XXIV in a suitable solvent such as chloroform, dichloromethane, N,N-dimethylformamide (DMF), or N,N-dimethylacetamide (DMA). Optionally a base such as triethylamine, N,N-diisopropylethylamine, 1,8-diazabicyclo[5.4.0]undec-7-ene (DBU), or combinations thereof can be added. The reaction can be carried out at ambient temperature or a sub-ambient temperature such as 0° C.

Ureas of Formula XXV, where $R_{1a}$ is —$X_1$—$N(R_8)$-Q-$R_4$, Q is —C(O)—$N(R_8)$—, and $R_8$ is hydrogen, can be prepared by reacting a compound of Formula XXIV or a salt thereof with isocyanates of Formula $R_4N$=C=O, Numerous isocyanates of Formula $R_4N$=C=O are commercially available; others can be readily prepared using known synthetic methods. The reaction can be conveniently carried out by adding the isocyanate of Formula $R_4N$=C=O to a solution of the compound of Formula XXIV in a suitable solvent such as DMF, chloroform, dichloromethane, or DMA. Optionally a base such as triethylamine, N,N-diisopropylethylamine, DBU, or combinations thereof can be added. The reaction can be carried out at ambient temperature or a sub-ambient temperature such as 0° C. Alternatively, a compound of Formula XXIV can be treated with an isocyanate of Formula $R_4(CO)N$=C=O, a thioisocyanate of Formula $R_4N$=C=S, a sulfonyl isocyanate of Formula $R_4S(O)_2N$=C=O, or a carbamoyl chloride of Formula $R_4N$—$(R_8)$—C(O)Cl to provide a compound of Formula XXV, where $R_{1a}$ is —$X_1$—$N(R_8)$-Q-$R_4$ and Q is —C(O)—$N(R_8)$—C(O)—, —C(S)—$N(R_8)$—, —C(O)—$N(R_8)$—$S(O)_2$—, or —C(O)—$N(R_8)$—, respectively. Alternatively, a compound of Formula XXIV can be treated with a carbamoyl chloride of Formula

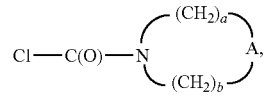

to provide a compound of Formula XXV, in which $R_{1a}$ is —$X_1$—$R_{5a}$, wherein $R_{5a}$ is

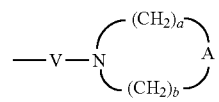

and V is —$N(R_8)$—C(O)—.

Sulfamides of Formula XXV, where Y is —$S(O)_2$—$N(R_8)$—, can be prepared by reacting a compound or salt of Formula XXIV with sulfuryl chloride to generate a sulfamoyl chloride in situ, and then reacting the sulfamoyl chloride with an amine of formula $HN(R_8)R_4$. Alternatively, sulfamides of Formula XXV can be prepared by reacting a compound of Formula XXIV with a sulfamoyl chloride of formula $R_4(R_8)N$—$S(O)_2Cl$. Many sulfonyl chlorides of Formula $R_4S(O)_2Cl$ and amines of Formula $HN(R_8)R_4$, and some sulfamoyl chlorides of formula $R_4(R_8)N$—$S(O)_2Cl$ are commercially available; others can be prepared using known synthetic methods.

In another example shown in step (9) of Reaction Scheme I, a compound or salt of Formula XXIV, wherein $R_8$ is hydrogen, is reacted with a chloroalkanesulfonyl chloride of Formula $Cl$—$R_7$—$S(O)_2Cl$ or a chloroalkanoyl chloride compound of formula $Cl$—$R_7$—C(O)Cl to provide a compound of Formula XXV, wherein $R_{1a}$ is —$X_1$—$R_{5a}$ and $R_{5a}$ is a ring having the structure

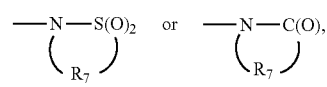

respectively. The reaction is preferably carried out by adding the chloroalkanesulfonyl chloride or chloroalkanoyl chloride to a solution of a compound of Formula XXIV in a suitable solvent such as dichloromethane in the presence of a base such as triethylamine or N,N-diisopropylethylamine. The intermediate chloroalkanesulfonamide or chloroalkanamide may optionally be isolated before treatment with a stronger base such as DBU at ambient temperature. If the intermediate chloroalkanesulfonamide or chloroalkanamide is isolated, the reaction with DBU can be carried out in a suitable solvent such as DMF.

Reaction Scheme I

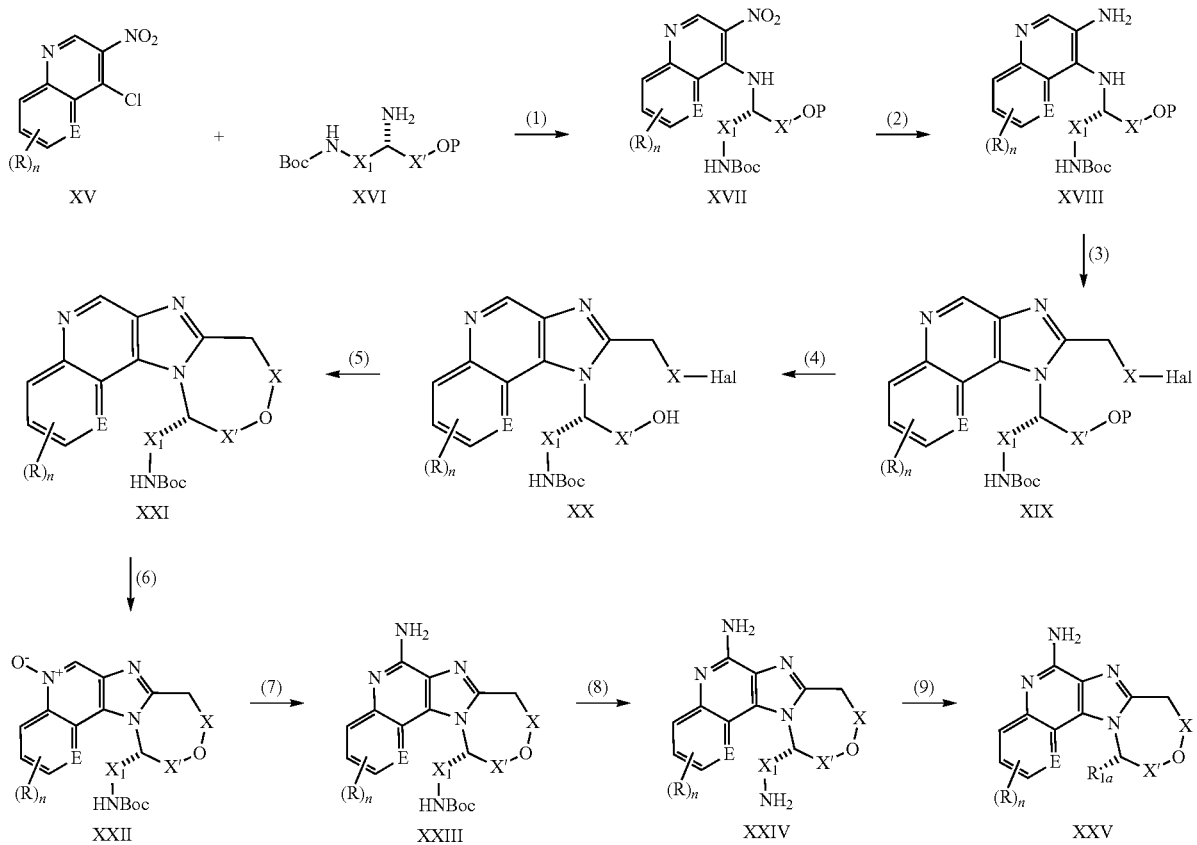

Compounds of the invention can be prepared according to Reaction Scheme II, wherein R, $R_1$, $R_4$, $X_1$, X, and X' are as defined above; Hal is chloro, bromo, or iodo; E is carbon (imidazoquinolines) or nitrogen (imidazonaphthyridines); n is an integer from 0 to 4 (imidazoquinoline ring) or 0 to 3 (imidazonaphthyridine ring); $Y'_a$ is defined below in step (9); and P and $P^2$ are hydroxy protecting groups. In step (1) of Reaction Scheme I, a 4-chloro-3-nitroquinoline or 4-chloro-3-nitro[1,5]naphthyridine of Formula XV is treated with a protected amino alcohol of Formula XXVIII to provide a compound of Formula XXIX. Protected amino alcohols of Formula XXVIII can be prepared by a variety of known synthetic methods including the methods shown in steps (i) and (ii) of Reaction Scheme II. In step (i) of Reaction Scheme II, a chiral, enantiomerically pure ester of Formula XXVI is reduced to an alcohol of Formula XXVII. Esters of Formula XXVI are available from the literature method, Jurczak, J. et al., *Tetrahedron*, 48, pp. 4231-4238, (1992). The reduction in step (i) can be effected with lithium aluminum hydride in a suitable solvent such as diethyl ether at a sub-ambient temperature or at ambient temperature. In step (ii) of Reaction Scheme II, the secondary amino group in a compound of Formula XXVII is first protected with a Boc group, the hydroxy group is protected with a suitable protecting group, for example, a benzyl group or acetyl group using methods well-known to one of skill in the art, and then the Boc group is removed to reveal the secondary amino group. Other methods are available for preparing compounds of Formula XXVIII; for example, see the methods described in Williams, L. et al., *Tetrahedron*, 52, pp. 11673-11694, (1996) and Genevois-Borella, A. et al., *Tetrahedron Lett.*, 31, pp. 4879-4882 (1990). The reaction in step (1) of Reaction Scheme II is conveniently carried out under the conditions described in step (1) of Reaction Scheme I.

In steps (2) and (3) of Reaction Scheme II, a 3-nitroquinolin-4-amine or 3-nitro[1,5]naphthyridin-4-amine of Formula XXIX is first reduced to a quinoline-3,4-diamine or [1,5]naphthyridine-3,4-diamine of Formula XXX, which is then treated with a halogen-substituted carboxylic acid equivalent to provide a 1H-imidazo[4,5-c]quinoline or 1H-imidazo[4,5-c][1,5]naphthyridine of Formula XXXI. Steps (2) and (3) of Reaction Scheme II can be carried out according to the methods described in steps (2) and (3) of Reaction Scheme I.

In step (4) of Reaction Scheme II, the hydroxy protecting group, P, on a 1H-imidazo[4,5-c]quinoline or 1H-imidazo[4,5-c][1,5]naphthyridine of Formula XXXI is removed to reveal the hydroxy group in a product of Formula XXXII. The deprotection reaction can be carried out according to the methods described in step (4) of Reaction Scheme I to provide a product of Formula XXXII or XXXIII.

In step (5) of Reaction Scheme II, a 1H-imidazo[4,5-c]quinoline or 1H-imidazo[4,5-c][1,5]naphthyridine of Formula XXXII is cyclized by an intramolecular displacement of the halogen under basic conditions. The reaction can be carried out as described in step (5) of Reaction Scheme I.

In steps (6) and (7) of Reaction Scheme II, a compound of Formula XXXIII is first oxidized to a 1H-imidazo[4,5-c]quinoline-5N-oxide or 1H-imidazo[4,5-c][1,5]naphthyridine-5N-oxide of Formula XXXIV, which is then aminated to provide a 1H-imidazo[4,5-c]quinolin-6-amine or 1H-imidazo[4,5-c][1,5]naphthyridin-6-amine of Formula XXXV. Steps (6) and (7) of Reaction Scheme II can be carried out as described in steps (6) and (7) of Reaction Scheme I. The hydroxy-protecting group, $P^2$, may be removed under the amination reaction conditions of step (7) or may need to be removed in a subsequent step depending on the nature of the $P^2$ group. If $P^2$ is a acetyl group, the deprotection would typically occur under the conditions of the amination reaction.

In step (8) of Reaction Scheme II, a hydroxy-substituted compound of Formula XXXV is chlorinated to provide a chloro-substituted compound of Formula XXXVI. Conventional chlorinating reagents can be used. The reaction is conveniently carried out by combining a compound of Formula XXXV with thionyl chloride in a suitable solvent such as dichloromethane and heating. Alternatively, the reaction may be run neat.

In step (9) of Reaction Scheme II, the chloro group on a compound of Formula XXXVI can be displaced by a thiol under basic conditions to provide a compound of Formula XXXVII where —$Y'_a$— is —S—. The reaction is conveniently carried out by adding a thiol to a solution of a compound of Formula XXXVI in the presence of a base such as potassium tert-butoxide in a suitable solvent such as DMF. A compound of Formula XXXVII where —$Y'_a$— is —S— can then be oxidized to a compound of Formula XXXVII where —$Y'_a$— is —$S(O)_2$— using conventional oxidizing agents. The reaction is conveniently carried out by adding peracetic acid to the compound of Formula XXXVII where —$Y'_a$— is —S— in a suitable solvent. The conversion of a compound of Formula XXXVI to a compound of Formula XXXVII where —$Y'_a$— is —$S(O)_2$— can conveniently be carried out in one pot without isolating the thioether from the reaction mixture.

The chloro group on a compound of Formula XXXVI can also be displaced by an amine of Formula

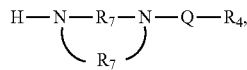

several of which are commercially available. Other amines of this formula can be prepared by conventional methods. The reaction is conveniently carried out by combining a compound of Formula XXXVI the amine in the presence of a base such as potassium carbonate and in a suitable solvent such as DMF. Catalytic sodium iodide can optionally be added. The reaction can be carried out at an elevated temperature, for example a temperature not lower than 45° C. and not higher than 110° C. These reaction conditions can also be used employing a variety of secondary amines to provide compounds of Formula XXXVII wherein —$Y'_a$— is —$N(R_8)$— or a variety of substituted phenols to provide compounds of Formula XXXVII wherein —$Y'_a$— is —O— and $R_4$ is a substituted phenyl group.

In step (10) of Reaction Scheme II, a hydroxy-substituted compound of Formula XXXV is oxidized to a carboxylic acid of Formula XXXVIII using conventional methods. The oxidation can be carried out with, for example, Jones reagent.

The carboxylic acid of Formula XXXVIII can then be converted to an ester or an amide in step (12) using known methods to provide compounds of Formula XXXIX wherein $R_1$ is —$X_1$—$C(R_6)$—O—$R_4$, —$X_1$—$C(R_6)$—$N(R_8)$—$R_4$ or —$X_1$—$R_5$, wherein $R_5$ is

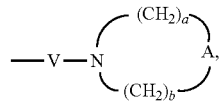

and V is —$C(R_6)$—. Step (12) of Reaction Scheme II can be carried out in two parts by first converting a carboxylic acid of Formula XXXVIII to an acid chloride using conventional methods and then treated with an amine or alcohol to provide an amide or ester. The conversion of the carboxylic acid to an acid chloride is conveniently carried out by slowly adding oxalyl chloride to a solution of the carboxylic acid in a suitable solvent such as dichloromethane. The reaction can be carried out at a sub-ambient temperature, such as 0° C. The resulting acid chloride can then be treated with an amine, for example, of Formula $HN(R_8)(R_4)$ or

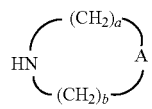

in a suitable solvent such as dichloromethane. Numerous amines of these formulas are commercially available; others can be prepared by known synthetic methods. The reaction can be run at ambient temperature. Alternatively a carboxylic acid of Formula XXXVIII can be converted in step (12) to a methyl ester using conventional methods and subsequently converted to an amide by heating the methyl ester in the presence of an amine of Formula $HN(R_1')(R_1'')$ or

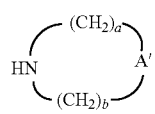

at an elevated temperature such as 90° C.-120° C. The reaction is conveniently carried out in a high-pressure vessel and can be run neat or in a suitable solvent such as THF.

Step (11) of Reaction Scheme II can be used to convert the hydroxy group in a compound of Formula XXXV into a variety of other functional groups. For example, hydroxy-substituted compound of Formula XXXV can be treated with N-hydroxyphthalimide under Mitsunobu reaction conditions to provide an N-phthalimide-protected hydroxylamine. The reaction is conveniently carried out by adding triphenylphosphine and N-hydroxyphthalimide to a solution of the alcohol of Formula XXXV in a suitable solvent such as THF and then slowly adding diisopropyl azodicarboxylate. The reaction can be carried out at ambient temperature or at an elevated temperature, such as 60° C. The phthalimide group can then be removed from the resulting N-phthalimide-protected hydroxylamine by treatment with hydrazine at ambient temperature in a suitable solvent such as ethanol. The resulting hydroxylamine can then be treated with one of numerous commercially available aldehydes or ketones in a suitable solvent such as methanol to provide a compound of Formula XXXIX wherein $R_1$ is —$X_1$—Y'—$R_4$ or —$X_1$—$R_5$, where Y' is —O—N=C($R_4$)—, $R_5$ is

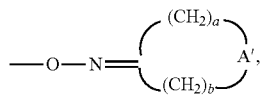

and $R_4$, a, b, and A' are as defined above. Alternatively, the hydroxylamine prepared after the hydrazine deprotection may be treated with one of numerous acid chlorides, sulfonyl chlorides, isocyanates, carbamoyl chlorides, or sulfamoyl chlorides as described in step (9) of Reaction Scheme I to provide a compound Formula XXXIX wherein $R_1$ is —$X_1$—Y'—$R_4$ where Y is —O—NH-Q-, and Q and $R_4$ are as defined above.

In another example, a hydroxy-substituted compound of Formula XXXV can be oxidized under Swern conditions to an aldehyde-substituted compound which can optionally be treated with a Grignard reagent of Formula $R_4$—Mg-Halide under conventional Grignard conditions to provide a secondary alcohol. The secondary alcohol can then be oxidized under Swern conditions to provide a ketone, which is a compound of Formula XXXIX wherein $R_1$ is —$X_1$—Y'—$R_4$ where Y' is —C(O)—, and $R_4$ is as defined above. The ketone can then be converted to an oxime by adding an aqueous solution of a hydroxylamine salt of Formula $NH_2OR_8$.HCl to a solution of the ketone in a suitable solvent such as methanol or ethanol and then adding a base such as sodium hydroxide and heating at an elevated temperature to provide a compound of the invention, wherein $R_1$ is —$X_1$—Y'—$R_4$ where Y' is —C(=N—$OR_8$)—, and $R_4$ and $R_8$ are as defined above. The oxime so prepared may be reduced with sodium cyanoborohydride in a mixture of ethanol or methanol in acetic acid to provide a hydroxylamine, which may be treated with one of numerous acid chlorides, sulfonyl chlorides, isocyanates, carbamoyl chlorides, or sulfamoyl chlorides as described in step (9) of Reaction Scheme I to provide a compound of the invention wherein $R_1$ is —$X_1$—Y'—$R_4$ where Y is —CH(—N—($OR_8$)-Q-$R_4$)—, and Q, $R_4$, and $R_8$ are as defined above.

Reaction Scheme II

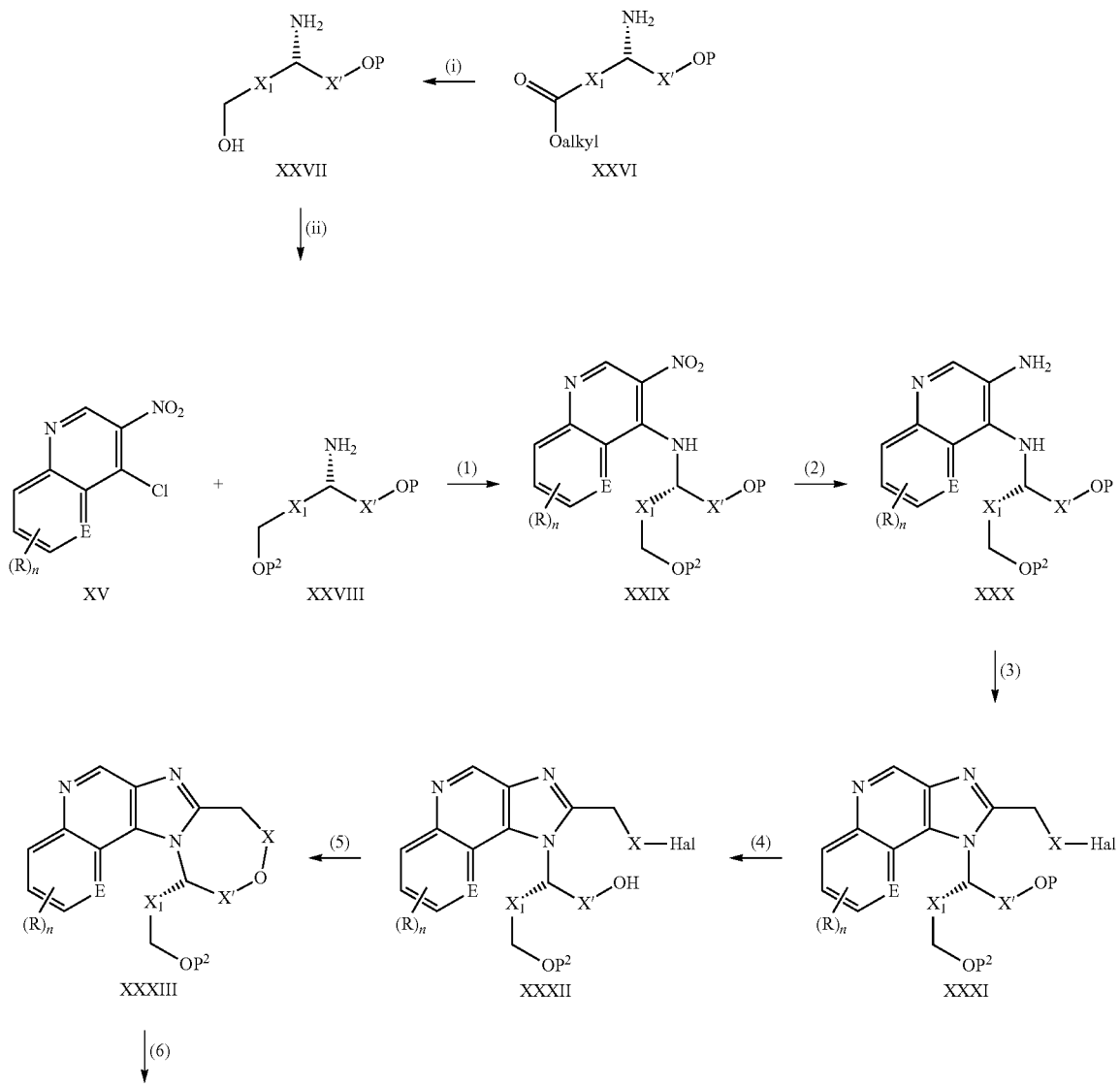

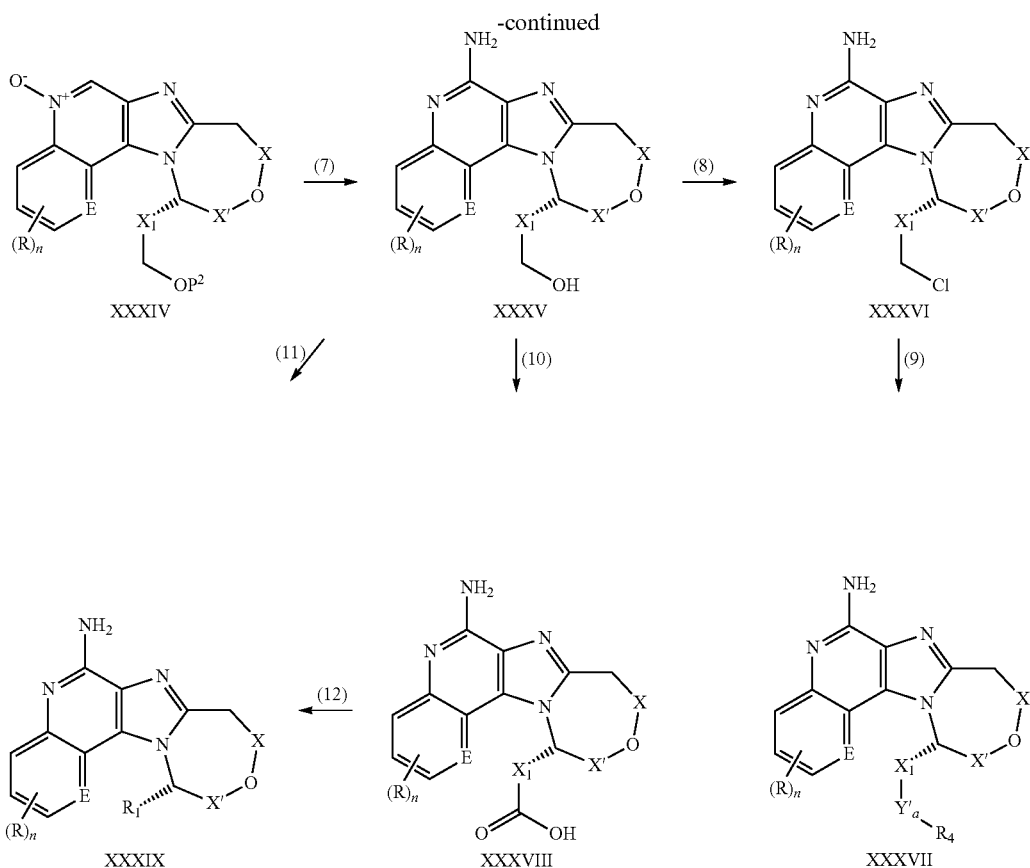

Compounds of the invention can also be prepared according to Reaction Scheme III, wherein R, $R_{1a}$, $R_2$, X, X', $X_1$, Y, Boc, and Hal, are as defined above; E and n are as defined in Reaction Scheme I and II.

In step (1) of Reaction Scheme III, a 4-chloro-3-nitroquinoline or 4-chloro-3-nitro[1,5]naphthyridine of Formula XV is treated with a Boc-protected diamine of Formula XL to provide a compound of Formula XLI. Boc-protected diamines of Formula XL are available from the corresponding deprotected diamines, which are readily synthesized from amino alcohols of Formula XVI. For example, the secondary amino group in a compound of Formula XVI can be protected with a suitable protecting group, such as a benzyloxy group, using conventional methods. The hydroxy-group can then be revealed by removal of the protecting group, P, and then converted into a leaving group such as a methanesulfonate. The methanesulfonate group can then be displaced with sodium azide, and the resulting azido substituted compound can be reduced to an amine. The amine can then be treated according to one of the methods described in step (9) of Reaction Scheme I to install a —Y—$R_2$ group. The secondary amino group can then be deprotected according to conventional methods. The reaction in step (1) of Reaction Scheme III is conveniently carried out under the conditions described in step (1) of Reaction Scheme I.

In steps (2) and (3) of Reaction Scheme III, a 3-nitroquinolin-4-amine or 3-nitro[1,5]naphthyridin-4-amine of Formula XLI is first reduced to a quinoline-3,4-diamine or [1,5]naphthyridine-3,4-diamine of Formula XLII, which is then treated with a halogen-substituted carboxylic acid equivalent to provide a 1H-imidazo[4,5-c]quinoline or 1H-imidazo[4,5-c][1,5]naphthyridine of Formula XLIII. Steps (2) and (3) of Reaction Scheme III can be carried out according to the methods described in steps (2) and (3) of Reaction Scheme I.

In step (4) of Reaction Scheme III, a 1H-imidazo[4,5-c]quinoline or 1H-imidazo[4,5-c][1,5]naphthyridine of Formula XLIII is cyclized by an intramolecular displacement of the halogen under basic conditions. The reaction is conveniently carried out by treating a compound of Formula XLIII with DBU in a suitable solvent such as dichloromethane at ambient temperature.

In steps (5) and (6) of Reaction Scheme III, a compound of Formula XLIV is first oxidized to a 1H-imidazo[4,5-c]quinoline-5N-oxide or 1H-imidazo[4,5-c][1,5]naphthyridine-5N-oxide of Formula XLV, which is then aminated to provide a 1H-imidazo[4,5-c]quinolin-6-amine or 1H-imidazo[4,5-c][1,5]naphthyridin-6-amine of Formula XLVI. Steps (5) and (6) of Reaction Scheme III can be carried out as described in steps (7) and (8) of Reaction Scheme I.

In step (7) of Reaction Scheme III, a 1H-imidazo[4,5-c]quinoline or 1H-imidazo[4,5-c][1,5]naphthyridine of Formula XLVI treated with acid to effect a removal of the Boc group and an intramolecular displacement of the halogen by the amino group to provide a compound of Formula XLVII. The reaction is conveniently carried out by treating the compound of Formula XLVI with hydrogen chloride in a suitable solvent such as ethanol. The reaction can be carried out at ambient temperature or at an elevated temperature such as the reflux temperature of the solvent.

In step (8) of Reaction Scheme III, the primary amine of a compound of Formula XLVII or a salt thereof is converted to an amide, sulfonamide, sulfamide, or urea of Formula XLVIII using one of the various methods described in step (9) of Reaction Scheme I.

Reaction Scheme III

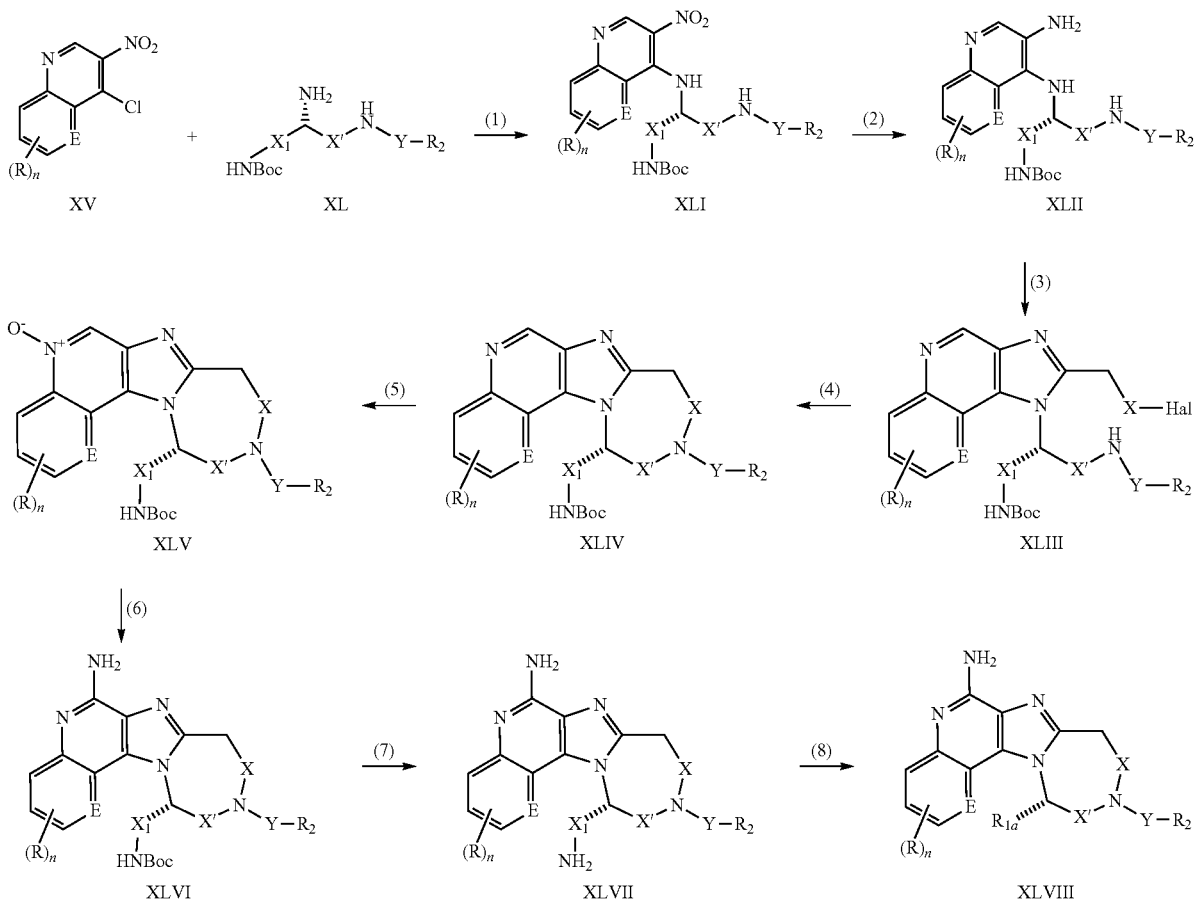

For some embodiments, compounds of the invention are prepared according to Reaction Scheme IV, wherein X, X', Z, R and $R_1$ are as defined above; E is as defined in Reaction Scheme I and II, hal is bromo or iodo; n is 0 or 1; $R_{1a}$ is $-Z'-R_{4b}$, $-Z'-X''_a-R_4$, $-Z'-X''_b-R_4$, or $-Z'-X''_b-R_5$; where Z' is a bond; $X''_a$ is alkenylene; $X''_b$ is arylene, heteroarylene, and alkenylene interrupted or terminated by arylene or heteroarylene; $R_{4b}$ is aryl or heteroaryl where the aryl or heteroaryl groups can be unsubstituted or substituted as defined in $R_4$ above; and $R_4$, $R_5$, and Y' are as defined above. Compounds of Formula XLIX can be prepared by the methods shown in Reaction Scheme I, II, or III beginning with a compound of Formula XV wherein n is other than 0 and one of the R groups present is hal.

In Reaction Scheme IV, a 1H-imidazo[4,5-c]quinolin-6-amine or 1H-imidazo[4,5-c][1,5]naphthyridin-6-amine of Formula XLIX is coupled with a boronic acid of Formula $R_{3a}-B(OH)_2$, an anhydride thereof, or a boronic acid ester of Formula $R_{3a}-B(O-alkyl)_2$ to provide a 1H-imidazo[4,5-c]quinolin-6-amine or 1H-imidazo[4,5-c][1,5]naphthyridin-6-amine of Formula L, which is a subgenus of Formulas I, II, and IIa. The Suzuki coupling is carried out by combining a compound of Formula XLIX with a boronic acid or an ester or anhydride thereof in the presence of palladium (II) acetate, triphenylphosphine, and a base such as sodium carbonate in a suitable solvent such as n-propanol or solvent mixture such as n-propanol/water. The reaction can be carried out at an elevated temperature (e.g., 80-100° C.). Many boronic acids of Formula $R_{3a}-B(OH)_2$, anhydrides thereof, and boronic acid esters of Formula $R_{3a}-B(O-alkyl)_2$ are commercially available; others can be readily prepared using known synthetic methods. See, for example, Li, W. et al, *J. Org. Chem.*, 67, 5394-5397 (2002).

Other coupling reactions such as the Heck reaction, the Stille coupling, and the Sonogashira coupling can be used to prepare compounds of Formula L. Also, compounds of Formula L, wherein $R_{3a}$ is $-Z'-X''_a-R_4$, $-Z'-X''_b-Y'-R_4$, or $-Z'-X''_b-R_5$ in which $X''_b$ is alkenylene interrupted or terminated by arylene or heteroarylene, can undergo reduction of the $X''_a$ or $X''_b$ alkenylene group. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof.

Reaction Scheme IV

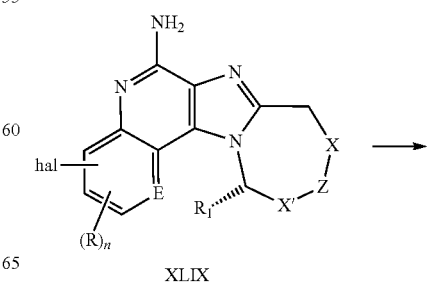

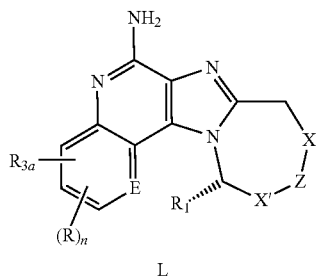

Compounds of the invention can be prepared according to Reaction Scheme V where R, $R_{1a}$, P, X, X', $X_1$, Hal, and Boc are as defined above; n is 0 or 1; $R_{3b}$ is —$R_4$, —X"—$R_4$, —X"—Y'—$R_4$, —X"—Y'—X"—Y'—$R_4$, or —X"—$R_5$, where $R_4$, V, Y', and $R_5$ are as defined above. In step (1) of Reaction Scheme V, a benzyloxyaniline or benzyloxyaminopyridine of Formula LI is treated with the condensation product generated from 2,2-dimethyl-1,3-dioxane-4,6-dione (Meldrum's acid) and triethyl orthoformate to provide an imine of Formula LII. The reaction is conveniently carried out by adding a solution of a compound of Formula LI to a heated mixture of Meldrum's acid and triethyl orthoformate and heating the reaction at an elevated temperature such as 45° C. Many anilines and aminopyridines of Formula LI are commercially available; others can be prepared by known synthetic methods. For example, benzyloxypyridines of Formula LI can be prepared using the method of Holladay et al., *Biorg. Med. Chem. Lett.*, 8, pp. 2797-2802, (1998).

In step (2) of Reaction Scheme V, an imine of Formula LII undergoes thermolysis and cyclization to provide a compound of Formula LIII. The reaction is conveniently carried out in a medium such as DOWTHERM A heat transfer fluid at a temperature in the range of 200 and 250° C.

In step (3) of Reaction Scheme V, a compound of Formula LIII is nitrated under conventional nitration conditions to provide a benzyloxy-3-nitroquinolin-4-ol of Formula LIV. The reaction is conveniently carried out by adding nitric acid to the compound of Formula LIII in a suitable solvent such as propionic acid and heating the mixture at an elevated temperature such as 125° C.

In step (4) of Reaction Scheme V, a benzyloxy-3-nitroquinolin-4-ol or benzyloxy-3-nitro[1,5]naphthyridin-4-ol of Formula LIV is chlorinated using conventional chlorination chemistry to provide a benzyloxy-4-chloro-3-nitroquinoline or benzyloxy-4-chloro-3-nitro[1,5]naphthyridine of Formula LV. The reaction is conveniently carried out by treating the compound of Formula LIV with phosphorous oxychloride in a suitable solvent such as DMF. The reaction can be carried out at an elevated temperature such as 100° C.

In step (5) of Reaction Scheme V, a benzyloxy-4-chloro-3-nitroquinoline or benzyloxy-4-chloro-3-nitro[1,5]naphthyridine of Formula LV is treated with an amino alcohol of Formula XVI to provide a benzyloxy-3-nitroquinolin-4-amine or benzyloxy-3-nitro[1,5]naphthyridin-4-amine of Formula LVI. The reaction is conveniently carried out according to the methods described in step (1) of Reaction Scheme I.

In steps (6) and (7) of Reaction Scheme V, a benzyloxy-3-nitroquinolin-4-amine or benzyloxy-3-nitro[1,5]naphthyridin-4-amine of Formula LVI is reduced to provide a benzyloxyquinoline-3,4-diamine or benzyloxy[1,5]naphthyridine-3,4-diamine of Formula LVII, which is then is treated with a halogen-substituted carboxylic acid equivalent to provide a benzyloxy-1H-imidazo[4,5-c]quinoline or benzyloxy-1H-imidazo[4,5-c][1,5]naphthyridine of Formula LVIII. Steps (6) and (7) of Reaction Scheme V can be carried out according to the methods described in steps (2) and (3) of Reaction Scheme I.

In step (8) of Reaction Scheme V, the hydroxy group of a benzyloxy-1H-imidazo[4,5-c]quinoline or a benzyloxy-1H-imidazo[4,5-c][1,5]naphthyridine of Formula LVIII is deprotected to provide a compound of Formula LIX or LX. The deprotection can be carried out as described in step (4) of Reaction Scheme I. Step (9) of Reaction Scheme V can be used to cyclize a compound of Formula LIX according to the method described in step (5) of Reaction Scheme I.

In steps (10) and (11) of Reaction Scheme V, the Boc group of a compound of Formula LX is first removed to provide an amino-substituted compound of Formula LXI, which can then be converted to an amide, sulfonamide, sulfamide, or urea of Formula LXII. Steps (10) and (11) of Reaction Scheme V can be carried out according to the methods described in steps (8) and (9) of Reaction Scheme I.

In step (12) of Reaction Scheme V, the benzyl group of a benzyloxy-1H-imidazo[4,5-c]quinoline or benzyloxy-1H-imidazo[4,5-c][1,5]naphthyridine of Formula LXII is cleaved to provide a 1H-imidazo[4,5-c]quinolinol or 1H-imidazo[4,5-c][1,5]naphthyridinol of Formula LXIII. The cleavage is conveniently carried out on a Parr apparatus under hydrogenolysis conditions using a suitable heterogeneous catalyst such as palladium on carbon in a solvent such as ethanol. Alternatively, the reaction can be carried out by transfer hydrogenation in the presence of a suitable hydrogenation catalyst. The transfer hydrogenation is conveniently carried out by adding ammonium formate to a solution of a compound of Formula LXII in a suitable solvent such as ethanol in the presence of a catalyst such as palladium on carbon. The reaction is carried out at an elevated temperature, for example, the reflux temperature of the solvent.

In step (13) of Reaction Scheme V a 1H-imidazo[4,5-c]quinolinol or 1H-imidazo[4,5-c][1,5]naphthyridinol of Formula LXIII is converted to an ether-substituted 1H-imidazo[4,5-c]quinoline or 1H-imidazo[4,5-c][1,5]naphthyridine of Formula LXIV using a Williamson-type ether synthesis. The reaction is effected by treating a compound of Formula LXIII with an alkyl halide of Formula Halide-$R_4$, Halide-X"—Y'—$R_4$, or Halide-X"—$R_5$ in the presence of a base. The reaction is conveniently carried out by combining the alkyl halide with a compound of Formula LXIII in a solvent such as DMF in the presence of a suitable base such as cesium carbonate. The reaction can be carried out at ambient temperature or at an elevated temperature, for example 65° C. or 85° C. Alternatively, the reaction can be carried out by treating a solution of a compound of Formula LXIII in a solvent such as DMF with sodium hydride and then adding a reagent of Formula Halide-$R_4$, Halide-X"—Y'—$R_4$, or Halide-X"—$R_5$.

Numerous reagents of Formulas Halide-$R_4$ and Halide-X"—Y'—$R_4$ are commercially available, for example, substituted benzyl bromides and chlorides, substituted or unsubstituted alkyl or arylalkylenyl bromides and chlorides, substituted fluorobenzenes, bromo-substituted ketones, esters, and heterocycles. Other reagents of Formulas Halide-$R_4$, Halide-X"—Y'—$R_4$, and Halide-X"—$R_5$ can be prepared using conventional synthetic methods; for example, a bromo-substituted acid halide of Formula ClC(O)—X"—Br can be treated with a secondary amine in a suitable solvent such as dichloromethane to provide a variety of bromo-substituted amides of Formula Br—X"—C(O)—N($R_8$)—$R_4$ or

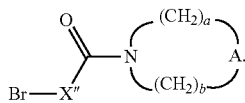

The reaction can be run at a sub-ambient temperature such as −25° C. Also, compounds of Formula I-X"—N(R$_8$)-Boc are readily prepared in two steps from amino alcohols of Formula HO—X"—N(R$_8$)H by first protecting the amine with a Boc group and then converting the hydroxy group to an iodo group. Both reactions can be carried out using conventional methods. The compound of Formula LXIV wherein R$_{3b}$ is —X"—Y'—R$_4$, wherein Y' is —N(R$_8$)—C(O)—O— and R$_4$ is tert-butyl thus prepared can be converted into a compound wherein Y' is —N(R$_8$)-Q- and Q and R$_4$ are as defined above using one of the methods described in step (9) of Reaction Scheme I.

Step (13) of Reaction Scheme V can alternatively be carried out by treating a compound of Formula LXIII with an alcohol of Formula HO—X"—Y'—R$_4$, HO—X"—R$_5$, or HO—R$_4$ under Mitsunobu reaction conditions. Numerous alcohols of these formulas are commercially available; for example, 1-(3-hydroxypropyl)pyrrolidin-2-one, 1-(2-hydroxyethyl)pyrrolidin-2-one, and tert-butyl 4-hydroxypiperidine-1-carboxylate. Others can be prepared using conventional synthetic methods. The reaction is conveniently carried out by out by adding triphenylphosphine and an alcohol of Formula HO—X"—Y'—R$_4$, HO—X"—R$_5$, or HO—R$_4$ to a solution of a compound of Formula LXIII in a suitable solvent such as THF and then slowly adding diisopropyl azodicarboxylate or diethyl azodicarboxylate. The reaction can be carried out at ambient temperature or at a sub-ambient temperature, such as 0° C.

In steps (14) and (15) of Reaction Scheme V, an ether-substituted compound of Formula LXIV is first oxidized to a 5N-oxide of Formula LXV, which is then aminated to provide a 1H-imidazo[4,5-c]quinolin-6-amine or 1H-imidazo[4,5-c][1,5]naphthyridin-6-amine of Formula LXVI, a subgenus of Formulas I, II, and IIa. Steps (14) and (15) of Reaction Scheme V can be carried out as described in steps (6) and (7) of Reaction Scheme I.

Isomers of the compound of Formula LI or Formula LIII, wherein E is nitrogen, can also be synthesized and can be used to prepare compounds of the invention according to the methods of Reaction Scheme V.

Reaction Scheme V
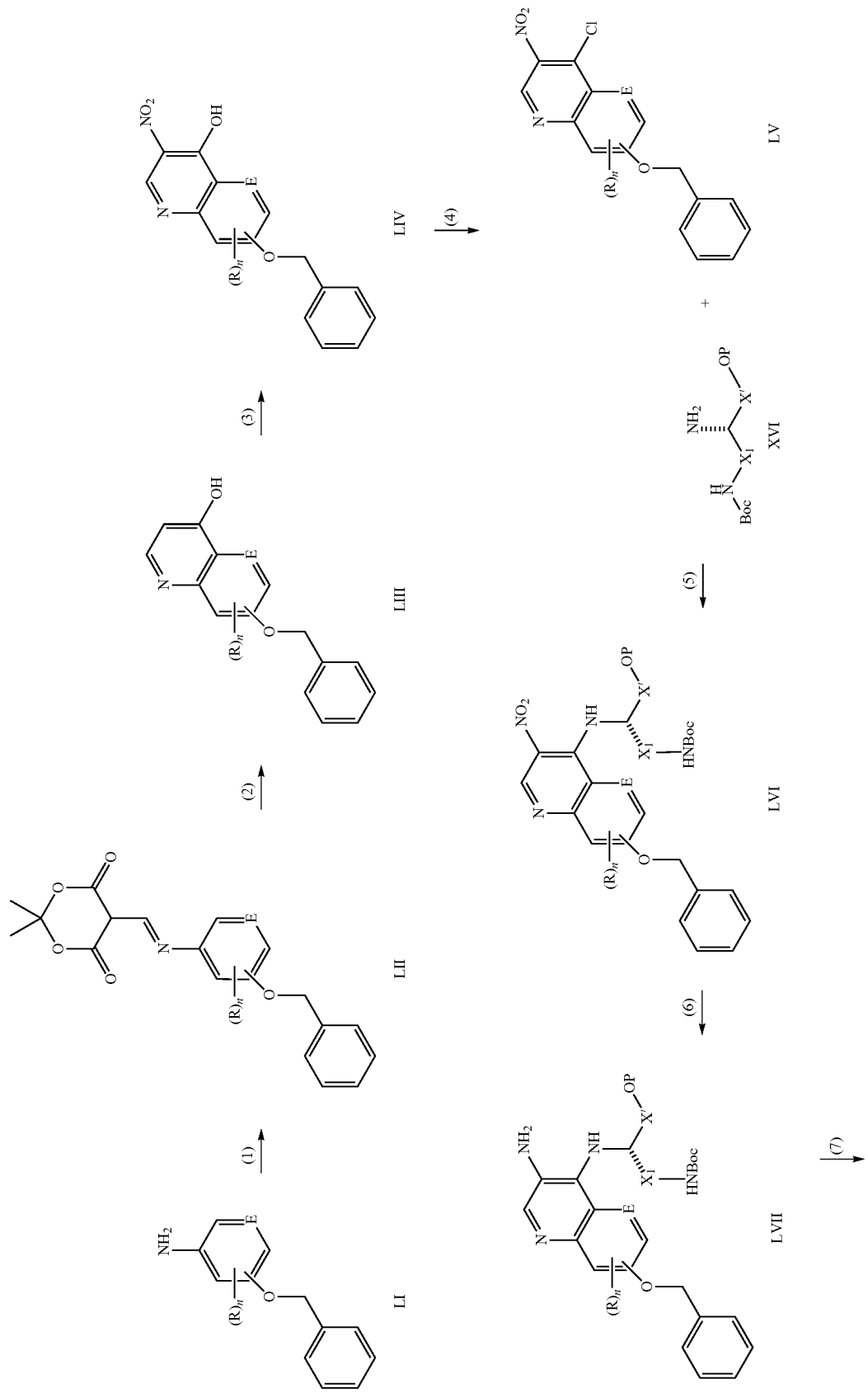

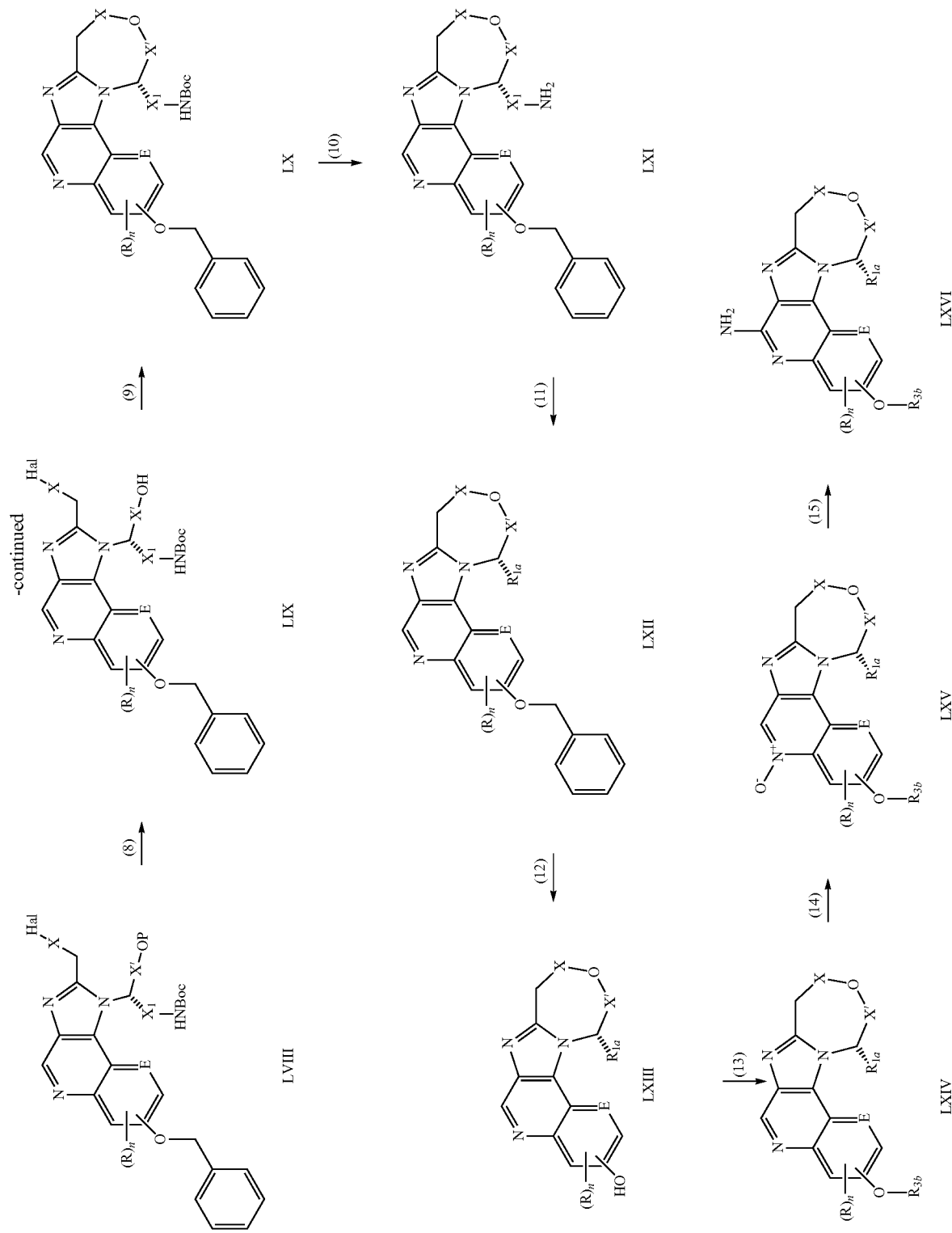

Imidazopyridines of the invention can be prepared according to Reaction Scheme VI, where Boc, P, $R_{1a}$, $R_{A2}$, $R_{B2}$, X, X', and $X_1$ are as defined above. In step (1) of Reaction Scheme VI, a 2,4-dichloro-3-nitropyridine of Formula LXVII is reacted with a compound of Formula XVI to form a 2-chloro-3-nitropyridine of Formula LXVIII. Step (1) of Reaction Scheme VI is conveniently carried out according to the methods described in step (1) of Reaction Scheme I. Many 2,4-dichloro-3-nitropyridines of the Formula LXVII are known and can be readily prepared using known synthetic methods (see, for example, Dellaria et al, U.S. Pat. No. 6,525,064 and the references cited therein).

In step (2) of Reaction Scheme VI, a 2-chloro-3-nitropyridine of Formula LXVIII is reacted with an alkali metal azide to provide an 8-nitrotetrazolo[1,5-c]pyridin-7-amine of Formula LXIX. The reaction can be carried out by combining the compound of Formula LXVIII with an alkali metal azide, for example, sodium azide, in a suitable solvent such as acetonitrile/water, preferably 90/10 acetonitrile/water, in the presence of cerium(III) chloride, preferably cerium(III) chloride heptahydrate. Optionally, the reaction can be carried out with heating, for example, at the reflux temperature. Alternatively, the reaction can be carried out by combining the compound of Formula LXVIII with an alkali metal azide, for example, sodium azide, in a suitable solvent such as DMF and heating, for example to about 50-60° C., optionally in the presence of ammonium chloride.

Steps (3) through (8) of Reaction Scheme VI can be carried out according to the methods described in steps (2) through (5), (8), and (9) of Reaction Scheme I.

In step (9) of Reaction Scheme VI, the tetrazolo ring is removed from a compound of Formula LXXV by reaction with triphenylphosphine to form an N-triphenylphosphinyl intermediate, which is then hydrolyzed to provide a compound of Formula LXXVI, a subgenus of Formulas I, II, IIa, and VII. The reaction with triphenylphosphine can be run in a suitable solvent such as toluene or 1,2-dichlorobenzene under an atmosphere of nitrogen with heating, for example at the reflux temperature. The hydrolysis step can be carried out by general methods well known to those skilled in the art, for example, by heating in a lower alkanol or an alkanol/water solution in the presence of an acid such as trifluoroacetic acid, acetic acid, or hydrochloric acid.

Reaction Scheme VI

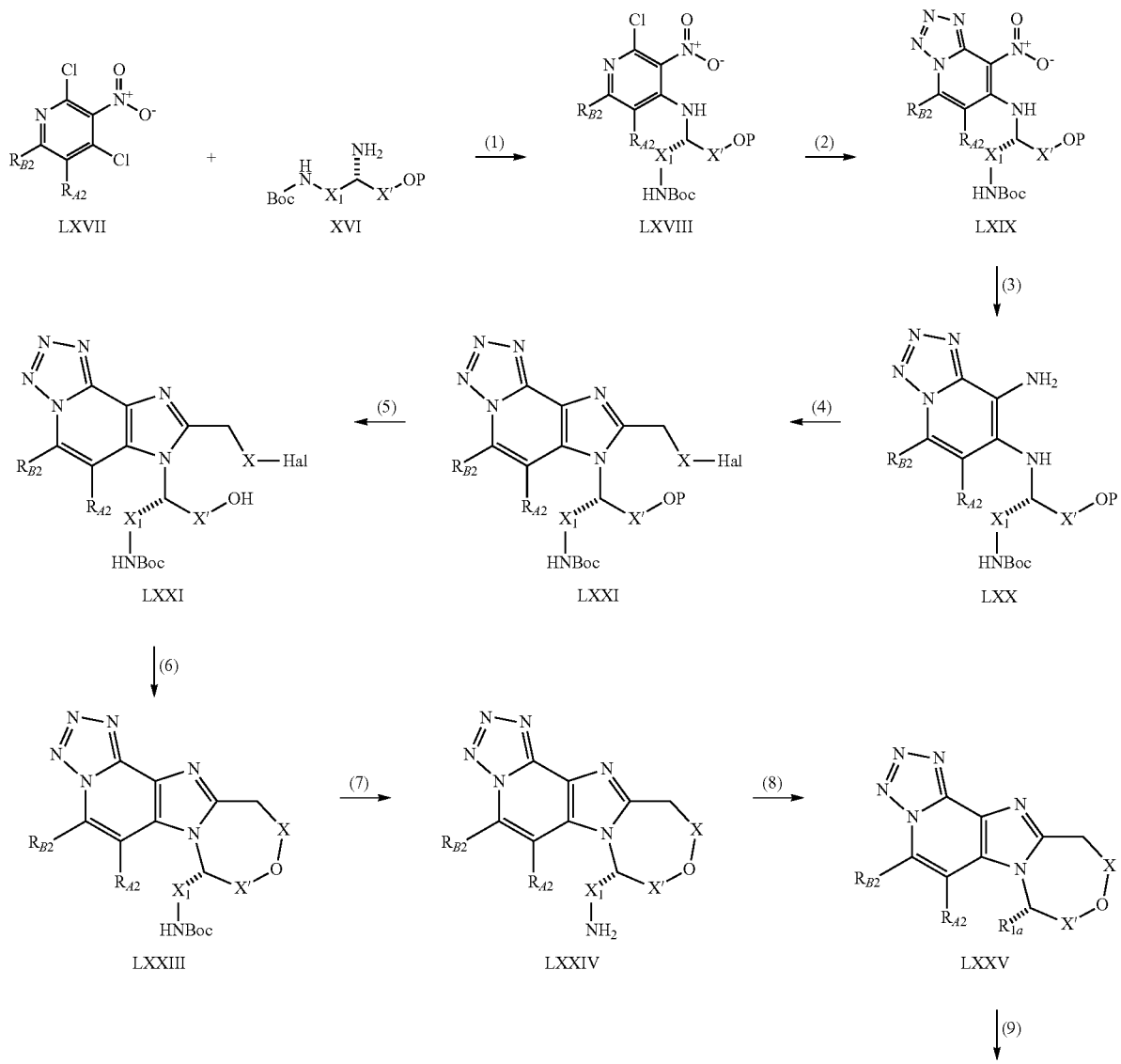

-continued

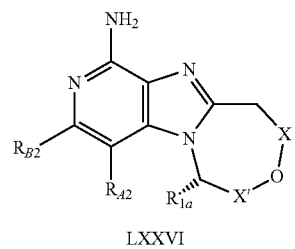

LXXVI

For some embodiments, naphthyridines of the invention can be prepared from tetrazolo compounds of Formulas LXXVII and LXXXI according to Reaction Schemes VII and VIII, wherein $R_{1a}$, R, X, X', $X_1$, and p are as defined above, and -OTf is a trifluoromethanesulfonate group. Compounds of Formulas LXXVII and LXXXI can be prepared by known synthetic routes; see, for example, U.S. Pat. No. 6,194,425 (Gerster et al.). The tetrazolo compounds of Formulas LXXVII and LXXXI can each be treated with a compound of Formula XVI according to the method of step (1) of Reaction Scheme I to provide compounds of Formulas LXXVIII and LXXXII, respectively. A substituted tetrazolonaphthyridine of Formula LXXVIII or LXXXII is converted to a compound of Formula LXXIX or LXXXIII according to the methods of steps (2) through (5), (8), and (9) of Reaction Scheme I.

In step (8) of Reaction Scheme VII and VIII, the tetrazolo group is removed from a compound of Formula LXXIX or LXXXIII to provide a 1H-imidazo[4,5-c]naphthyridin-6-amine of Formula LXXX or Formula LXXXIV. Removal of a tetrazolo group can be carried out in two steps by first treating the compound of Formula LXXIX or LXXXIII with triphenylphosphine and then hydrolyzing the resulting intermediate. The reaction conditions described in U.S. Pat. No. 6,194,425 or the methods described in step (9) of Reaction Scheme VI can be used.

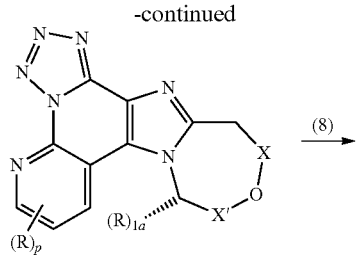

LXXIX

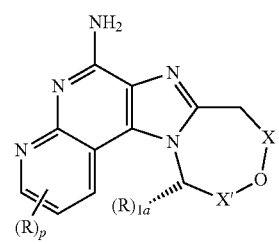

LXXX

Reaction Scheme VII

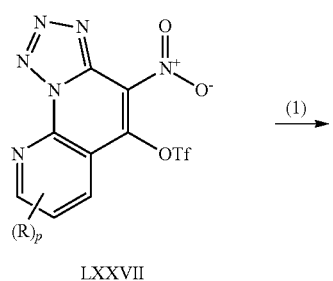

LXXVII

Reaction Scheme VIII

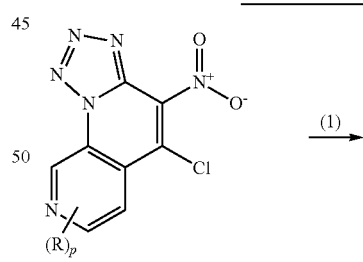

LXXXI

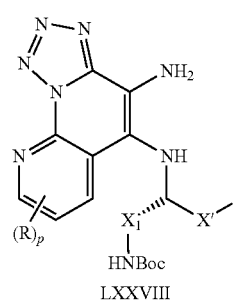

LXXVIII

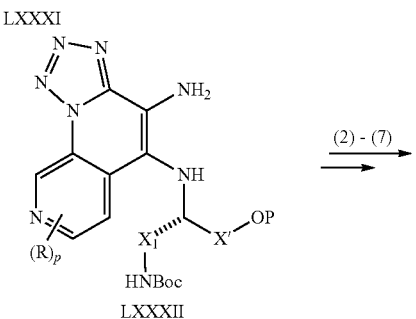

LXXXII

-continued

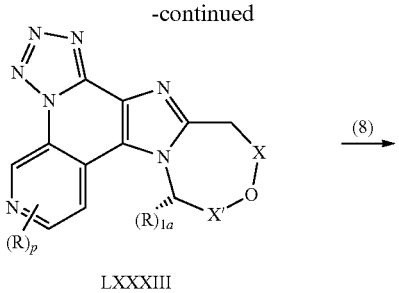

LXXXIII

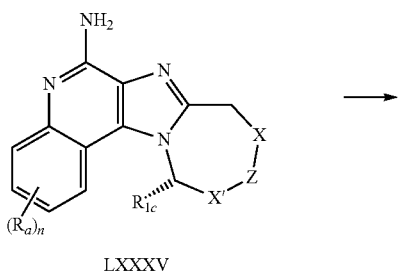

LXXXIV

Compounds of the invention can also be prepared according to Reaction Scheme IX, wherein X, X', Z, and n are as defined above; $R_a$ is alkyl, alkoxy, hydroxy, or $-N(R_9)_2$; and $R_{1c}$ is a subset of $R_1$ as defined above that does not include those substituents that one skilled in the art would recognize as being susceptible to reduction under the acidic hydrogenation conditions of the reaction. These susceptible groups include, for example, alkenyl, alkynyl, and aryl groups and groups bearing nitro substituents. Compounds of Formula LXXXV can be prepared according to the methods of Reaction Scheme I, II, or III.

In Reaction Scheme IX, a 1H-imidazo[4,5-c]quinolin-6-amine of Formula LXXXV is reduced to a tetrahydro-1H-imidazo[4,5-c]quinolin-6-amine of Formula IVa, a subgenus of Formulas I, II, IIa, and IV. The reaction is conveniently carried out under hetereogeneous hydrogenation conditions by adding platinum (IV) oxide to a solution of the compound of Formula LXXXV in trifluoroacetic acid and placing the reaction under hydrogen pressure. The reaction can be carried out on a Parr apparatus at ambient temperature.

Reaction Scheme IX

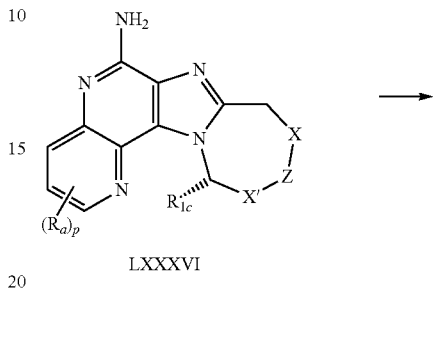

LXXXV

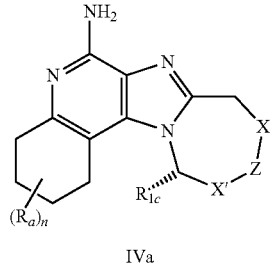

IVa

The reduction described in Reaction Scheme IX can also be used to prepare a tetrahydro-1H-imidazo[4,5-c][1,5]naphthyridin-6-amine of Formula VIa, as shown in Reaction Scheme X, wherein X, X', p, $R_a$, and $R_{1c}$ are as defined above. The product of Formula VIa is a subgenus of Formulas I, II, IIa, and VI.

Reaction Scheme X

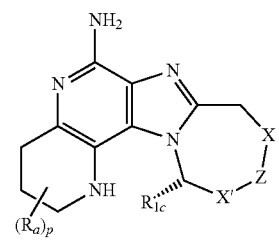

LXXXVI

VIa

In some embodiments, compounds of the invention can be prepared according to Scheme XI, wherein $R_{1a}$, $R_{A2}$, $R_{B2}$, X, X', $X_1$, Boc, and P are as described above and Bn is benzyl. In step (1) of Reaction Scheme XI, a 2-chloro-3-nitropyridine of Formula LXVIII is treated with dibenzylamine to provide an $N^2$-dibenzyl-3-nitropyridin-2,4-diamine of Formula LXXXVII. The reaction can be carried out by combining the compound of Formula LXVIII with dibenzylamine and a tertiary amine such as triethylamine in a suitable solvent such as toluene. The reaction can be carried out at an elevated temperature.

In steps (2) through (5) of Reaction Scheme XI, an $N^2$-dibenzyl-3-nitropyridin-2,4-diamine of Formula LXXXVII is converted to a compound of Formula LXXXVIII using the methods described in steps (3) through (6) of Reaction Scheme VI.

In step (6) of Reaction Scheme XI, the benzyl groups of a compound of Formula LXXXVIII are cleaved using transfer hydrogenation to provide a compound of Formula LXXXIX. The reaction can be carried out by adding ammonium formate to a solution of the compound of Formula LXXXVIII in a suitable solvent such as ethanol or methanol in the presence of a catalyst such as palladium on carbon. The reaction can be carried out at an elevated temperature, for example, the reflux temperature of the solvent.

In step (7) of Reaction Scheme XI, the Boc group is removed from a compound of Formula LXXXIX to provide a compound of Formula XC. The reaction can be carried out using the method described in step (8) of Reaction Scheme I.

In step (8) of Reaction Scheme XI, a compound of Formula XC is converted to a compound of Formula LXXVI using the methods described in step (9) of Reaction Scheme I.

Reaction Scheme XI

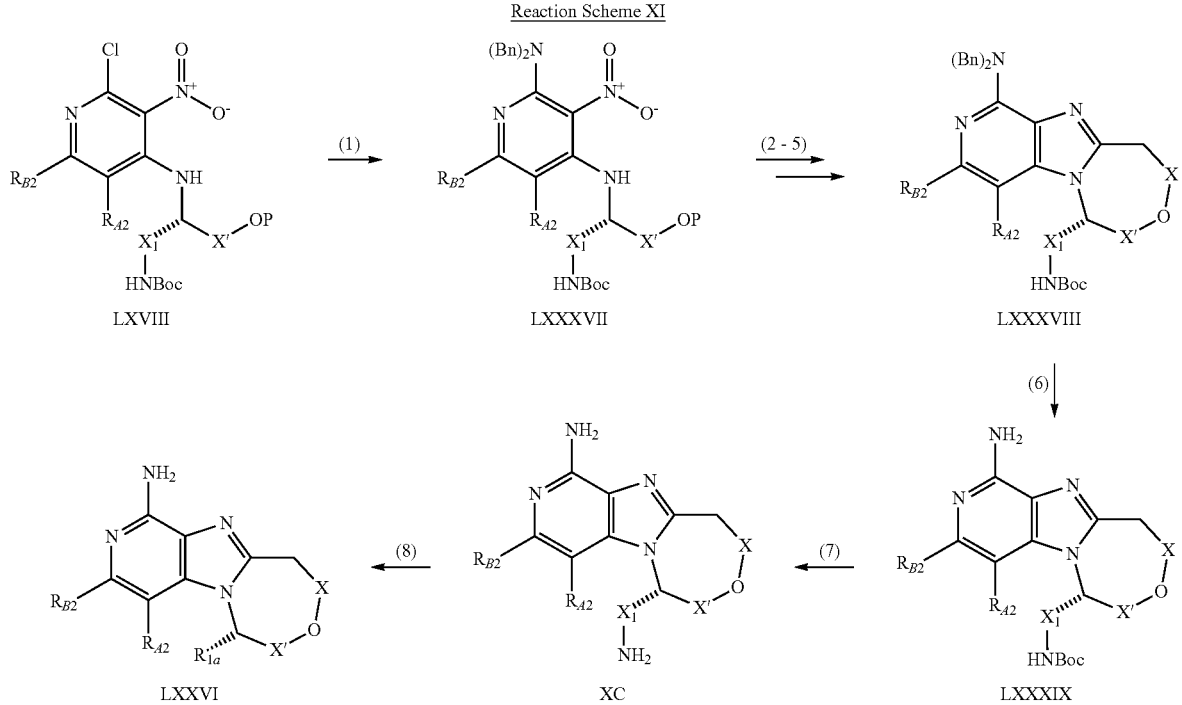

Compounds of the invention can also be prepared using variations of the synthetic routes shown in Reaction Schemes I through XI that would be apparent to one of skill in the art. For example, the synthetic routes shown in Reaction Scheme V or Reaction Scheme VI for the preparation of compounds wherein Z is —O— can be used to prepare compounds wherein Z is —N(—Y—R$_2$)— by using a compound of Formula XL in lieu of the compound of Formula XVI. If the opposite enantiomer of a compound of Formula XVI, XXVIII, or XL is used, the opposite enantiomer of compounds shown in Reaction Scheme I through X would result. If a racemic compound is used instead of a compound of Formula XVI, XXVIII, or XL, a racemic mixture containing compounds of the invention would result. A racemic mixture thus prepared can be resolved by methods known to one skilled in the art, for example, by reacting the racemic mixture with an enantiomerially pure sulfonic acid or carboxylic acid and selectively crystallizing a salt containing one of the enantiomers from the mixture. Compounds of the invention can also be prepared using the synthetic routes described in the EXAMPLES below.

Prodrugs can be prepared in a variety of ways. For example, a compound with a hydroxy substituent may be converted to an ester, an ether, a carbonate, or a carbamate. For compounds containing an alcohol functional group, a prodrug can be formed by the replacement of the hydrogen atom of the alcohol group with a group such as C$_{1-6}$alkanoyloxymethyl, 1-(C$_{1-6}$alkanoyloxy)ethyl, 1-methyl-1-(C$_{1-6}$alkanoyloxy)ethyl, C$_{1-6}$ alkoxycarbonyloxymethyl, N—(C$_{1-6}$alkoxycarbonyl)aminomethyl, succinoyl, C$_{1-6}$alkanoyl, α-aminoC$_{1-4}$alkanoyl, arylacyl, —P(O)(OH)$_2$, —P(O)(O—C$_{1-6}$alkyl)$_2$, C$_{1-6}$alkoxycarbonyl, C$_{1-6}$ alkylcarbamoyl, and α-aminoacyl or α-aminoacyl-α-aminoacyl, where each α-aminoacyl group is independently selected from racemic, D, and L-amino acids. For compounds containing an alcohol functional group, particularly useful prodrugs are esters made from carboxylic acids containing one to six carbon atoms, unsubstituted or substituted benzoic acid esters, or esters made from naturally occurring L-amino acids.

Prodrugs can also be made from a compound containing an amino group by conversion of the amino group to a functional group such as an amide, carbamate, urea, amidine, or another hydroylizable group using conventional methods. A prodrug of this type can be made by the replacement of a hydrogen atom in an amino group, particularly the amino group at the 4-position, with a group such as —C(O)—R″, α-aminoacyl, α-aminoacyl-α-aminoacyl, —C(O)—O—R″, —C(O)—N(R‴)—R″, —C(=NY″)—R″, —CH(OH)—C(O)—OY″, —CH(OC$_{1-4}$alkyl)Y$_0$, —CH$_2$Y$_1$, or —CH(CH$_3$)Y$_1$; wherein R″ and R″ are each independently C$_{1-10}$alkyl, C$_{3-7}$cycloalkyl, or benzyl, each of which may be unsubstituted or substituted by one or more substituents selected from the group consisting of halogen, hydroxy, nitro, cyano, carboxy, C$_{1-6}$ alkyl, C$_{1-4}$alkoxy, aryl, heteroaryl, arylC$_{1-4}$alkylenyl, heteroarylC$_{1-4}$alkylenyl, haloC$_{1-4}$alkylenyl, haloC$_{1-4}$alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$; with the proviso that R‴ may also be hydrogen; each α-aminoacyl group is independently selected from racemic, D, or L-amino acids; Y″ is hydrogen, C$_{1-6}$ alkyl, or benzyl; Y$_0$ is C$_{1-6}$ alkyl, carboxyC$_{1-6}$alkylenyl, aminoC$_{1-4}$alkylenyl, mono-N—C$_{1-6}$alkylaminoC$_{1-4}$alkylenyl, or di-N,N—C$_{1-6}$ alkylaminoC$_{1-4}$alkylenyl; and Y$_1$ is mono-N—C$_{1-6}$alkylamino, di-N,N—C$_{1-6}$alkylamino, morpholin-4-yl, piperidin-1-yl, pyrrolidin-1-yl, or 4-C$_{1-4}$ alkylpiperazin-1-yl. For compounds containing an amine functional group, particularly useful prodrugs are amides derived from carboxylic acids containing one to ten carbon atoms, amides derived from amino acids, and carbamates containing one to ten carbon atoms.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)× 0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used, such as tablets, lozenges, capsules, parenteral formulations, syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce, and certain compounds or salts of the invention may inhibit, the production of certain cytokines in experiments performed according to the tests set forth below. These results indicate that the compounds or salts or compositions are useful for modulating the immune response in a number of different ways, rendering them useful in the treatment of a variety of disorders.

Cytokines whose production may be induced by the administration of compounds or salts of the invention generally include interferon-α (IFN-α) and tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts described herein can also have an effect on the acquired immune response. For example, the production of the T helper type 1 (T$_H$1) cytokine IFN-γ may be induced indirectly and the production of the T helper type 2 (T$_H$2) cytokines IL-4, IL-5 and IL-13 may be inhibited upon administration of the compounds or salts.

Other cytokines whose production may be inhibited by the administration of compounds or salts of the invention, particularly compounds or salts of Formulas II-1, II-1a, III-1, IV-1, V-1, VI-1, and VII-1, or compounds or salts of Formulas II, IIa, III, IV, V, VI, and VII wherein Z is —N(—Y—R$_2$)—, include tumor necrosis factor-α (TNF-α). Among other effects, inhibition of TNF-α production can provide prophylaxis or therapeutic treatment of TNF-α mediated diseases in animals, making the compounds or salt useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella*;

(c) other infectious diseases, such as chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments the induction or inhibition of cytokine biosynthesis may be performed by administering a compound or salt in a dose outside this range. In some of these embodiments, the method includes administering sufficient compound or salt or composition to provide a dose of from about 0.1 mg/m$^2$ to about 2.0 mg/m$^2$ to the subject, for example, a dose of from about 0.4 mg/m$^2$ to about 1.2 mg/m$^2$.

The invention also provides a method of treating a viral infection in an animal and a method of treating a neoplastic disease in an animal comprising administering an effective amount of a compound or salt of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

For examples 1 through 4 and 6 below, the enantiomer of the compound was prepared in a separate experiment; see Examples 67 through 71. A mixture of the two enantiomers was prepared and analyzed by chiral stationary phase high-performance liquid chromatography using a Chiralcel OD-RH column, 0.46 mm×15 cm, eluting with 30% methanol in pentane/methanol/triethylamine 90:10:0.2 (v/v/v) at a flow rate of 1.0 mL/min. Each of examples 1 through 6 below was analyzed in comparison to the mixture of the two enantiomers, and the ratio favoring the enantiomer shown was, for each example, greater than 99:1.

Example 1

N-{[(11S)-6-Amino-10,11-dihydro-8H-[1,4]oxazino[4',3':1,2]imidazo[4,5-c]quinolin-11-yl]methyl}methanesulfonamide

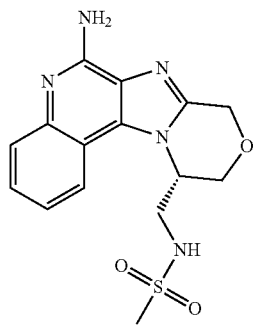 [SMILES: CS(=O)(=O)NC[C@H]1COCc2nc3c(N)nc4ccccc4c3n21]

Part A tert-Butyl (2S)-3-hydroxy-2-(tritylamino)propylcarbamate (5.38 g, 12.5 mmol), prepared from D-serine by the method of Rapoport *J. Org. Chem.*, 65, 4048-4057, (2000) was dissolved in 150 mL of dry $CH_2Cl_2$ and treated with triethylamine (2.25 mL, 16.2 mmol), tert-butyldimethylsilyl cholide (2.45 g, 16.2 mmol) and 4-dimethylaminopyridine (DMAP) (305 mg, 2.5 mmol) and the reaction mixture was stirred under $N_2$ overnight. The reaction mixture was then treated with a 0.5 M solution of $Na_2CO_3$ and the layers were separated. The organic portion was washed with more 0.5 M $Na_2CO_3$ solution, $H_2O$ and brine. The organic portion was then dried over $Na_2SO_4$, filtered and concentrated under reduced pressure. Chromatography ($SiO_2$, 7% ethyl acetate/hexanes) gave tert-butyl (2S)-3-{[tert-butyl(dimethyl)silyl]oxy}-2-(tritylamino)propylcarbamate (6.19 g) as a colorless syrup.

Part B tert-Butyl (2S)-3-{[tert-butyl(dimethyl)silyl]oxy}-2-(tritylamino)propylcarbamate (6.19 g, 11.3 mmol) was dissolved in 115 mL of anhydrous $CH_2Cl_2$ and 18.2 mL of glacial acetic acid. The reaction mixture was cooled to 0° C. under an atmosphere of $N_2$ and boron trifluoride diethyl etherate (1.51 mL, 11.9 mmol) was added dropwise over several minutes. After stirring for 5 hours, the reaction mixture was treated with 183 mL of cold, aqueous 10% NaOH solution. The reaction mixture was extracted into 200 mL of a 3:1 chloroform/2-propanol mixture and the layers were separated. The aqueous portion was extracted with two additional portions of the chloroform/2-propanol mixture. The organic phases were combined and dried over $Na_2SO_4$, filtered and concentrated under reduced pressure. Chromatography ($SiO_2$, 5%-10% methanol/$CHCl_3$) gave tert-butyl (2S)-2-amino-3-{[tert-butyl(dimethyl)silyl]oxy}propylcarbamate (3.43 g) as a colorless syrup.

Part C tert-Butyl (2S)-2-amino-3-{[tert-butyl(dimethyl)silyl]oxy}propylcarbamate (3.43 g, 11.3 mmol) was dissolved in 110 mL of dry $CH_2Cl_2$. Triethylamine (3.14 mL, 22.6 mmol) and 4-chloro-3-nitroquinoline (2.35 g, 11.3 mmol) were then added and the reaction was stirred under $N_2$ overnight. The reaction mixture was then treated with 100 mL of $H_2O$ and 100 mL of $CH_2Cl_2$. The layers were separated and the organic portion was washed successively with $H_2O$ and brine. The organic portion was dried over $Na_2SO_4$, filtered and concentrated under reduced pressure to give yellow solid. Chromatography ($SiO_2$, 0-20% ethyl acetate/$CH_2Cl_2$) gave tert-butyl (2S)-3-{[tert-butyl(dimethyl)silyl]oxy}-2-[(3-nitroquinolin-4-yl)amino]propylcarbamate (4.84 g) as a yellow solid.

Part D tert-Butyl (2S)-3-{[tert-butyl(dimethyl)silyl]oxy}-2-[(3-nitroquinolin-4-yl)amino]propylcarbamate (4.84 g, 10.1 mmol) was dissolved in 150 mL of toluene and the solution was placed in a pressure bottle. Platinum on carbon (5%, 680 mg) was then added and the reaction mixture was shaken under $H_2$ at 52 PSI ($3.6 \times 10^5$ Pa). After 8 hours, the reaction mixture was then filtered through a pad of CELITE filter agent. The pad was rinsed with 2-propanol and the combined filtrates were concentrated under reduced pressure to give tert-butyl (2S)-2-[(3-aminoquinolin-4-yl)amino]-3-{[tert-butyl(dimethyl)silyl]oxy}propylcarbamate (4.51 g) as a brown foam.

Part E tert-Butyl (2S)-2-[(3-aminoquinolin-4-yl)amino]-3-{[tert-butyl(dimethyl)silyl]oxy}propylcarbamate (4.51 g, 10.1 mmol) was dissolved in 80 mL of anhydrous 1,2-dichloroethane and the solution was stirred under $N_2$. Ethyl 2-chloroethanimidoate hydrochloride (2.39 g, 15.1 mmol) was then added and the reaction mixture was heated to 65° C. After stirring overnight, the reaction mixture was cooled and treated with 100 mL of saturated sodium bicarbonate ($NaHCO_3$) solution and 100 mL of $CHCl_3$. The layers were separated and the organic portion was washed successively with $H_2O$ and brine. The organic portion was dried over $Na_2SO_4$, filtered and concentrated under reduced pressure. Chromatography ($SiO_2$, 50% ethyl acetate/hexanes) gave tert-butyl (2S)-3-{[tert-butyl(dimethyl)silyl]oxy}-2-[2-(chloromethyl)-1H-imidazo[4,5-c]quinolin-1-yl]propylcarbamate (3.11 g) as a golden foam.

Part F tert-Butyl (2S)-3-{[tert-butyl(dimethyl)silyl]oxy}-2-[2-(chloromethyl)-1H-imidazo[4,5-c]quinolin-1-yl]propylcarbamate (3.11 g, 6.16 mmol) was dissolved in 60 mL of tetrahydrofuran (THF) and the solution was cooled to −78° C. under $N_2$. A 1.0 M solution of tetrabutylammonium fluoride in THF (6.8 mL) was added and the reaction mixture was allowed to warm to −10° C. over 2 hours. The reaction mixture was then treated with 50 mL of saturated sodium bicarbonate solution and 200 mL of $CH_2Cl_2$. The layers were separated and the organic portion was washed with $H_2O$ (50 mL) and brine (4×25 mL). The organic layer was dried over $Na_2SO_4$, filtered and concentrated under reduced pressure to give a golden syrup. The syrup was concentrated from toluene (3×) to give a pale yellow foam. This material was dissolved in 70 mL of anhydrous THF and the solution was stirred under $N_2$. Solid potassium tert-butoxide (507 mg, 6.18 mmol) was then added and the reaction mixture was allowed to stir for 2.5 hours. A solution of 50 mL of saturated sodium bicarbonate was then added and the THF was then removed under reduced pressure. The resulting material was treated with 150 mL of $CH_2Cl_2$ and layers were separated. The organic portion was washed with $H_2O$ and brine. The organic portion was then dried over $Na_2SO_4$, filtered and concentrated under reduced to give brown foam. Chromatography ($SiO_2$, 20% 80:18:2 $CHCl_3$/methanol/concentrated $NH_4OH$(CMA)/$CHCl_3$) gave tert-butyl (11S)-10,11-dihydro-8H-[1,4]oxazino[4',3':1,2]imidazo[4,5-c]quinolin-11-ylmethylcarbamate (1.62 g) as a light yellow foam.

Part G tert-Butyl (11S)-10,11-dihydro-8H-[1,4]oxazino[4',3':1,2]imidazo[4,5-c]quinolin-11-ylmethylcarbamate (1.62 g, 4.58 mmol) was dissolved in 40 mL of $CH_2Cl_2$ and treated with 3-chloroperoxybenzoic acid (MCPBA) (1.23 g, 77% maximum purity). After stirring for 2 hours, the reaction mixture was treated with 40 mL of 2% $Na_2CO_3$ solution and 40 mL of $CH_2Cl_2$ and the layers were separated. The aqueous layer was then extracted with $CH_2Cl_2$ (3×20 mL). The combined organic layers were washed with 10 mL of brine. The organic portion was then dried over Na₂SO₄, filtered and concentrated under reduced pressure to give tert-butyl [(11S)-5-oxido-10,11-dihydro-8H-[1,4]oxazino[4',3':1,2]imidazo[4,5-c]quinolin-11-yl]methylcarbamate (1.69 g) as a crusty, off-white solid.

Part H tert-Butyl [(11S)-5-oxido-10,11-dihydro-8H-[1,4]oxazino[4',3':1,2]imidazo[4,5-c]quinolin-11-yl]methylcarbamate (1.69 g, 4.57 mmol) was dissolved in 20 mL of CH₂Cl₂ and treated with 2 mL of concentrated NH₄OH solution. The mixture was stirred rapidly and then p-toluenesulfonyl chloride (958 mg, 5.02 mmol) was carefully added. Rapid stirring was continued for 2 hours. The reaction mixture was treated with 25 mL of CH₂Cl₂ and 25 mL of H₂O. The layers were separated and the organic portion was washed with 2% Na₂CO₃ solution (3×20 mL), H₂O and brine. The organic portion was dried over Na₂SO₄, filtered and concentrated under reduced pressure. Chromatography (SiO₂, 10-30% CMA/CHCl₃) gave tert-butyl [(11S)-6-amino-10,11-dihydro-8H-[1,4]oxazino[4',3':1,2]imidazo[4,5-c]quinolin-11-yl]methylcarbamate (1.39 g) as a salmon colored foam.

Part I tert-Butyl [(11S)-6-amino-10,11-dihydro-8H-[1,4]oxazino[4',3':1,2]imidazo[4,5-c]quinolin-11-yl]methylcarbamate (1.39 g, 3.77 mmol) was dissolved in 10 mL of ethanol and 3 mL of a 4.3 M solution of HCl in ethanol was added. The reaction mixture was heated to 85° C. After 1 hour, the reaction mixture was concentrated under reduced pressure. The resulting residue was treated with 40 mL of H₂O and 20 mL of CHCl₃. The layers were separated and the organic portion was discarded. The aqueous layer was then made basic by addition of 5 mL of concentrated NH₄OH solution. The aqueous portion was then extracted with CHCl₃ (15×20 mL). The combined organic extracts were concentrated under reduced pressure to give (11S)-11-(aminomethyl)-10,11-dihydro-8H-[1,4]oxazino[4',3':1,2]imidazo[4,5-c]quinolin-6-amine (778 mg) as a pumpkin colored solid.

Part J (11S)-11-(Aminomethyl)-10,11-dihydro-8H-[1,4]oxazino[4',3':1,2]imidazo[4,5-c]quinolin-6-amine (778 mg, 2.89 mmol) was dissolved in 60 mL of CH₂Cl₂ and treated with triethylamine (804 µL, 5.78 mmol). The solution was cooled to 0° C. under N₂. Methanesulfonyl chloride (224 µL, 2.89 mmol) was then added dropwise. After 75 minutes, the reaction was treated with H₂O and extracted repeatedly with 10% methanol/CHCl₃. The combined organic layers were washed successively with H₂O and brine. The organic portion was dried over Na₂SO₄, filtered and concentrated under reduced pressure. Chromatography (SiO₂, 10-15% methanol/CHCl₃) gave an off-white solid. Crystallization from methanol gave N-{[(11S)-6-amino-10,11-dihydro-8H-[1,4]oxazino[4',3':1,2]imidazo[4,5-c]quinolin-11-yl]methyl}methanesulfonamide (487 mg) as white, powdery crystals, mp 285-288° C.

¹H NMR (300 MHz, DMSO-d₆) δ 8.14 (d, J=7.8 Hz, 1H), 7.82 (m, 1H), 7.62 (d, J=7.5 Hz, 1H), 7.45 (t, J=7.1 Hz, 1H), 7.24 (t, J=7.0 Hz, 1H), 6.57 (s, 2H), 5.11 (d, J=15.7 Hz, 1H), 4.97 (d, J=15.7 Hz, 1H), 4.90 (m, 1H), 4.43 (d, J=12.2 Hz, 1H), 4.08 (m, 1H), 3.45-3.16 (m, 2H), 2.94 (s, 3H); ¹³C NMR (75 MHz, DMSO-d₆) δ 152.1, 145.5, 145.1, 131.9, 127.0, 126.7, 126.5, 121.7, 121.0, 114.7, 65.1, 63.7, 54.3, 42.6; MS m/z 348 (M+H)⁺. Anal. calcd for C₁₅H₁₇N₅O₃S: C, 51.86; H, 4.93; N, 20.16. Found: C, 51.76; H, 4.71; N, 20.13.

Example 2

N-{3-[(11S)-6-Amino-10,11-dihydro-8H-[1,4]oxazino[4',3':1,2]imidazo[4,5-c]quinolin-11-yl]propyl}methanesulfonamide

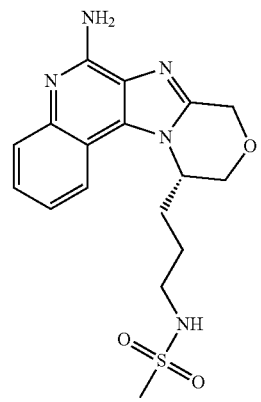 [SMILES: CS(=O)(=O)NCCC[C@H]1COCc2nc3c(N)nc4ccccc4c3n21]

Part A

N²-[(Benzyloxy)carbonyl]-N⁵-(tert-butoxycarbonyl)-L-ornithine (27.6 g, 75.4 mmol), prepared from L-ornithine by the method of Masiukiewicz, Org. Prep. Proced. Int. 34, 531-537, (2002) was dissolved in 300 mL of anhydrous THF and the solution was cooled to 0° C. under N₂. Triethylamine (13.6 mL, 98.0 mmol) was added and the solution was stirred for 30 min. Ethyl chloroformate (8.65 mL, 90.5 mmol) was then added and the reaction mixture was stirred at ambient temperature for 75 minutes. The reaction mixture was then cooled back to 0° C. and treated with a solution of NaBH₄ (5.73 g, 151 mmol) dissolved in 125 mL of H₂O. The reaction was allowed to warm to ambient temperature overnight. The reaction mixture was then carefully treated with 1N HCl until the pH reached 5 to 6. The THF was removed under reduced pressure and the remaining aqueous portion was extracted with 300 mL of ethyl acetate. The organic portion was washed successively with 10% NaOH solution, H₂O and brine. The organic portion was dried over Na₂SO₄, filtered and concentrated under reduced pressure. Chromatography (50-100% ethyl acetate/hexanes gave [4-tert-butoxycarbonylamino-1S-(hydroxymethyl)butyl]carbamic acid benzyl ester (11.9 g) as a white solid.

Part B

[4-tert-Butoxycarbonylamino-1S-(hydroxymethyl)butyl]carbamic acid benzyl ester (5.38 g, 15.3 mmol) was dissolved in 150 mL of CH₂Cl₂ and treated with triethylamine (2.55 mL, 18.3 mmol), tert-butyldimethylsilyl chloride (2.76 g, 18.3 mmol) and DMAP (187 mg, 1.53 mmol). The reaction mixture was stirred under N₂ for 2 days. The reaction mixture was then treated with saturated sodium bicarbonate solution and the layers were separated. The organic portion was washed successively with 3.5% NaH₂PO₄ solution, H₂O and brine. The organic portion was dried over Na₂SO₄, filtered and concentrated under reduced pressure. Chromatography (33% ethyl acetate/hexanes) gave [4-tert-butoxycarbonylamino-1S-(tert-butyldimethylsilanyloxymethyl)butyl]carbamic acid benzyl ester (5.26 g) as a colorless oil that solidified on standing Part C

[4-tert-Butoxycarbonylamino-1S-(tert-butyldimethylsilanyloxymethyl)butyl]carbamic acid benzyl ester (5.26 g, 11.3 mmol) was dissolved in 100 mL of methanol and the solution was placed in a pressure bottle. Palladium on carbon (10%, 500 mg) was then added and the reaction mixture was shaken under $H_2$ at 50 PSI ($3.4 \times 10^5$ Pa). After 8 hours, the reaction mixture was then filtered through a pad of CELITE filter agent. The pad was rinsed with methanol and the combined filtrates were concentrated under reduced pressure to give tert-butyl (4S)-4-amino-5-{[tert-butyl(dimethyl)silyl]oxy}pentylcarbamate (3.76 g) as a colorless oil.

Part D tert-Butyl (4S)-4-amino-5-{[tert-butyl(dimethyl)silyl]oxy}pentylcarbamate (3.76 g, 11.3 mmol) was dissolved in 100 mL of dry $CH_2Cl_2$ and the solution was cooled to 0° C. under $N_2$. Triethylamine (3.10 mL, 22.3 mmol) and 4-chloro-3-nitroquinoline (2.36 g, 11.3 mmol) were then added and the reaction was allowed to warm to ambient temperature and stirred for 2 days. The reaction mixture was then concentrated under reduced pressure to give a yellow solid. The solid was dissolved in 200 mL of $CH_2Cl_2$ and was washed successively with $H_2O$ and brine. The organic portion was dried over $Na_2SO_4$, filtered and concentrated under reduced pressure to give yellow solid. Chromatography ($SiO_2$, 20-35% ethyl acetate/hexanes) gave tert-butyl (4S)-5-{[tert-butyl(dimethyl)silyl]oxy}-4-[(3-nitroquinolin-4-yl)amino]pentylcarbamate (5.65 g) as a yellow syrup.

Part E tert-Butyl (4S)-5-{[tert-butyl(dimethyl)silyl]oxy}-4-[(3-nitroquinolin-4-yl)amino]pentylcarbamate (5.65 g, 11.2 mmol) was dissolved in 100 mL of acetonitrile and the solution was placed in a pressure bottle. Platinum on carbon (5%, 1.2 g) was then added and the reaction mixture was shaken under $H_2$ at 50 PSI ($3.4 \times 10^5$ Pa). After 4 hours, an additional 500 mg of platinum on carbon was added and shaking was continued for 3 hours. The reaction mixture was then filtered through a pad of CELITE filter agent. The pad was rinsed with acetonitrile and the combined filtrates were concentrated under reduced pressure to give tert-butyl (4S)-4-[(3-aminoquinolin-4-yl)amino]-5-{[tert-butyl(dimethyl)silyl]oxy}pentylcarbamate (4.61 g) as an orange foam.

Part F tert-Butyl (4S)-4-[(3-aminoquinolin-4-yl)amino]-5-{[tert-butyl(dimethyl)silyl]oxy}pentylcarbamate (1.65 g, 3.48 mmol) was dissolved in 35 mL of anhydrous 1,2-dichloroethane and the solution was stirred under $N_2$. Ethyl 2-chloroethanimidoate hydrochloride (1.18 g, 7.47 mmol) was then added and the reaction mixture was heated to 65° C. After stirring overnight, the reaction mixture was cooled and treated with 100 mL of saturated $NaHCO_3$ solution and 100 mL of $CHCl_3$. The layers were separated and the organic portion was washed successively with $H_2O$ and brine. The organic portion was dried over $Na_2SO_4$, filtered and concentrated under reduced pressure. Chromatography ($SiO_2$, 25-100% ethyl acetate/hexanes) gave tert-butyl (4S)-5-{[tert-butyl(dimethyl)silyl]oxy}-4-[2-(chloromethyl)-1H-imidazo[4,5-c]quinolin-1-yl]pentylcarbamate (1.36 g) as a golden foam.

Part G tert-Butyl (4S)-5-{[tert-butyl(dimethyl)silyl]oxy}-4-[2-(chloromethyl)-1H-imidazo[4,5-c]quinolin-1-yl]pentylcarbamate (1.28 g, 2.40 mmol) was dissolved in 200 mL of $CH_2Cl_2$ and the solution was cooled to −78° C. under $N_2$. A 1.0 M solution of tetrabutylammonium fluoride in THF (2.88 mL) was added and the reaction mixture was allowed to warm to ambient temperature. After 4 days, the reaction mixture was then treated with 50 mL of saturated sodium bicarbonate solution. The layers were separated and the organic portion was washed with $H_2O$ (50 mL) and brine (4×25 mL). The organic layer was dried over $Na_2SO_4$, filtered and concentrated under reduced pressure. Chromatography ($SiO_2$, 4% methanol/$CHCl_3$) gave tert-butyl 3-[(11S)-10,11-dihydro-8H-[1,4]oxazino[4',3':1,2]imidazo[4,5-c]quinolin-11-yl]propylcarbamate (820 mg) as a light yellow foam.

Part H tert-Butyl 3-[(11S)-10,11-dihydro-8H-[1,4]oxazino[4',3':1,2]imidazo[4,5-c]quinolin-11-yl]propylcarbamate (820 mg, 2.15 mmol) was dissolved in 20 mL of $CH_2Cl_2$ and treated with 3-chloroperoxybenzoic acid (648 mg, 57-86%). After stirring for 2 h, the reaction mixture was treated with 20 mL of 2% $Na_2CO_3$ solution and the layers were separated. The aqueous layer was then extracted with $CH_2Cl_2$ (3×20 mL). The combined organic layers were concentrated under reduced pressure to give tert-butyl 3-[(11S)-5-oxido-10,11-dihydro-8H-[1,4]oxazino[4',3':1,2]imidazo[4,5-c]quinolin-11-yl]propylcarbamate (850 mg) as a crusty, off-white solid.

Part I tert-Butyl 3-[(11S)-5-oxido-10,11-dihydro-8H-[1,4]oxazino[4',3':1,2]imidazo[4,5-c]quinolin-11-yl]propylcarbamate (850 mg, 2.15 mmol) was dissolved in 25 mL of $CH_2Cl_2$ and treated with 3 mL of concentrated $NH_4OH$ solution. The mixture was stirred rapidly and then p-toluenesulfonyl chloride (451 mg, 2.37 mmol) was carefully added. Rapid stirring was continued for 2 hours. The reaction mixture was treated with 25 mL of $CH_2Cl_2$ and 25 mL of $H_2O$. The layers were separated and the organic portion was washed with 2% $Na_2CO_3$ solution (3×25 mL), $H_2O$ and brine. The organic portion was dried over $Na_2SO_4$, filtered and concentrated under reduced pressure. Chromatography ($SiO_2$, 4% methanol/$CHCl_3$ with 0.4% concentrated $NH_4OH$) gave tert-butyl 3-[(11S)-6-amino-10,11-dihydro-8H-[1,4]oxazino[4',3':1,2]imidazo[4,5-c]quinolin-11-yl]propylcarbamate (734 mg) as an off-white foam.

Part J tert-Butyl 3-[(11S)-6-amino-10,11-dihydro-8H-[1,4]oxazino[4',3':1,2]imidazo[4,5-c]quinolin-11-yl]propylcarbamate (689 mg, 1.74 mmol) was dissolved in 10 mL of ethanol and 2 mL of a 4.0 M solution of HCl in ethanol was added. The reaction mixture was heated to 75° C. After 1 hour, the reaction mixture was concentrated under reduced pressure. The resulting residue was treated with 25 mL $H_2O$ and 20 mL of $CHCl_3$. The layers were separated and the organic portion was discarded. The aqueous layer was then made basic by addition of 5 mL of concentrated $NH_4OH$ solution. The aqueous portion was then extracted with $CHCl_3$ (6×10 mL). The combined organic extracts were concentrated under reduced pressure to give (11S)-1143-aminopropyl)-10,11-dihydro-8H-[1,4]oxazino[4',3':1,2]imidazo[4,5-c]quinolin-6-amine (469 mg) as a white foam.

Part K (11S)-11-(3-Aminopropyl)-10,11-dihydro-8H-[1,4]oxazino[4',3':1,2]imidazo[4,5-c]quinolin-6-amine (870 mg, 2.93 mmol) was dissolved in 30 mL of $CH_2Cl_2$ and the reaction mixture was cooled to 0° C. under $N_2$. Triethylamine (815 μL, 2.93) was added followed by methanesulfonyl chloride (227 μL, 2.93 mmol). After stirring for 90 minutes, the reaction mixture was treated with 10% methanol/$CHCl_3$ and was washed successively with $H_2O$ and brine. The organic portion was dried over $Na_2SO_4$, filtered and concentrated under reduced pressure. Chromatography ($SiO_2$, 10% methanol/$CHCl_3$ with 0.5% concentrated $NH_4OH$) gave a white solid. Crystallization from methanol gave N-{3-[(11S)-6-amino-10,11-dihydro-8H-[1,4]oxazino[4',3':1,2]imidazo[4,5-c]quinolin-11-yl]propyl}methanesulfonamide (452 mg) as colorless needles, mp 249.0-250.0° C.

$^1$H NMR (300 MHz, DMSO-$d_6$) δ 7.94 (d, J=7.6 Hz, 1H), 7.63 (dd, J=1.0, 8.3 Hz, 1H), 7.44 (ddd, J=1.1, 7.2, 8.2 Hz, 1H), 7.28 (ddd, J=1.1, 7.2, 8.1 Hz, 1H), 6.99 (t, J=5.9 Hz, 1H), 6.56 (s, 2H), 5.10 (d, J=15.6 Hz, 1H), 4.97 (d, J=15.6 Hz, 1H), 4.96 (m, 1H), 4.29 (d, J=12.4 Hz, 1H), 4.09 (dd, J=2.4, 12.4 Hz, 1H), 2.96 (q, J=6.4 Hz, 2H), 2.84 (s, 3H), 1.94 (m, 2H), 1.80 (m, 1H), 1.64 (m, 1H); $^{13}$C NMR (75 MHz, DMSO-$d_6$) δ 152.2, 145.5, 145.0, 131.6, 126.9, 126.8, 126.5, 121.7, 120.6, 114.9, 65.0, 54.2, 42.7, 29.8, 25.9; MS m/z 376 (M+H)$^+$. Anal. calcd for $C_{17}H_{21}N_5O_3S$: C, 54.38; H, 5.64; N, 18.65. Found: C, 54.04; H, 5.65; N, 18.45.

Example 3
N-{3-[(11S)-6-Amino-2,3,4,8,10,11-hexahydro-1H-[1,4]oxazino[4',3':1,2]imidazo[4,5-c]quinolin-11-yl]propyl}methanesulfonamide

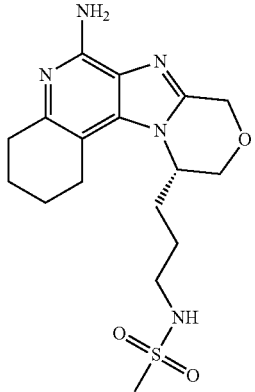 [SMILES: CS(=O)(=O)NCCC[C@H]1COCc2nc3c(N)nc4c(c3n21)CCCC4]

N-{3-[(11S)-6-Amino-10,11-dihydro-8H-[1,4]oxazino[4',3':1,2]imidazo[4,5-c]quinolin-11-yl]propyl}methanesulfonamide (254 mg, 0.667 mmol) was dissolved in about 3 mL of trifluoroacetic acid and the solution was placed in a pressure bottle. Platinum oxide (154 mg) was then added and the reaction mixture was shaken under $H_2$ at 50 PSI ($3.4 \times 10^5$ Pa). After 24 hours, the reaction mixture was filtered through a pad of CELITE filter agent. The pad was rinsed with a mixture of 2-propanol and $CH_2Cl_2$ and the combined filtrates were concentrated under reduced pressure to give a syrup. The syrup was partitioned between $H_2O$ and $CHCl_3$. The aqueous layer was made basic by addition of concentrated $NH_4OH$ solution until the pH was approximately 12. The layers were separated and the organic portion was washed successively with concentrated $NH_4OH$, $H_2O$ and brine. The organic portion was dried over $Na_2SO_4$, filtered and concentrated under reduced pressure. Chromatography ($SiO_2$, 25-33% CMA/$CHCl_3$) gave a white solid. Crystallization from methanol/ethyl acetate gave N-{3-[(11S)-6-amino-2,3,4,8,10,11-hexahydro-1H-[1,4]oxazino[4',3':1,2]imidazo[4,5-c]quinolin-11-yl]propyl}methanesulfonamide (85 mg) as white crystals, mp 197-200° C.

$^1$H NMR (300 MHz, DMSO-$d_6$) δ 7.01 (t, J=5.9 Hz, 1H), 5.77 (s, 2H), 4.96 (d, J=15.6 Hz, 1H), 4.83 (d, J=15.5 Hz, 1H), 4.57 (m, 1H), 4.15 (d, J=12.5 Hz, 1H), 3.93 (d, J=11.2 Hz, 1H), 3.05-2.80 (m, 4H), 2.86 (s, 3H), 2.67 (m, 2H), 1.93-1.60 (m, 8H); $^{13}$C NMR (75 MHz, DMSO-$d_6$) δ 149.2, 146.0, 144.5, 136.7, 124.4, 105.2, 65.1, 64.5, 53.5, 42.2, 32.1, 30.8, 25.6, 22.6; MS m/z 380 (M+H)$^+$. Anal. calcd for $C_{17}H_{25}N_5O_3S$: C, 53.81; H, 6.64; N, 18.46. Found: C, 53.61; H, 6.53; N, 18.54.

Example 4
N-{3-[(11S)-6-Amino-10,11-dihydro-8H-[1,4]oxazino[4',3':1,2]imidazo[4,5-c]quinolin-11-yl]propyl}morpholine-4-carboxamide

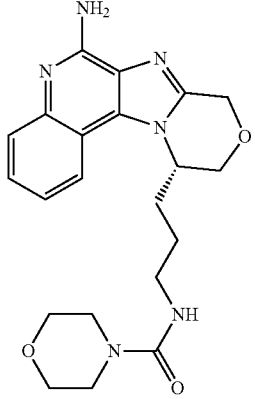 [SMILES: Nc1nc2ccccc2c2c1nc1n2[C@@H](CCCNC(=O)N2CCOCC2)COC1]

(11S)-11-(3-Aminopropyl)-10,11-dihydro-8H-[1,4]oxazino[4',3':1,2]imidazo[4,5-c]quinolin-6-amine (180 mg, 0.606 mmol) was dissolved in 8 mL of $CH_2Cl_2$ and the reaction mixture was cooled to 0° C. under $N_2$. Triethylamine (337 μL, 2.42 mmol) was added followed by morpholinecarbonyl chloride (71 μL, 0.611 mmol). After stirring overnight, the reaction mixture was treated with 10% methanol/$CHCl_3$ and was washed successively with saturated $NaHCO_3$ solution, $H_2O$ and brine. The organic portion was dried over $Na_2SO_4$, filtered and concentrated under reduced pressure. Chromatography ($SiO_2$, 10-12% methanol/$CHCl_3$) gave 100 mg of a white foam. Crystallization from methanol/propyl acetate gave N-{3-[(11S)-6-amino-10,11-dihydro-8H-[1,4]oxazino[4',3':1,2]imidazo[4,5-c]quinolin-11-yl]propyl}morpholine-4-carboxamide (50 mg) as colorless needles, mp 220-222° C.

$^1$H NMR (300 MHz, DMSO-$d_6$) δ 7.88 (d, J=8.1 Hz, 1H), 7.63 (d, J=8.2 Hz, 1H), 7.44 (t, J=7.6 Hz, 1H), 7.25 (t, J=7.1 Hz, 1H), 6.56 (s, 2H), 6.50 (t, J=5.4 Hz, 1H), 5.09 (d, J=15.6 Hz, 1H), 4.99 (d, J=15.7 Hz, 1H), 4.90 (m, 1H), 4.27 (d, J=12.4 Hz, 1H), 4.08 (dd, J=2.5, 12.4 Hz, 1H), 3.44 (t, J=4.8 Hz, 4H), 3.15 (t, J=5.0 Hz, 4H), 3.05 (m, 2H), 1.88 (m, 2H), 1.72 (m, 1H), 1.57 (m, 1H); MS m/z 411 (M+H)$^+$; Anal. calcd for $C_{21}H_{26}N_6O_3$: C, 61.45; H, 6.38; N, 20.47. Found: C, 61.25; H, 6.53; N, 20.32.

Example 5
N-{3-[(11S)-6-Amino-2,3,4,8,10,11-hexahydro-1H-[1,4]oxazino[4',3':1,2]imidazo[4,5-c]quinolin-11-yl]propyl}morpholine-4-carboxamide

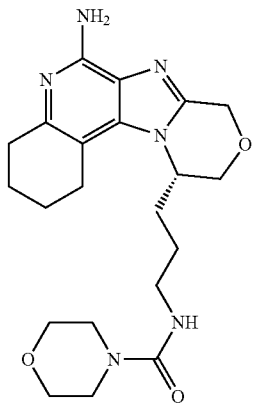 [SMILES: Nc1nc2c(c3c1nc1n3[C@@H](CCCNC(=O)N3CCOCC3)COC1)CCCC2]

N-{3-[(11S)-6-Amino-10,11-dihydro-8H-[1,4]oxazino[4',3':1,2]imidazo[4,5-c]quinolin-11-yl]propyl}morpholine-4-carboxamide (698 mg, 1.70 mmol) was dissolved in 5 mL of trifluoroacetic acid and the solution was placed in a pressure bottle. Platinum oxide (386 mg) was then added and the reaction mixture was shaken under $H_2$ at 50 PSI ($3.4 \times 10^5$ Pa). After 2 days, the reaction mixture was filtered through a pad of CELITE filter agent. The pad was rinsed with a mixture of methanol and $CH_2Cl_2$ and the combined filtrates were concentrated under reduced pressure to give a syrup. The syrup was portioned between 20 mL of concentrated $NH_4OH$ solution and 50 mL of $CHCl_3$. The layers were separated and the aqueous portion was extracted with an additional 50 mL of $CHCl_3$. The combined organic portions were washed successively with concentrated $NH_4OH$, $H_2O$ and brine. The organic portion was dried over $Na_2SO_4$, filtered and concentrated under reduced pressure. Chromatography ($SiO_2$, 20% CMA/$CHCl_3$) gave a fluffy, white solid. Crystallization from methanol/propyl acetate gave N-{3-[(11S)-6-amino-2,3,4,8,10,11-hexahydro-1H-[1,4]oxazino[4',3':1,2]imidazo[4,5-c]quinolin-11-yl]propyl}morpholine-4-carboxamide (395 mg) as fluffy, white needles, mp 154-156° C. $^1$H NMR (300 MHz, $CDCl_3$) δ 5.07 (d, J=15.8 Hz, 1H), 4.87 (d, J=15.8 Hz, 1H), 4.87 (s, 2H), 4.55 (t, J=5.3 Hz, 1H), 4.43 (m, 1H), 4.22 (d, J=12.3 Hz, 1H), 3.95 (dd, J=1.5, 12.3 Hz, 1H), 3.67 (t, J=4.9 Hz, 4H), 3.32-3.23 (m, 6H), 3.00-2.83 (m, 4H), 2.05 (m, 1H), 1.90-1.71 (m, 6H), 1.60 (m, 1H); $^{13}$C NMR (125 MHz, CDCl$_3$) δ 157.8, 148.7, 147.5, 145.2, 137.5, 125.2, 106.9, 66.5, 65.8, 65.6, 54.8, 44.0, 40.6, 32.5, 31.3, 26.5, 23.9, 23.1, 22.9; MS (ESI) m/z 415 (M+H)$^+$; Anal. calcd for C$_{21}$H$_{30}$N$_6$O$_3$·0.67H$_2$O: C, 59.13; H, 7.41; N, 19.70. Found: C, 59.13; H, 7.61; N, 19.70.

Example 6

N-{3-[(11S)-6-Amino-10,11-dihydro-8H-[1,4]oxazin[4',3':1,2]imidazo[4,5-c]quinolin-11-yl]propyl}-2-methylpropanamide

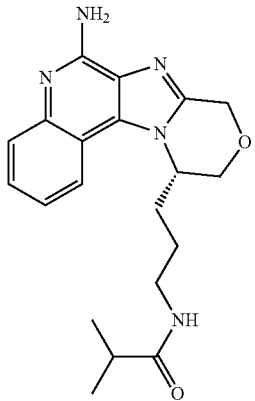 [SMILES: CC(C)C(=O)NCCC[C@H]1COCc2nc3c(N)nc4ccccc4c3n21]

(11S)-11-(3-Aminopropyl)-10,11-dihydro-8H-[1,4]oxazino[4',3':1,2]imidazo[4,5-c]quinolin-6-amine (190 mg, 0.640 mmol) was dissolved in 8 mL of CH$_2$Cl$_2$ and the reaction mixture was cooled to 0° C. under N$_2$. Triethylamine (356 µL, 2.56 mmol) was added followed by iso-butyryl chloride (67 µL, 0.643 mmol). After stirring overnight, the reaction mixture was diluted with 20 mL of CH$_2$Cl$_2$ and was washed successively with saturated NaHCO$_3$ solution, H$_2$O and brine. The organic portion was dried over Na$_2$SO$_4$, filtered and concentrated under reduced pressure. Chromatography (SiO$_2$, 10% methanol/CHCl$_3$) gave a white solid. Crystallization from ethyl acetate gave N-{3-[(11S)-6-amino-10,11-dihydro-8H-[1,4]oxazino[4',3':1,2]imidazo[4,5-c]quinolin-11-yl]propyl}-2-methylpropanamide (80 mg) as a white solid, mp 207-208° C.

$^1$H NMR (300 MHz, DMSO-d$_6$) δ 7.88 (d, J=7.8 Hz, 1H), 7.69 (t, J=5.5 Hz, 1H), 7.62 (dd, J=0.8, 8.3 Hz, 1H), 7.43 (ddd, J=0.8, 7.2, 8.0 Hz, 1H), 7.25 (ddd, J=1.0, 7.0, 8.1 Hz, 1H), 6.56 (s, 2H), 5.09 (d, J=15.6 Hz, 1H), 4.96 (d, J=15.7 Hz, 1H), 4.89 (m, 1H), 4.26 (d, J=12.3 Hz, 1H), 4.07 (dd, J=2.1, 12.3 Hz, 1H), 3.05 (m, 2H), 2.21 (m, 1H), 1.88 (m, 2H), 1.71 (m, 1H), 1.56 (m, 1H), 0.89 (d, J=6.8 Hz, 3H), 0.86 (d, J=6.8 Hz, 3H); MS m/z 368 (M+H)$^+$; Anal. calcd for C$_{20}$H$_{25}$N$_5$O$_2$: C, 65.37; H, 6.86; N, 19.06. Found: C, 65.14; H, 6.90; N, 18.82.

Examples 7-18

A reagent from the table below (0.11 mmol) was added to a test tube containing a solution of (11S)-11-(3-aminopropyl)-10,11-dihydro-8H-[1,4]oxazino[4',3':1,2]imidazo[4,5-c]quinolin-6-amine (26.8 mg, 1.0 equivalent, 0.090 mmol) and triethylamine (0.0157 mL, 0.11 mmol) in chloroform (1 mL). The test tube was capped and placed on a shaker at ambient temperature overnight (approximately 18 hours). The solvent was removed from the test tube by vacuum centrifugation. For Examples 11, 12, 17, and 18, additional chloroform (1 mL), triethylamine (0.035 mL, 0.25 mmol), and reagent from the table below (0.11 mmol) were added, and each reaction was sonicated with heating for 30 minutes. The solvent was removed from the test tube by vacuum centrifugation. The compounds were purified by reversed phase preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent used for each example, the structure of the resulting compound, and the observed accurate mass for the isolated trifluoroacetate salt.

Examples 7-18

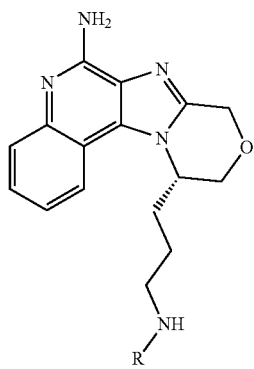

| Example | Reagent | R | Measured Mass (M + H) |
|---|---|---|---|
| 7 | None | H— | 298.1653 |
| 8 | Acetyl chloride | H$_3$C—C(=O)— | 340.1765 |

-continued
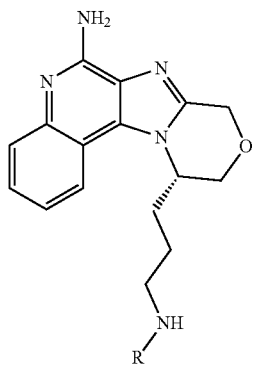
| Example | Reagent | R | Measured Mass (M + H) |
|---|---|---|---|
| 9 | Cyclopropanecarbonyl chloride | 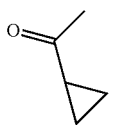 | 366.1922 |
| 10 | Benzoyl choride | 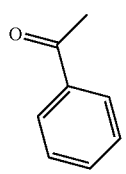 | 402.1914 |
| 11 | Nicotinoyl chloride hydrochloride | 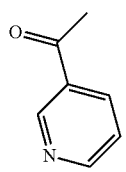 | 403.1886 |
| 12 | Dimethylsulfamoyl chloride | 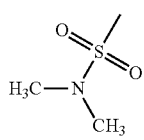 | 405.1706 |
| 13 | Benzenesulfonyl chloride | 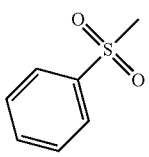 | 438.1609 |
| 14 | 1-Methylimidazole-4-sulfonyl chloride | 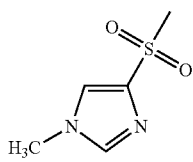 | 442.1660 |
| 15 | Isopropyl isocyanate | 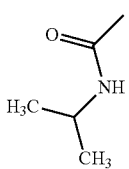 | 383.2197 |

-continued

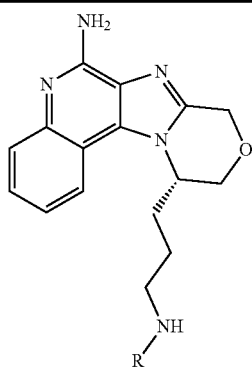

| Example | Reagent | R | Measured Mass (M + H) |
|---|---|---|---|
| 16 | Phenyl isocyanate | 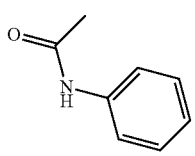 | 417.2014 |
| 17 | N,N-Dimethylcarbamoyl chloride | 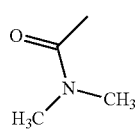 | 369.2004 |
| 18 | 1-Piperidinecarbonyl chloride | 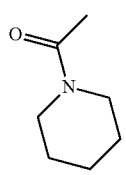 | 409.2348 |

Examples 19-28

(11S)-11-(3-Aminopropyl)-10,11-dihydro-8H-[1,4]oxazino[4',3':1,2]imidazo[4,5-c]quinolin-6-amine was reduced according to the method of Example 3 to provide (11S)-11-(3-aminopropyl)-2,3,4,8,10,11-hexahydro-8H-[1,4]oxazino[4',3':1,2]imidazo[4,5-c]quinolin-6-amine dihydrochloride. A reagent from the table below (0.11 mmol) was added to a test tube containing a solution of (11S)-11-(3-aminopropyl)-2,3,4,8,10,11-hexahydro-8H-[1,4]oxazino[4',3':1,2]imidazo[4,5-c]quinolin-6-amine dihydrochloride (38.5 mg, 1.0 equivalent, 0.10 mmol), 1,8-diazabicyclo[5.4.0]undec-7-ene (DBU) (0.0308 mL, 0.20 mmol), and N,N-diisopropylethylamine (0.0269 mL, 0.15 mmol) in N,N-dimethylacetamide (DMA) (1 mL). The test tube was capped and placed on a shaker at ambient temperature overnight (approximately 18 hours). Two drops of water were added to each tube, and the solvent was removed from the test tube by vacuum centrifugation. The compounds were purified by reversed phase prep HPLC according to the method described in Examples 7-18. The table below shows the reagent used for each example, the structure of the resulting compound, and the observed accurate mass for the isolated trifluoroacetate salt.

Examples 19-28
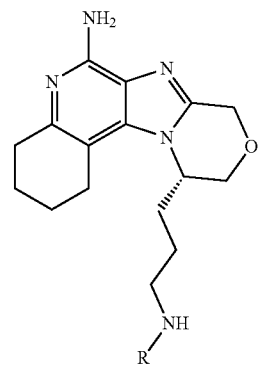
| Example | Reagent | R | Measured Mass (M + H) |
|---|---|---|---|
| 19 | None | H— | 302.1981 |
| 20 | Acetyl chloride | —C(O)CH₃ | 344.2065 |
| 21 | Cyclopropanecarbonyl chloride | —C(O)-cyclopropyl | 370.2263 |
| 22 | Dimethylsulfamoyl chloride | —S(O)₂N(CH₃)₂ | 409.2024 |
| 23 | Benzenesulfonyl chloride | —S(O)₂Ph | 442.1925 |
| 24 | 1-Methylimidazole-4-sulfonyl chloride | —S(O)₂(1-methylimidazol-4-yl) | 446.1962 |
| 25 | Isopropyl isocyanate | —C(O)NHCH(CH₃)₂ | 387.2511 |
| 26 | Phenyl isocyanate | —C(O)NHPh | 421.2353 |
| 27 | N,N-Dimethylcarbamoyl chloride | —C(O)N(CH₃)₂ | 373.2342 |

-continued

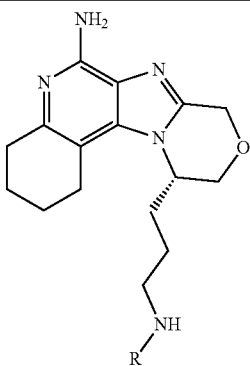

| Example | Reagent | R | Measured Mass (M + H) |
|---|---|---|---|
| 28 | 1-Piperidinecarbonyl chloride | 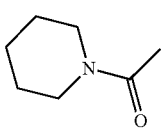 | 413.2669 |

Example 29

N-{3-[(11S)-6-Amino-9-(methylsulfonyl)-8,9,10,11-tetrahydropyrazino[1',2':1,2]imidazo[4,5-c]quinolin-11-yl]propylmethanesulfonamide

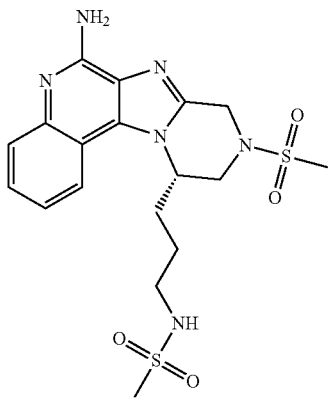 [SMILES: CS(=O)(=O)NCCC[C@H]1CN(S(C)(=O)=O)Cc2nc3c(N)nc4ccccc4c3n21]

Part A

[4-tert-Butoxycarbonylamino-1S-(hydroxymethyl)butyl]carbamic acid benzyl ester (10.97 g, 31.2 mmol) was dissolved in 400 mL of $CH_2Cl_2$ and treated with triethylamine (8.68 mL, 62.4 mmol), methanesulfonyl chloride (3.93 g, 34.3 mmol) and DMAP (100 mg, 0.82 mmol). The reaction mixture was stirred stir under $N_2$ for 1 hour. The reaction mixture was then treated with 200 mL of saturated sodium bicarbonate solution and the layers were separated. The organic portion was washed successively with 3.5% $NaH_2PO_4$ solution (3×100 mL), $H_2O$ (100 mL) and brine (100 mL). The organic portion was dried over $Na_2SO_4$, filtered and concentrated under reduced pressure to give methanesulfonic acid (2S-benzyloxycarbonylamino-5-tert-butoxycarbonylamino)pentyl ester (13.21 g) as a pink solid.

Part B

Methanesulfonic acid (2S-benzyloxycarbonylamino-5-tert-butoxycarbonylamino)pentyl ester (13.21 g, 30.7 mmol) was dissolved in 100 mL of N,N-dimethylformamide (DMF) and treated with sodium azide (2.40 g, 36.9 mmol). The reaction mixture was heated to 60° C. and stirred under $N_2$ overnight. The reaction mixture was concentrated under reduced pressure to give a white, sticky foam which was dissolved in 250 mL of ethyl acetate and washed successively with $H_2O$ (3×100 mL) and brine (100 mL). The organic portion was dried over $Na_2SO_4$, filtered and concentrated under reduced pressure to give a colorless syrup. Chromatography ($SiO_2$, 25-50% ethyl acetate/hexanes) gave [(1S-azidomethyl-4-tert-butoxycarbonylamino)butyl]carbamic acid benzyl ester (10.13 g) as a colorless syrup.

Part C

[(1S-Azidomethyl-4-tert-butoxycarbonylamino)butyl]carbamic acid benzyl ester (10.13 g, 26.9 mmol) was dissolved in 200 mL of THF and the solution was treated with 5 mL of $H_2O$. Triphenylphosphine (7.39 g, 28.2 mmol) was then added and the reaction mixture was heated to reflux overnight. The reaction mixture was then concentrated under reduced pressure. Chromatography ($SiO_2$, 33-50% CMA/$CHCl_3$) gave [(1S-aminomethyl-4-tert-butoxycarbonylamino)butyl]carbamic acid benzyl ester (9.13 g) as a colorless syrup.

Part D

[(1S-Aminomethyl-4-tert-butoxycarbonylamino)butyl]carbamic acid benzyl ester (9.45 g, 26.8 mmol) was dissolved in 270 mL of anhydrous $CH_2Cl_2$. The solution was treated with triethylamine (7.47 mL, 53.6 mmol) and cooled to 0° C. under $N_2$. Methanesulfonyl chloride (2.08 mL, 26.8 mmol) was then added and the reaction mixture was stirred for 1 hour. The reaction mixture was then treated with saturated sodium bicarbonate solution and the layers were separated. The organic portion was washed successively with $H_2O$ and brine. The organic portion was dried over $Na_2SO_4$, filtered and concentrated under reduced pressure to give {[4-tert-butoxycarbonylamino-1S-(methanesulfonylamino)methyl]butyl}carbamic acid benzyl ester (10.25 g) as white solid.

Part E

{[4-tert-Butoxycarbonylamino-1S-(methanesulfonylamino)methyl]butyl}carbamic acid benzyl ester (10.25 g, 23.9 mmol) was dissolved in 150 mL of methanol and the solution was placed in a pressure bottle. Palladium on carbon (10%, 1.0 g) was then added and the reaction mixture was shaken under H₂ at 50 PSI (3.4×10⁵ Pa). After 7 hours, the reaction mixture was treated with an additional 1.0 g of catalyst and shaking was continued overnight. The reaction mixture was then filtered through a pad of CELITE filter agent. The pad was rinsed with methanol and the combined filtrates were concentrated under reduced pressure to give tert-butyl (4S)-4-amino-5-[(methylsulfonyl)amino]pentylcarbamate (6.88 g) as a white solid.

Part F tert-Butyl (4S)-4-amino-5-[(methylsulfonyl)amino]pentylcarbamate (6.88 g, 23.3 mmol) was dissolved in 100 mL of dry CH₂Cl₂ and the solution was cooled to 0° C. under N₂. Triethylamine (6.49 mL, 46.6 mmol) and 4-chloro-3-nitroquinoline (4.85 g, 23.3 mmol) were then added and the reaction was allowed to warm to ambient temperature and stirred for 2 days. The reaction mixture was then concentrated under reduced pressure to give a yellow solid. The solid was triturated with 100 mL of hot H₂O with stirring. The suspension was cooled and filtered to give 12.0 g of a pasty, yellow solid. The pasty solid was dissolved in methanol and CHCl₃ and concentrated to give a yellow solid. The solid was then stirred in 100 mL of hot CHCl₃, cooled and the solid was collected by filtration to give tert-butyl (4S)-5-[(methylsulfonyl)amino]-4-[(3-nitroquinolin-4-yl)amino]pentylcarbamate (8.00 g) as a yellow powder.

Part G tert-Butyl (4S)-5-[(methylsulfonyl)amino]-4-[(3-nitroquinolin-4-yl)amino]pentylcarbamate (8.00 g, 17.1 mmol) was dissolved in 150 mL of acetonitrile and the solution was placed in a pressure bottle. Platinum on carbon (5%, 2.0 g) was then added and the reaction mixture was shaken under H₂ at 50 PSI (3.4×10⁵ Pa). After 2 hours, the reaction mixture was then filtered through a pad of CELITE filter agent. The pad was rinsed with acetonitrile and the combined filtrates were concentrated under reduced pressure to give tert-butyl (4S)-4-[(3-aminoquinolin-4-yl)amino]-5-[(methylsulfonyl) amino]pentylcarbamate (7.13 g) as an orange foam.

Part H tert-Butyl (4S)-4-[(3-aminoquinolin-4-yl)amino]-5-[(methylsulfonyl)amino]pentylcarbamate (7.13 g, 16.3 mmol) was dissolved in 100 mL of anhydrous 1,2-dichloroethane and the solution was stirred under N₂. Ethyl 2-chloroethanimidoate hydrochloride (7.73 g, 48.9 mmol) was then added and the reaction mixture was heated to 65° C. After stirring overnight, the reaction mixture was cooled and treated with 100 mL of saturated NaHCO₃ solution and 200 mL of CHCl₃. The layers were separated and the organic portion was washed successively with H₂O and brine. The organic portion was dried over Na₂SO₄, filtered and concentrated under reduced pressure to give tert-butyl (4S)-4-[2-(chloromethyl)-1H-imidazo[4,5-c]quinolin-1-yl]-5-[(methylsulfonyl) amino]pentylcarbamate (8.08 g) as an orange foam. The crude material was used in the next step without further purification.

Part I tert-Butyl (4S)-4-[2-(chloromethyl)-1H-imidazo[4,5-c] quinolin-1-yl]-5-[(methylsulfonyl)amino]pentylcarbamate (8.08 g, 16.3 mmol) was dissolved in 200 mL of CH₂Cl₂ and treated with 1,8-diazabicyclo[5.4.0]undec-7-ene (DBU) (2.91 mL, 19.5 mmol) After 1 hour, the reaction mixture was washed successively with H₂O and brine and the organic layer was dried over Na₂SO₄, filtered and concentrated under reduced pressure. Chromatography (SiO₂, 3% methanol/ CHCl₃) gave tert-butyl 3-[(11S)-9-(methylsulfonyl)-8,9,10, 11-tetrahydropyrazino[1',2':1,2]imidazo[4,5-c]quinolin-11-yl]propylcarbamate (6.16 g) as a light yellow foam.

Part J tert-Butyl 3-[(11S)-9-(methylsulfonyl)-8,9,10,11-tetrahydropyrazino[1',2':1,2]imidazo[4,5-c]quinolin-11-yl]propylcarbamate (6.16 g, 13.4 mmol) was dissolved in 110 mL of CH₂Cl₂ and treated with MCPBA (4.05 g, 57-86% pure material). After stirring for 1 hour, the reaction mixture was treated with 100 mL of 5% Na₂CO₃ solution and the layers were separated. The aqueous layer was then extracted with CH₂Cl₂ (2×50 mL). The combined organic layers were concentrated under reduced pressure to give tert-butyl 3-[(11S)-9-(methylsulfonyl)-5-oxido-8,9,10,11-tetrahydropyrazino[1',2':1,2] imidazo[4,5-c]quinolin-11-yl]propylcarbamate (6.37 g) as a golden foam.

Part K tert-Butyl 3-[(11S)-9-(methylsulfonyl)-5-oxido-8,9,10, 11-tetrahydropyrazino[1',2':1,2]imidazo[4,5-c]quinolin-11-yl]propylcarbamate (6.37 g, 13.4 mmol) was dissolved in 120 mL of CH₂Cl₂ and treated with 12 mL of concentrated NH₄OH solution. The mixture was stirred rapidly and then p-toluenesulfonyl chloride (2.81 g, 14.7 mmol) was carefully added. Rapid stirring was continued for 3 hours. The reaction mixture was treated with 100 mL of CH₂Cl₂ and 25 mL of H₂O. The layers were separated and the organic portion was washed successively with 2% Na₂CO₃ solution (3×50 mL), H₂O and brine. The organic portion was dried over Na₂SO₄, filtered and concentrated under reduced pressure. Chromatography (SiO₂, 33% CMA/CHCl₃) gave tert-butyl 3-[(11S)-6-amino-9-(methylsulfonyl)-8,9,10,11-tetrahydropyrazino [1',2':1,2]imidazo[4,5-c]quinolin-11-yl]propylcarbamate (5.41 g) as light-orange foam.

Part L tert-Butyl 3-[(11S)-6-amino-9-(methylsulfonyl)-8,9,10, 11-tetrahydropyrazino[1',2':1,2]imidazo[4,5-c]quinolin-11-yl]propylcarbamate (5.41 g, 11.4 mmol) was dissolved in 25 mL of ethanol and 25 mL of a 1.8 M solution of HCl in ethanol was added. The reaction mixture was heated to 75° C. After 1 hour, the reaction mixture was cooled and filtered to give a white solid. The resulting solid was stirred in refluxing ethanol for 30 minutes. The suspension was cooled and filtered to give a white solid. The solid was washed with a small portion of cold ethanol and then dried by suction to give (11S)-11-(3-aminopropyl)-9-(methylsulfonyl)-8,9,10,11-tetrahydropyrazino[1',2':1,2]imidazo[4,5-c]quinolin-6-amine dihydrochloride hydrate (2.98 g) as an off-white powder (Anal. calcd for C₁₇H₂₂N₆O₂S₂.2.0 HCl.1.0H₂O: C, 43.87; H, 5.63; N, 18.06. Found: C, 43.83; H, 5.53; N, 17.99). The free base could be prepared by dissolving the material in dilute NH₄OH solution and extraction into CHCl₃.

Part M (11S)-11-(3-Aminopropyl)-9-(methylsulfonyl)-8,9,10, 11-tetrahydropyrazino[1',2':1,2]imidazo[4,5-c]quinolin-6-amine (400 mg, 1.07 mmol) was dissolved in 10 mL of CH₂Cl₂ and the reaction mixture was cooled to 0° C. under N₂. Triethylamine (298 µL, 2.14 mmol) was added followed by methanesulfonyl chloride (91 L, 1.08 mmol). After stirring for 60 minutes, the reaction mixture was treated with saturated sodium bicarbonate solution and 5 mL of methanol. The layers were separated and the aqueous portion was extracted with 10% methanol/CHCl₃ (3×20 mL). The combined organic layers were washed with 10 mL of brine. The organic portion was dried over Na₂SO₄, filtered and concentrated under reduced pressure. Chromatography (SiO₂, 50% CMA/ CHCl₃) gave the desired material as a white powder. Crystallization from propyl acetate/methanol gave N-{3-[(11S)-6-amino-9-(methylsulfonyl)-8,9,10,11-tetrahydropyrazino[1', 2':1,2]imidazo[4,5-c]quinolin-11-yl] propylmethanesulfonamide (239 mg) as an amber solid, mp 224-226° C.

¹H NMR (300 MHz, DMSO-d₆) δ 7.98 (d, J=7.8 Hz, 1H), 7.64 (dd, J=1.0, 8.3 Hz, 1H), 7.45 (ddd, J=1.0, 7.0, 8.2 Hz, 1H), 7.30 (ddd, J=1.1, 7.0, 8.1 Hz, 1H), 7.03 (t, J=5.9 Hz, 1H), 6.62 (s, 2H), 5.19 (m, 1H), 4.79 (d, J=15.6 Hz, 1H), 4.62 (d, J=15.6 Hz, 1H), 4.04 (d, J=13.6 Hz, 1H), 3.58 (dd, J=2.7, 13.0 Hz, 1H), 3.11 (s, 3H), 2.98 (m, 2H), 2.93 (s, 3H), 2.00-1.65 (m, 4H); ¹³C NMR (125 MHz, DMSO-d₆) δ 152.1, 145.2, 143.9, 131.6, 127.1, 127.1, 126.6, 121.8, 120.7, 114.8, 54.4, 49.0, 45.2, 45.1, 42.6, 35.7, 29.7, 25.7; MS m/z 453 (M+H)⁺.

Anal. calcd for $C_{18}H_{24}N_6O_4S_2 \cdot 0.25H_2O$: C, 47.30; H, 5.40; N, 18.39. Found: C, 46.93; H, 5.00; N, 18.02.

Example 30

N-{3-[(11S)-6-Amino-9-(methylsulfonyl)-8,9,10,11-tetrahydropyrazino[1',2':1,2]imidazo[4,5-c]quinolin-11-yl]propyl}morpholine-4-carboxamide

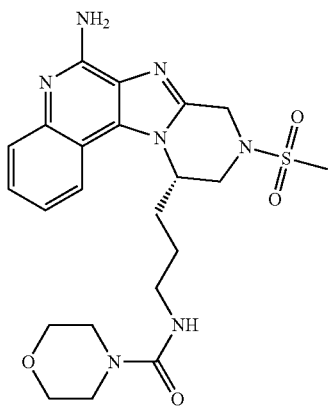 [SMILES: CS(=O)(=O)N1Cc2nc3c(N)nc4ccccc4c3n2[C@@H](CCCNC(=O)N2CCOCC2)C1]

(11S)-11-(3-Aminopropyl)-9-(methylsulfonyl)-8,9,10,11-tetrahydropyrazino[1',2':1,2]imidazo[4,5-c]quinolin-6-amine dihydrochloride hydrate (465 mg, 1.00 mmol) was suspended in 20 mL of $CH_2Cl_2$ and the reaction mixture was cooled to 0° C. under $N_2$. Triethylamine (696 mL, 5.0 mmol) was added followed by morpholinecarbonyl chloride (128 mL, 1.10 mmol). After stirring overnight, the reaction mixture was treated with DBU (448 mL, 3.0 mmol) and an additional 83 µL of morpholinecarbonyl chloride and stirring was continued at 0° C. for 4 hours. An additional 50 µL of morpholinecarbonyl chloride was added and stirring was continued at 0° C. overnight. The reaction mixture was then treated with saturated sodium bicarbonate solution and 5 mL of methanol. The layers were separated, and the organic layer was washed successively with $H_2O$ and brine. The organic portion was dried over $Na_2SO_4$, filtered and concentrated under reduced pressure. Chromatography ($SiO_2$, 50% CMA/$CHCl_3$) gave the desired material as a white solid with a minor impurity. Additional column chromatography (15-20% methanol/$CHCl_3$) gave the purified product as a white solid. Crystallization from propyl acetate/methanol gave N-{3-[(11S)-6-amino-9-(methylsulfonyl)-8,9,10,11-tetrahydropyrazino[1',2':1,2]imidazo[4,5-c]quinolin-11-yl]propyl}morpholine-4-carboxamide (293 mg) as a white solid, mp 175-176° C.

$^1$H NMR (300 MHz, DMSO-$d_6$) δ 7.90 (d, J=7.8 Hz, 1H), 7.64 (dd, J=1.0, 8.3 Hz, 1H), 7.46 (ddd, J=1.0, 7.2, 8.2 Hz, 1H), 7.25 (ddd, J=1.1, 7.1, 8.1 Hz, 1H), 6.61 (s, 2H), 6.52 (t, J=5.4 Hz, 1H), 5.12 (m, 1H), 4.77 (d, J=15.4 Hz, 1H), 4.61 (d, J=15.6 Hz, 1H), 4.02 (d, J=13.0 Hz, 1H), 3.56 (dd, J=3.0, 13.0 Hz, 1H), 3.44 (t, J=4.8 Hz, 4H), 3.13 (s, 3H), 3.01-3.17 (m, 6H), 2.00-1.56 (m, 4H); $^{13}$C NMR (125 MHz, DMSO-$d_6$) δ 157.9, 152.1, 145.2, 143.9, 131.6, 127.1, 127.0, 126.7, 121.7, 120.5, 114.8, 66.2, 54.7, 45.2, 45.1, 44.1, 35.7, 29.8, 26.2; MS m/z 488 (M+H)$^+$. Anal. calcd for $C_{22}H_{29}N_7O_4S \cdot 0.4H_2O$: C, 53.40; H, 6.07; N, 19.82. Found: C, 53.68; H, 6.15; N, 19.42.

Example 31

N-{3-[(11S)-6-Amino-9-(methylsulfonyl)-1,2,3,4,8,9,10,11-octahydropyrazino[1',2':1,2]imidazo[4,5-c]quinolin-11-yl]propyl}methanesulfonamide

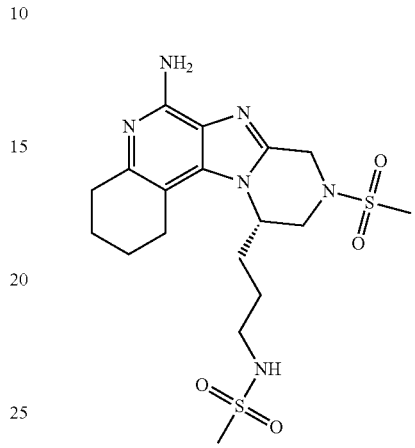

Part A (11S)-11-(3-Aminopropyl)-9-(methylsulfonyl)-8,9,10,11-tetrahydropyrazino[1',2':1,2]imidazo[4,5-c]quinolin-6-amine dihydrochloride hydrate (1.30 g, 2.80 mmol) was dissolved in 10 mL of trifluoroacetic acid and the solution was placed in a pressure bottle. Platinum oxide (635 mg) was then added and the reaction mixture was shaken under $H_2$ at 50 PSI ($3.4 \times 10^5$ Pa). After 2 days, the reaction mixture was filtered through a pad of CELITE filter agent. The pad was rinsed with ethanol and the combined filtrates were concentrated under reduced pressure. The resulting residue was concentrated with 2 N HCl in ethanol three times to give white solid. The white solid was treated with hot 2 N HCl in ethanol and the solution was allowed to cool, leaving a white solid. The solid was isolated by filtration and rinsed with ethanol and dried under vacuum at 80° C. to give (11.5)-11-(3-aminopropyl)-9-(methylsulfonyl)-1,2,3,4,8,9,10,11-octahydropyrazino[1',2':1,2]imidazo[4,5-c]quinolin-6-amine dihydrochloride hydrate (800 mg) as an off-white powder.

Anal. calcd for $C_{17}H_{22}N_6O_2S_2 \cdot 2.0 HCl \cdot 1.5H_2O$: C, 42.68; H, 6.53; N, 17.57. Found: C, 42.86; H, 6.56; N, 16.96.

Part B (11S)-11-(3-Aminopropyl)-9-(methylsulfonyl)-1,2,3,4,8,9,10,11-octahydropyrazino[1',2':1,2]imidazo[4,5-c]quinolin-6-amine dihydrochloride hydrate (235 mg, 0.49 mmol) was dissolved in 10 mL of $CH_2Cl_2$ and the reaction mixture was cooled to 0° C. under $N_2$. Triethylamine (362 µL, 2.60 mmol) and DBU (155 µL, 1.04 mmol) were added followed by methanesulfonyl chloride (40 µL, 0.57 mmol). After stirring for 90 minutes, the reaction mixture was treated with an additional 20 µL of methanesulfonyl chloride and the reaction was stirred overnight. An additional 40 µL of methanesulfonyl chloride was added and stirring was continued for 4 hours. The reaction mixture was treated with saturated sodium bicarbonate solution and 50 mL of 10% methanol/$CHCl_3$. The organic layer was washed successively with $H_2O$ and brine. The organic portion was dried over $Na_2SO_4$, filtered and concentrated under reduced pressure. Chromatography ($SiO_2$, 50% CMA/$CHCl_3$) gave the desired material as a light-yellow powder. Crystallization from propyl acetate/methanol gave N-{3-[(11S)-6-amino-9-(methylsulfonyl)-1,2,3,4,8,9,10,11-octahydropyrazino[1',2':1,2]imidazo[4,5-c]

quinolin-11-yl]propyl}methanesulfonamide (239 mg) as light-yellow crystals, mp 148-153° C.

$^1$H NMR (300 MHz, DMSO-$d_6$) δ 7.02 (t, J=5.9 Hz, 1H), 5.89 (s, 2H), 4.80 (m, 1H), 4.65 (d, J=15.5 Hz, 1H), 4.48 (d, J=15.6 Hz, 1H), 3.90 (d, J=13.0 Hz, 1H), 3.42 (m, 1H), 3.11 (s, 3H), 3.10-2.80 (m, 4H), 2.86 (s, 3H), 2.67 (m, 2H), 1.86-1.55 (m, 8H); $^{13}$C NMR (125 MHz, DMSO-$d_6$) δ 149.5, 146.6, 143.4, 137.2, 125.2, 105.7, 53.9, 45.2, 45.0, 42.5, 35.5, 32.4, 31.2, 25.9, 23.1, 23.0; MS m/z 457 (M+H)$^+$. Anal. calcd for $C_{18}H_{28}N_6O_4S_2 \cdot 0.70H_2O$: C, 46.08; H, 6.32; N, 17.91. Found: C, 45.77; H, 6.29; N, 18.11.

Example 32

N-{3-[(11S)-6-Amino-9-(methylsulfonyl)-1,2,3,4,8,9,10,11-octahydropyrazino[1',2':1,2]imidazo[4,5-c]quinolin-11-yl]propyl}morpholine-4-carboxamide

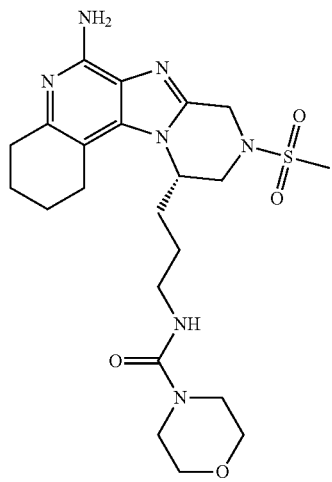 [SMILES: CS(=O)(=O)N1Cc2nc3c(N)nc4c(c3n2[C@@H](CCCNC(=O)N2CCOCC2)C1)CCCC4]

(11S)-11-(3-Aminopropyl)-9-(methylsulfonyl)-1,2,3,4,8,9,10,11-octahydropyrazino[1',2':1,2]imidazo[4,5-c]quinolin-6-amine dihydrochloride hydrate (300 mg, 0.63 mmol) was dissolved in 10 mL of $CH_2Cl_2$ and the reaction mixture was cooled to 0° C. under $N_2$. Triethylamine (463 μL, 3.33 mmol) and DBU (199 μL, 1.33 mmol) were added followed by morpholine carbonyl chloride (232 μL, 2.00 mmol). After stirring overnight, the reaction mixture was treated with saturated sodium bicarbonate solution and 50 mL of 10% methanol/$CHCl_3$. The organic layer was washed successively with $H_2O$ and brine. The organic portion was dried over $Na_2SO_4$, filtered and concentrated under reduced pressure. Chromatography ($SiO_2$, 50% CMA/$CHCl_3$) gave the desired material as a light-yellow solid. A second column chromatography (7:2:0.25 $CHCl_3$/MeOH/$H_2O$) gave N-{3-[(11S)-6-amino-9-(methylsulfonyl)-1,2,3,4,8,9,10,11-octahydropyrazino[1',2':1,2]imidazo[4,5-c]quinolin-11-yl]propyl}morpholine-4-carboxamide (112 mg) as an off-white powder, mp 149-160° C.

$^1$H NMR (300 MHz, DMSO-$d_6$) δ 6.57 (t, J=5.5 Hz, 1H), 5.88 (s, 2H), 4.75 (m, 1H), 4.65 (d, J=15.6 Hz, 1H), 4.48 (d, J=15.5 Hz, 1H), 3.89 (d, J=12.8 Hz, 1H), 3.52 (m, 4H), 3.35 (m, 1H), 3.21 (m, 4H), 3.10 (s, 3H), 3.12-2.80 (m, 4H), 2.75 (m, 2H), 1.90-1.52 (m, 8H); $^{13}$C NMR (125 MHz, DMSO-$d_6$) δ 158.0, 149.6, 146.5, 143.4, 137.2, 125.2, 105.6, 66.3, 54.2, 45.2, 45.0, 44.2, 35.5, 32.4, 31.4, 26.2, 23.1, 23.0; MS m/z 492 (M+H)$^+$. Anal. calcd for $C_{22}H_{33}N_7O_4S \cdot 0.7H_2O$: C, 52.41; H, 6.88; N, 19.45. Found: C, 52.40; H, 6.86; N, 19.34.

Examples 33-53

A reagent from the table below (0.11 mmol, 1.1 equivalents) was added to a test tube containing a solution of (11S)-11-(3-aminopropyl)-9-(methylsulfonyl)-8,9,10,11-tetrahydropyrazino[1',2':1,2]imidazo[4,5-c]quinolin-6-amine dihydrochloride (45.5 mg, 0.10 mmol), DBU (0.029 mL, 0.20 mmol), and N,N-diisopropylethylamine (0.0255 mL, 0.15 mmol) in DMA (1 mL). The reaction was shaken at room temperature for four hours. Two drops of water were added to each tube, and the solvent was removed by vacuum centrifugation. The examples were purified by prep HPLC according to the method described in Examples 7-18. The table below shows the reagent used for each example, the structure of the resulting compound, and the observed accurate mass for the isolated trifluoroacetate salt.

Examples 33-53

| Example | Reagent | R | Measured Mass (M + H) |
|---------|---------|---|-----------------------|
| 33 | None | H– | 375.1603 |
| 34 | Acetyl chloride | CH₃C(O)– | 417.1710 |
| 35 | Methyl chloroformate | H₃COC(O)– | 433.1676 |
| 36 | Cyclopropanecarbonyl chloride | cyclopropyl-C(O)– | 443.1876 |
| 37 | Benzoyl chloride | PhC(O)– | 479.1887 |
| 38 | Isonicotinoyl chloride | 4-pyridyl-C(O)– | 480.1812 |
| 39 | Nicotinoyl chloride | 3-pyridyl-C(O)– | 480.1840 |

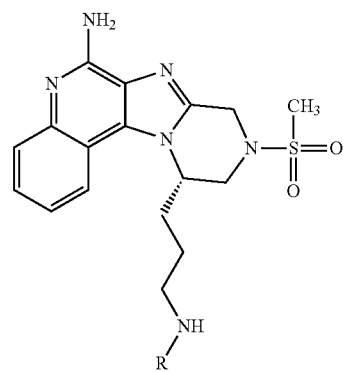

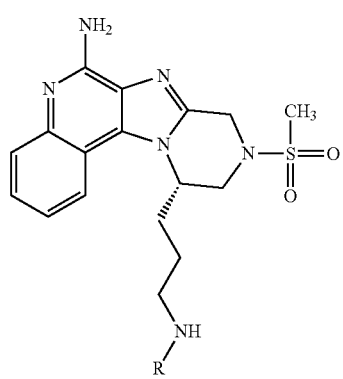

| Example | Reagent | R | Measured Mass (M + H) |
|---|---|---|---|
| 40 | trans-2-Phenyl-1-cyclopropane-carbonyl chloride | | 519.2158 |
| 41 | Methanesulfonyl chloride | | 453.1391 |
| 42 | Isopropylsulfonyl chloride | | 481.1698 |
| 43 | Dimethylsulfamoyl chloride | | 482.1630 |
| 44 | Benzenesulfonyl chloride | | 515.1536 |
| 45 | 1-Methylimidazole-4-sulfonyl chloride | | 519.1589 |
| 46 | alpha-Toluenesulfonyl chloride | | 529.1715 |
| 47 | Methyl isocyanate | | 432.1826 |

| Example | Reagent | R | Measured Mass (M + H) |
|---|---|---|---|
| 48 | Isopropyl isocyanate | | 460.2087 |
| 49 | Phenyl isocyanate | | 494.1966 |
| 50 | N,N-Dimethylcarbamoyl chloride | | 446.1991 |
| 51 | 1-Piperidinecarbonyl chloride | | 486.2288 |
| 52 | 4-Morpholinylcarbonyl chloride | | 488.2088 |
| 53 | 4-Methyl-1-Piperazinecarbonyl chloride | | 501.2392 |

Examples 54-66

(11S)-11-(3-Aminopropyl)-9-(methylsulfonyl)-1,2,3,4,8,9,10,11-octahydropyrazino[1',2':1,2]imidazo[4,5-c]quinolin-6-amine dihydrochloride hydrate was treated according to the reaction and purification methods described in Examples 19-28. The table below shows the reagent used for each example, the structure of the resulting compound, and the observed accurate mass for the isolated trifluoroacetate salt.

Examples 54-66

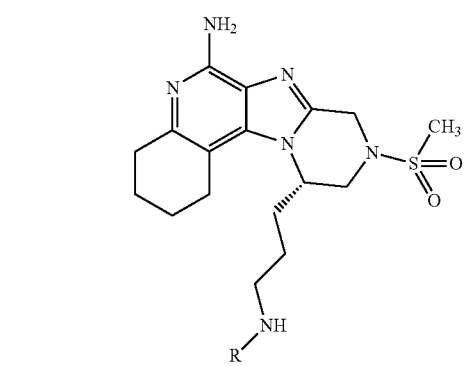

| Example | Reagent | R | Measured Mass (M + H) |
|---|---|---|---|
| 54 | None | H– | 379.1901 |
| 55 | Acetyl chloride | –C(O)CH₃ | 421.2023 |
| 56 | Cyclopropane-carbonyl chloride | –C(O)-cyclopropyl | 447.2181 |
| 57 | Benzoyl chloride | –C(O)Ph | 483.2187 |
| 58 | Nicotinoyl chloride | –C(O)-pyridyl | 484.2116 |
| 59 | Methanesulfonyl chloride | –S(O)₂CH₃ | 457.1705 |
| 60 | Dimethylsulfamoyl chloride | –S(O)₂N(CH₃)₂ | 486.1987 |
| 61 | Benzenesulfonyl chloride | –S(O)₂Ph | 519.1887 |
| 62 | 1-Methylimidazole-4-sulfonyl chloride | –S(O)₂-(1-methylimidazol-4-yl) | 523.1916 |
| 63 | Isopropyl isocyanate | –C(O)NH-iPr | 464.2440 |
| 64 | Phenyl isocyanate | –C(O)NHPh | 498.2281 |
| 65 | N,N-Dimethylcarbamoyl chloride | –C(O)N(CH₃)₂ | 450.2285 |
| 66 | 1-Piperidinecarbonyl chloride | –C(O)-piperidinyl | 490.2587 |

Examples 67-71

The methods described in Examples 1 through 4 and 6 were followed using the opposite enantiomer of the relevant reagent described in those examples. The table below shows the structure of the resultant compound and its characterization data.

| Ex. | Structure | form | mp (° C.) | Anal. |
|---|---|---|---|---|
| 67 | 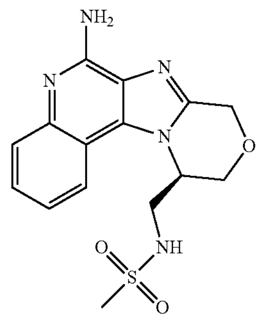 [SMILES: CS(=O)(=O)NC[C@@H]1COCc2nc3c(N)nc4ccccc4c3n21] | Off-white needles | 285-288 | Calcd for $C_{15}H_{17}N_5O_3S$: C, 51.86; H, 4.93; N, 20.16. Found: C, 49.43; H, 4.45; N, 19.37. |
| 68 | 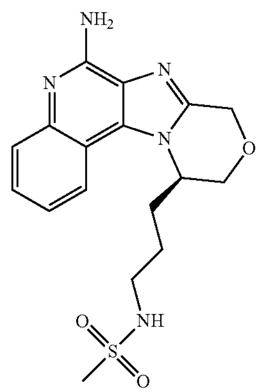 [SMILES: CS(=O)(=O)NCCC[C@@H]1COCc2nc3c(N)nc4ccccc4c3n21] | Off-white needles | 249.5-250 | Calcd for $C_{17}H_{21}N_5O_3S$: C, 54.38; H, 5.64; N, 18.65. Found: C, 54.31; H, 5.75; N, 18.64. |
| 69 | 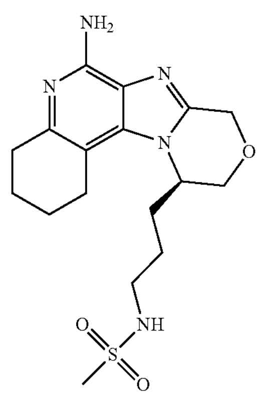 [SMILES: CS(=O)(=O)NCCC[C@@H]1COCc2nc3c(N)nc4c(c3n21)CCCC4] | White needles | 200-201 | Calcd for $C_{17}H_{25}N_5O_3S$: C, 53.81; H, 6.64; N, 18.45. Found: C, 53.69; H, 6.82; N, 18.39. |
| 70 | 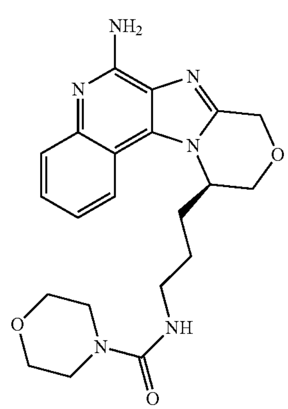 [SMILES: Nc1nc2ccccc2c2c1nc1n2[C@H](CCCNC(=O)N2CCOCC2)COC1] | Off-white needles | 221-222 | Calcd for $C_{21}H_{26}N_6O_3$: C, 61.45; H, 6.38; N, 20.47. Found: C, 60.15; H, 6.42; N, 20.27. |

-continued

| Ex. | Structure | form | mp (° C.) | Anal. |
|---|---|---|---|---|
| 71 | (structure shown) | White needles | 204.5-206 | Calcd for $C_{20}H_{25}N_5O_2$: C, 65.37; H, 6.86; N, 19.06. Found: C, 65.03; H, 6.96; N, 18.76. |

Examples 72-82

The methods described in Examples 7-18 were followed using (11R)-11-(3-aminopropyl)-10,11-dihydro-8H-[1,4]oxazino[4',3':1,2]imidazo[4,5-c]quinolin-6-amine, prepared according a modification of the method of Example 2, as the starting material. The table below shows the reagent used for each example, the structure of the resulting compound, and the observed accurate mass for the isolated trifluoroacetate salt.

Examples 72-82

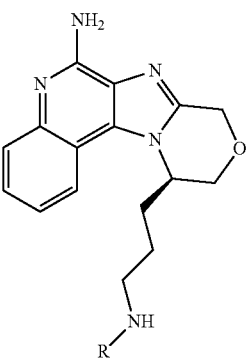

-continued

| Example | Reagent | R | Measured Mass (M + H) |
|---|---|---|---|
| 72 | None | H | 298.1651 |
| 73 | Acetyl chloride | (CH₃C(O)-) | 340.1747 |
| 74 | Cyclopropane-carbonyl chloride | (cyclopropyl-C(O)-) | 366.1944 |
| 75 | Benzoyl chloride | (PhC(O)-) | 402.1909 |
| 76 | Nicotinoyl chloride hydrochloride | (pyridyl-C(O)-) | 403.1892 |
| 77 | Dimethylsulfamoyl chloride | ((CH₃)₂N-SO₂-) | 405.1727 |
| 78 | Benzenesulfonyl chloride | (PhSO₂-) | 438.1579 |

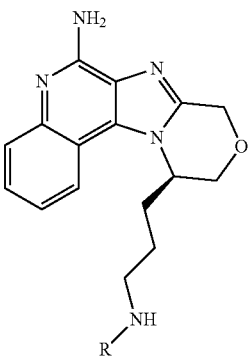

| Example | Reagent | R | Measured Mass (M + H) |
|---|---|---|---|
| 79 | Isopropyl isocyanate | ![structure] | 383.2189 |
| 80 | Phenyl isocyanate | ![structure] | 417.2045 |
| 81 | N,N-Dimethylcarbamoyl chloride | ![structure] | 369.2041 |
| 82 | 1-Piperidinecarbonyl chloride | ![structure] | 409.2319 |

Example 83

(11R)-11-[(Methylthio)methyl]-10,11-dihydro-8H-[1,4]oxazino[4',3':1,2]imidazo[4,5-c]quinolin-6-amine

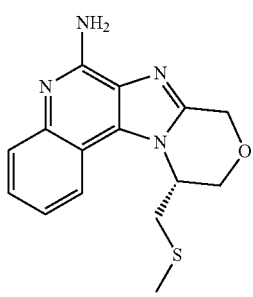 [SMILES: CSC[C@H]1COCc2nc3c(N)nc4ccccc4c3n21]

Part A

Chlorotriphenylmethane (265 g, 950 mmol) dissolved in 750 mL of dichloromethane was added dropwise to a stirred solution of L-serine methyl ester hydrochloride (148 g, 950 mmol) and triethylamine (260 mL, 1900 mmol) in 1.5 L of $CH_2Cl_2$ at 0° C. The cloudy yellow solution was stirred for 18 hours at ambient temperature. The reaction mixture was filtered to remove solids and the filtrate was washed with water. The organic layer was dried over $Na_2SO_4$, filtered, and concentrated under reduced pressure to give a yellow oil. The oil was concentrated from acetonitrile and then stirred in hexanes until a precipitate formed. The resulting solid was filtered to afford 310 g of methyl N-trityl-L-serinate as an off white powder.

Part B

Methyl N-trityl-L-serinate (136 g, 376 mmol) was dissolved in DMF (230 mL) and added dropwise to a stirred mixture of NaH (60% oil dispersion, 30.0 g, 752 mmol) and benzyl bromide (67.0 mL, 564 mmol) in 700 mL of DMF at 0° C. The resulting white suspension was stirred at 0° C. for 1 hour followed by the addition of saturated aqueous $NaHCO_3$ solution. The reaction mixture was diluted with $H_2O$ and extracted repeatedly with $Et_2O$. The combined organic layers were washed successively with $H_2O$ and brine, dried over $MgSO_4$ and concentrated under reduced pressure to give 137 g of methyl O-benzyl-N-trityl-L-threoninate as a cloudy oil.

Part C

Methyl O-benzyl-N-trityl-L-threoninate (137 g, 304 mmol) was dissolved in a minimal amount of $Et_2O$ and added dropwise to a mixture of lithium aluminum hydride (12.0 g, 333 mmol) and $Et_2O$ (1.5 L) at 0° C. The resulting mixture was stirred for 1 hour at 0° C. Ethyl acetate was then carefully added to the reaction mixture at 0° C. until no further gas evolution was observed and then the reaction mixture was treated with methanol until no further gas evolution was observed. The reaction mixture was then treated sequentially with $H_2O$ (12 mL), 6 M aqueous NaOH solution (12 mL), and $H_2O$ (36 mL) and stirred for 30 minutes. The resulting slurry was filtered through a pad of CELITE filter agent. The pad was rinsed repeatedly with $Et_2O$ and the combined filtrates were dried over $MgSO_4$ and concentrated under reduced pressure to give a colorless oil. The oil was dissolved in 90 mL of methanol and treated with 4M HCl in dioxane (227 mL, 908 mmol). The resulting homogeneous solution was stirred for 2 hours at ambient temperature. The solvent was then removed under reduced pressure to afford a yellow solid. The yellow solid was stirred in $Et_2O$ (500 mL) and filtered to give 43 g of (2R)-2-amino-3-(benzyloxy)propan-1-ol hydrochloride as a white crystalline solid.

Part D

4-Chloro-3-nitroquinoline (41.0 g, 197 mmol) was added to a mixture of (2R)-2-amino-3-(benzyloxy)propan-1-ol hydrochloride (43.0 g, 197 mmol) and triethylamine (69.0 mL, 494 mmol) dissolved in 985 mL of $CH_2Cl_2$ at 0° C. The resulting yellow mixture was stirred for 18 hours at ambient temperature. The solvent was then removed under reduced pressure to afford a yellow solid. The solid was stirred in $H_2O$ (100 mL) and filtered to give 57 g of (2R)-3-(benzyloxy)-2-[(3-nitroquinolin-4-yl)amino]propan-1-ol as a bright yellow solid.

Part E (2R)-3-(benzyloxy)-2-[(3-nitroquinolin-4-yl)amino]propan-1-ol (31 g, 87 mmol) was dissolved in a mixture of acetonitrile (810 mL) and isopropyl alcohol (90 mL) and the solution was placed in a pressure bottle. Platinum on carbon (5%, 3.1 g) was then added and the reaction mixture was shaken under $H_2$ at 48 PSI (3.3×10$^5$ Pa). After 2 hours, the reaction mixture was filtered through a pad of CELITE filter agent. The pad was rinsed with acetonitrile and the combined filtrates were concentrated under reduced pressure to give (2R)-2-[(3-aminoquinolin-4-yl)amino]-3-(benzyloxy)propan-1-ol (28 g) as an orange oil.

Part F

Chloroacetyl chloride (14.8 mL, 186 mol) was added to a mixture of (2R)-2-[(3-aminoquinolin-4-yl)amino]-3-(benzyloxy)propan-1-ol (28 g, 86 mmol) and triethylamine (12.0 mL, 86.5 mmol) dissolved in 432 mL of CH₂Cl₂ at 0° C. The reaction was stirred for 1 hour at ambient temperature. The solvent was removed under reduced pressure and the resulting dark, oily solid was treated with acetic acid (400 mL). The mixture was heated to reflux for 6 hours. The reaction was cooled to ambient temperature and the acetic acid was removed under reduced pressure. The resulting dark brown oil was concentrated from toluene (2×) and then from ethanol to afford a dark brown oil. The oil was dissolved in a mixture of ethanol (400 mL) and water (60 mL) and treated with potassium carbonate (60 g). The reaction mixture was heated at 60° C. and stirred for 1 hour. The reaction was then cooled to ambient temperature and filtered. The filtrate was concentrated under reduced pressure to afford a dark oil. Chromatography (SiO₂, 0-30% CMA/CHCl₃) gave 17 g of (11S)-11-[(benzyloxy)methyl]-10,11-dihydro-8H-[1,4]oxazino[4',3': 1,2]imidazo[4,5-c]quinoline as a light brown oil.

Part G

A solution of (11S)-11-[(benzyloxy)methyl]-10,11-dihydro-8H-[1,4]oxazino[4',3':1,2]imidazo[4,5-c]quinoline (3.7 g, 10 mmol) dissolved in CHCl₃ was treated with mCPBA (50% purity, 4.8 g, 13 mmol). The reaction was stirred at ambient temperature for 18 hours. Saturated aqueous NaHCO₃ (100 mL) and H₂O (50 mL) were then added to the reaction and the layers were separated. The aqueous layer was extracted with additional CHCl₃. The combined organic layers were dried over Na₂SO₄, filtered and concentrated under reduced pressure to give a black oil. The oil was dissolved in methanol (53 mL) and treated with concentrated NH₄OH solution (3.6 mL, 53 mmol). The solution was stirred and benzene sulfonyl chloride (2.9 mL, 53 mmol) was carefully added. The resulting reaction mixture was stirred at ambient temperature for 2 hours before adding additional concentrated NH₄OH solution (3.6 mL, 53 mmol) and benzene sulfonyl chloride (2.9 mL, 53 mmol). Stirring was continued for 18 hours and then reaction mixture was concentrated under reduced pressure. The resulting material was treated with saturated aqueous NaHCO₃ (50 mL) and H₂O (50 mL), and then extracted with CHCl₃. The organic layer was dried over Na₂SO₄, filtered and concentrated under reduced pressure to give a brown oil. The oil was treated with Et₂O and the mixture was stirred until a precipitate formed. The solid was isolated by filtration to give 3.1 g of (11S)-11-[(benzyloxy) methyl]-10,11-dihydro-8H-[1,4]oxazino[4',3':1,2]imidazo [4,5-c]quinolin-6-amine as a tan solid.

Part H (11S)-11-[(benzyloxy)methyl]-10,11-dihydro-8H-[1,4] oxazino[4',3':1,2]imidazo[4,5-c]quinolin-6-amine (4.5 g, 12 mmol) was added to a mixture of methanol (177 mL) and acetyl chloride (1.3 mL, 19 mmol) in a pressure bottle. Palladium on carbon (10%, 900 mg) was then added and the reaction mixture was shaken under H₂ at 48 PSI (3.3×10⁵ Pa). After 4 days, the reaction mixture was filtered through a pad of CELITE filter agent. The pad was rinsed with methanol and the combined filtrates were treated with 2 mL of 50% aqueous NaOH solution and the mixture was concentrated under reduced pressure to afford an oily solid. Chromatography (SiO₂, 0-30% CMA/CHCl₃) afforded an oil that was concentrated with acetonitrile to give 1.6 g of [(11S)-6-amino-10, 11-dihydro-8H-[1,4]oxazino[4',3':1,2]imidazo[4,5-c]quinolin-11-yl]methanol as a tan solid.

Part I

Thionyl chloride (1.5 mL, 20.7 mmol) was added neat to [(11S)-6-amino-10,11-dihydro-8H-[1,4]oxazino[4',3':1,2] imidazo[4,5-c]quinolin-11-yl]methanol (280 mg, 1.03 mmol). The nearly homogeneous yellow reaction mixture was heated to 70° C. for 2 hours and turned dark red. The reaction mixture was cooled to ambient temperature and poured over ice. While maintaining the temperature at 0° C., the pH of the mixture was brought to 14 with 50% aqueous NaOH. The resulting white suspension was extracted with CHCl₃. The layers were separated and the organic layer was dried over Na₂SO₄ and concentrated under reduced pressure to provide a tan foam. The tan foam was slurried with acetonitrile and filtered to give 185 mg of (11R)-11-(chloromethyl)-10,11-dihydro-8H-[1,4]oxazino[4',3':1,2]imidazo[4, 5-c]quinolin-6-amine as a white solid.

Part J

Sodium methyl thiolate (140 mg, 2.0 mmol) was added to a solution of (11R)-11-(chloromethyl)-10,11-dihydro-8H-[1, 4]oxazino[4',3':1,2]imidazo[4,5-c]quinolin-6-amine (300 mg, 1.0 mmol) dissolved in 5 mL of DMF. The reaction was heated to 80° C. and maintained at this temperature for 1 hour. The reaction mixture was cooled to ambient temperature and treated with 25 mL of H₂O. The resulting solid was isolated by filtration to give 150 mg of (11R)-11-[(methylthio)methyl]-10,11-dihydro-8H-[1,4]oxazino[4',3':1,2]imidazo[4,5-c]quinolin-6-amine as a white solid. The remaining filtrate was then extracted with CHCl₃ and the organic layer was dried over Na₂SO₄, filtered and then concentrated under reduced pressure to give a yellow oil. The oil was purified by chromatography (SiO₂, 0-30% CMA/CHCl₃) and the isolated material was slurried in acetonitrile and filtered to provide an additional 100 mg of desired product as a white solid, mp 105-108° C.

¹H NMR (300 MHz, DMSO-d₆) δ 7.92 (d, J=8.3 Hz, 1H), 7.63 (dd, J=1.1 and 8.4 Hz, 1H), 7.45 (ddd, J=1.2, 6.8 and 8.3 Hz, 1H), 7.28 (ddd, J=1.2, 7.0, and 8.4 Hz, 1H), 6.59 (s, 2H), 5.13-5.19 (m, 1H), 5.09 (d, J=16 Hz, 1H), 5.00 (d, J=16 Hz, 1H), 4.48 (d, J=13 Hz, 1H), 4.12 (bd, J=13 Hz, 1H), 2.93-3.0 (m, 2H); ¹³C NMR (125 MHz, DMSO-d₆) δ 151.8, 145.0, 144.6, 131.1, 126.6, 126.3, 126.2 121.0, 120.0, 114.3, 64.7, 64.5, 53.3, 34.6, 15.5; MS (APCI) m/z 301 (M+H)⁺. Anal. calcd for C₁₅H₁₆N₄OS: C, 59.98; H, 5.37; N, 18.65. Found: C, 59.69; H, 5.28; N, 18.88.

Example 84

(11R)-11-[(methylsulfonyl)methyl]-10,11-dihydro-8H-[1,4]oxazino[4',3':1,2]imidazo[4,5-c]quinolin-6-amine

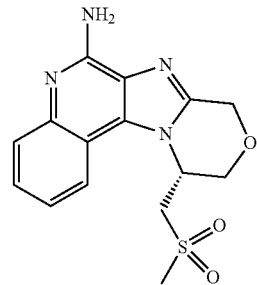 [SMILES: CS(=O)(=O)C[C@H]1COCc2nc3c(N)nc4ccccc4c3n21]

A solution of (11R)-11-[(methylthio)methyl]-10,11-dihydro-8H-[1,4]oxazino[4',3':1,2]imidazo[4,5-c]quinolin-6-amine (640 mg, 2.1 mmol) dissolved in 10 mL of CHCl₃ was cooled to 0° C. and treated with MCPBA (50% purity, 1.2 g, 4.3 mmol). The reaction mixture was warmed to ambient temperature over 1 hour. The resulting light brown reaction mixture was treated with 2 N aqueous Na₂CO₃ solution, diluted with water, and extracted with CHCl₃. The organic layer was dried over Na₂SO₄, filtered and then concentrated under reduced pressure to give a brown oil. Chromatography (SiO₂, 0-30% CMA/CHCl₃) gave the desired product as an oil. The oil was slurried in acetonitrile to produce a solid which was isolated by filtration to give 250 mg of the title compound as a white solid, mp 158-161° C.

¹H NMR (300 MHz, DMSO-d₆) δ 8.17 (d, J=8.3 Hz, 1H), 7.64 (d, J=8.4 Hz, 1H), 7.45 (ddd, J=1.4, 7.0 and 8.4 Hz, 1H), 7.24 (ddd, J=1.2, 7.0, 8.1 Hz, 1H), 6.60 (s, 2H), 5.59 (br d, J=11.2 Hz, 1H), 5.13 (d, J=16.0 Hz, 1H), 5.02 (d, J=16.0 Hz, 1H), 4.59 (d, J=12.3 Hz, 1H), 4.19 (br d, J=12.5 Hz, 1H), 4.00 (dd, J=11.2, 14.0 Hz, 1H), 3.68 (dd, J=13.9 Hz, 1H); ¹³C NMR (125 MHz, DMSO-d₆) δ 152.1, 145.4, 145.2, 131.3, 127.2, 126.8, 126.5, 121.7, 120.9, 114.8, 66.1, 65.2, 53.3, 49.2, 42.6; MS (APCI) m/z 333 (M+H)⁺. Anal. calcd for $C_{15}H_{16}N_4O_3S \cdot 0.5H_2O$: C, 52.77; H, 5.02; N, 16.41. Found: C, 52.54; H, 4.85; N, 16.41.

Example 85

(11R)-11-(Phenoxymethyl)-10,11-dihydro-8H-[1,4]oxazino[4',3':1,2]imidazo[4,5-c]quinolin-6-amine

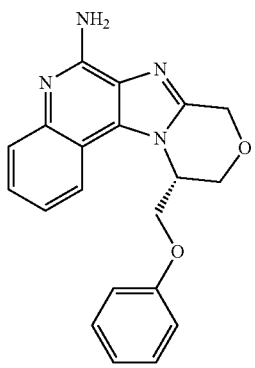 [SMILES: Nc1nc2ccccc2c2c1nc1n2[C@@H](COc2ccccc2)COC1]

[(11S)-6-Amino-10,11-dihydro-8H-[1,4]oxazino[4',3':1,2]imidazo[4,5-c]quinolin-11-yl]methanol (358 mg, 1.32 mmol) was suspended in 10 mL of dry THF and cooled to 0° C. under N₂. Triphenylphosphine (383 mg, 1.46 mmol) and phenol (137 mg, 1.46 mmol) were then added and the white slurry was stirred for 20 minutes. Diisopropyl azodicarboxylate (DIAD, 287 μL, 1.46 mmol) was then slowly added. After 1.5 hours, the reaction was allowed to warm to ambient temperature and stirring was continued overnight. The reaction mixture was then concentrated under reduced pressure and purified by column chromatography (SiO₂, EtOAc then 10-30% CMA/CHCl₃) to give a white solid. A second column chromatography (SiO₂, 0-20% CMA/CHCl₃) gave the product as a glassy solid. The solid was stirred in Et₂O and filtered to give 62 mg of the title compound as a white powder, mp 189-195° C.

¹H NMR (500 MHz, CDCl₃) δ 7.94 (d, J=8.2 Hz, 1H), 7.84 (d, J=8.4 Hz, 1H), 7.53 (m, 1H), 7.29 (m, 3H), 7.00 (m, 1H), 6.91 (d, J=8.6 Hz, 2H), 5.37 (s, 2H), 5.22 (d, J=15.8 Hz, 1H), 5.12 (m, 1H), 5.02 (d, J=15.8 Hz, 1H), 4.68 (d, J=12.3 Hz, 1H), 4.44 (m, 2H), 4.13 (dd, J=12.3, 2.7 Hz, 1H); MS (ESI) 347 m/z (M+H)⁺.

Exemplary Compounds

Certain exemplary compounds, including some of those described above in the Examples, have the following Formulas (IIIb, IVb, Vb, VIb, or VIIb,) and the following $X_1$ and $R_{1b}$ substituents, wherein each line of the table is matched with Formula IIIb, IVb, Vb, VIb, or VIIb to represent a specific embodiment of the invention.

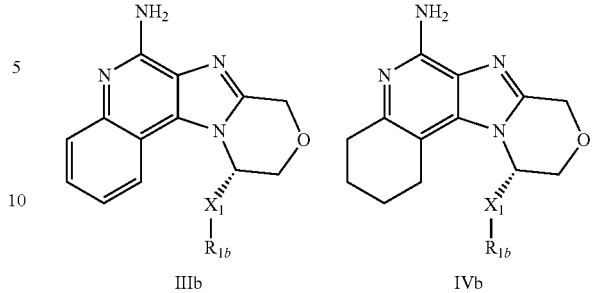

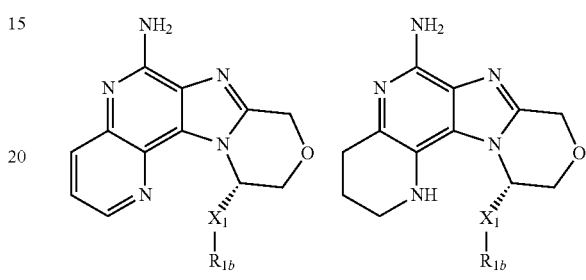

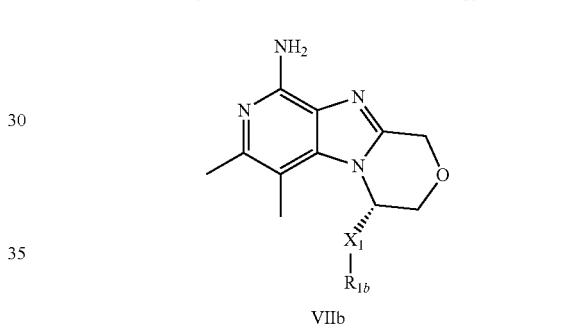

| $X_1$ | $R_{1b}$ |
|---|---|
| —CH₂— | —NH—S(O)₂—CH₃ |
| —CH₂— | ![morpholine-carbamate-NHMe] |
| —CH₂— | —NH—C(O)—CH(CH₃)₂ |
| —CH₂— | —NH—C(O)—CH₃ |
| —CH₂— | ![cyclopropyl-C(O)-NH-Me] |
| —CH₂— | ![phenyl-C(O)-NH-Me] |

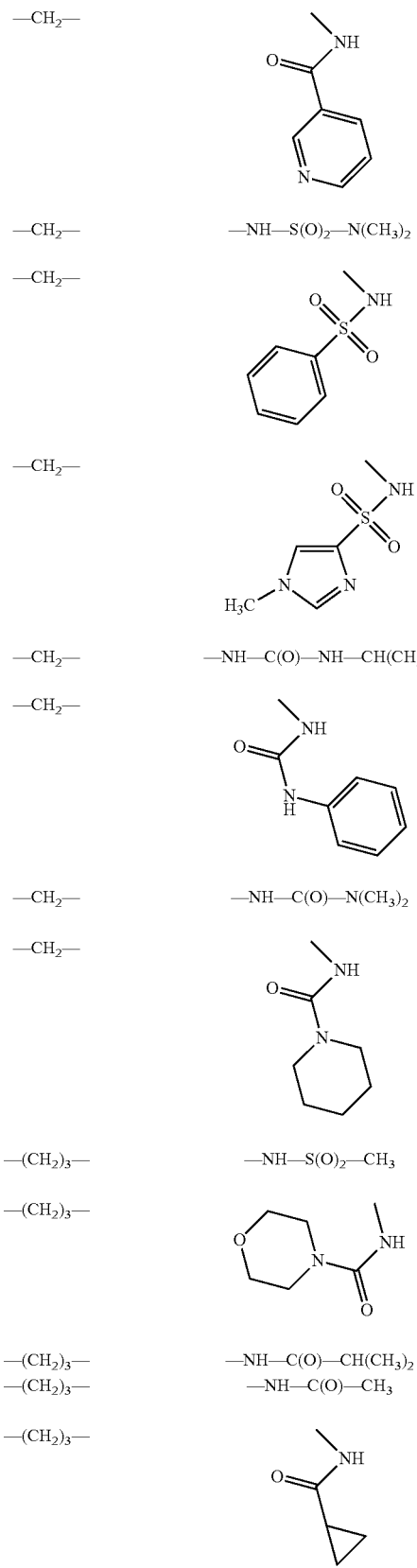
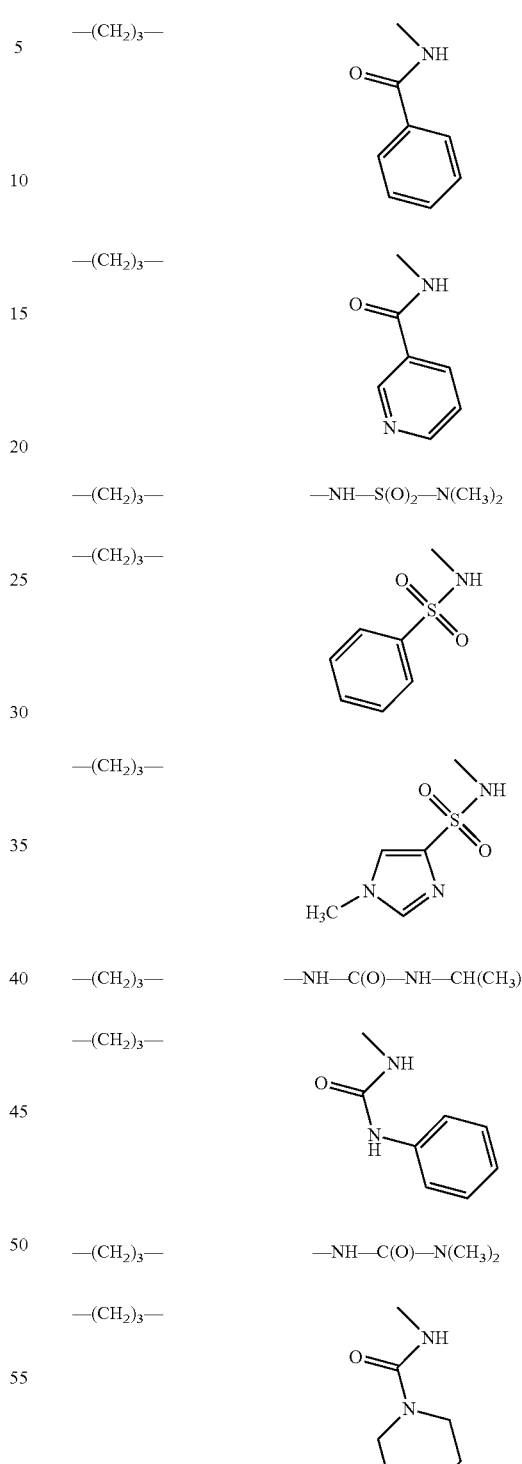
Certain exemplary compounds, including some of those described above in the Examples, have the following Formulas (IIIb, IVb, Vb, VIb, or VIIb,) and the following $X_1$ and $R_{1b}$ substituents, wherein each line of the table is matched with Formula IIIb, IVb, Vb, VIb, or VIIb to represent a specific embodiment of the invention.

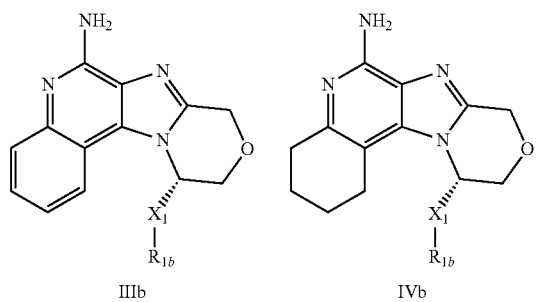
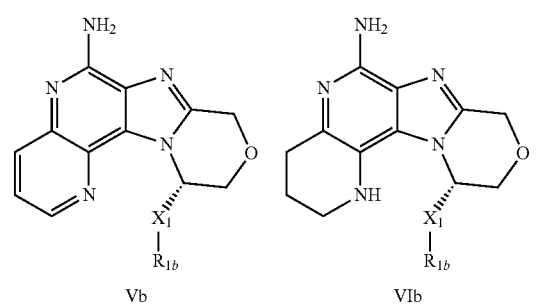
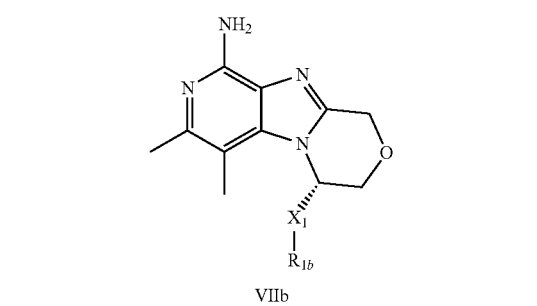

| $X_1$ | $R_{1b}$ |
|---|---|
| —(CH$_2$)$_2$— | —NH—S(O)$_2$—CH$_3$ |
| —(CH$_2$)$_2$— | 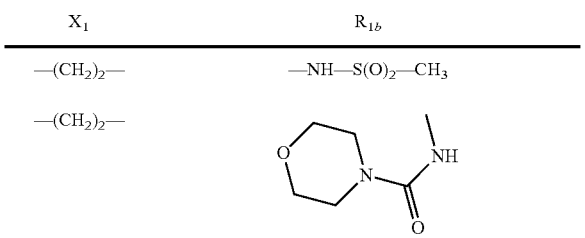 |
| —(CH$_2$)$_2$— | —NH—C(O)—CH(CH$_3$)$_2$ |
| —(CH$_2$)$_2$— | —NH—C(O)—CH$_3$ |
| —(CH$_2$)$_2$— | 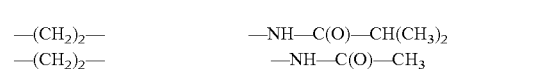 |
| —(CH$_2$)$_2$— |  |
| —(CH$_2$)$_2$— | 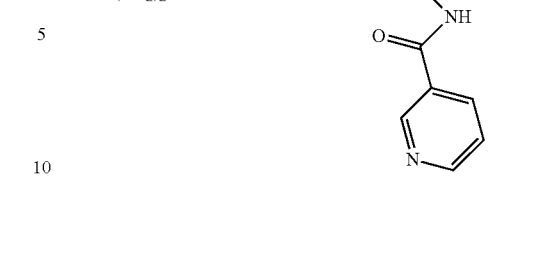 |
| —(CH$_2$)$_2$— | —NH—S(O)$_2$—N(CH$_3$)$_2$ |
| —(CH$_2$)$_2$— | 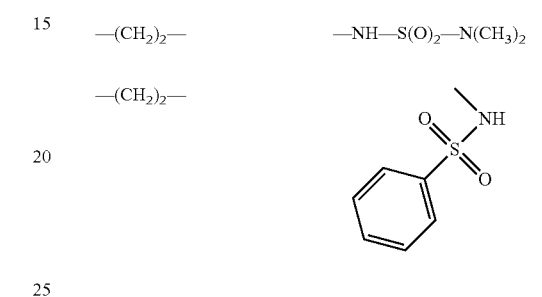 |
| —(CH$_2$)$_2$— | 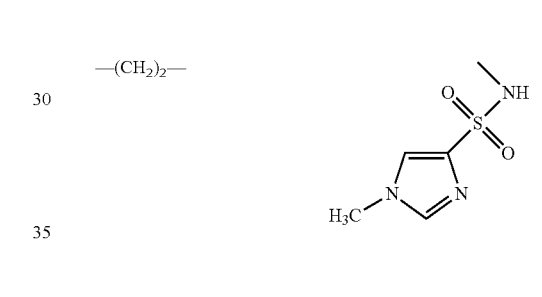 |
| —(CH$_2$)$_2$— | —NH—C(O)—NH—CH(CH$_3$)$_2$ |
| —(CH$_2$)$_2$— | 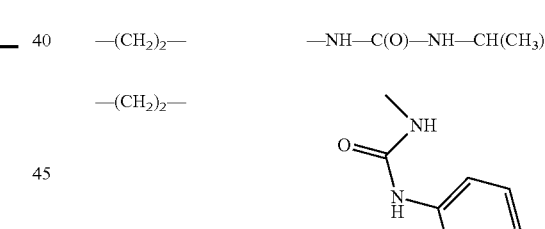 |
| —(CH$_2$)$_2$— | —NH—C(O)—N(CH$_3$)$_2$ |
| —(CH$_2$)$_2$— |  |

Certain exemplary compounds, including some of those described above in the Examples, have the following Formulas (IIIc, IVc, or Vc) and the following $X_1$ and $R_{1b}$ substituents, wherein each line of the table is matched with Formula IIIc, IVc, or Vc to represent a specific embodiment of the invention.

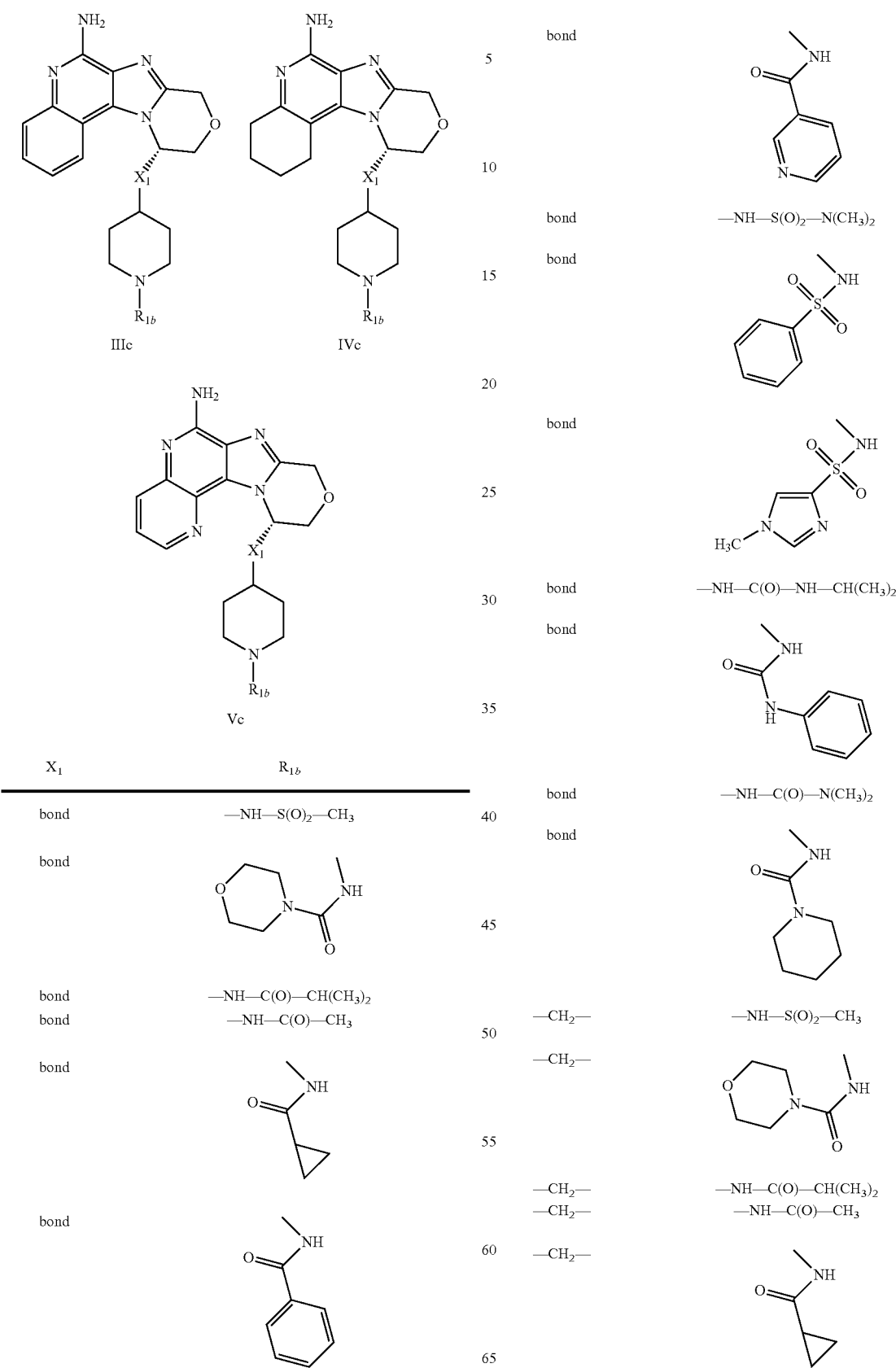

| | |
|---|---|
| —CH₂— | 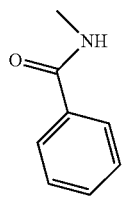 |
| —CH₂— | 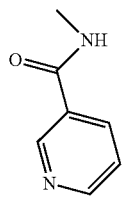 |
| —CH₂— | —NH—S(O)₂—N(CH₃)₂ |
| —CH₂— | 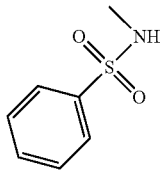 |
| —CH₂— | 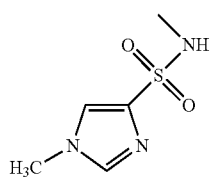 |
| —CH₂— | —NH—C(O)—NH—CH(CH₃)₂ |
| —CH₂— | 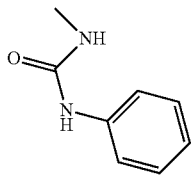 |
| —CH₂— | —NH—C(O)—N(CH₃)₂ |
| —CH₂— | 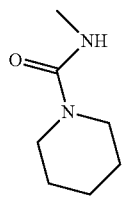 |

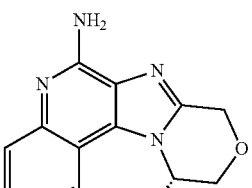

IIId      IVd

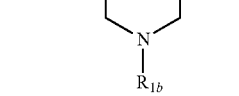

Vd

| $X_1$ | $R_{1b}$ |
|---|---|
| —CH₂— | —NH—S(O)₂—CH₃ |
| —CH₂— | 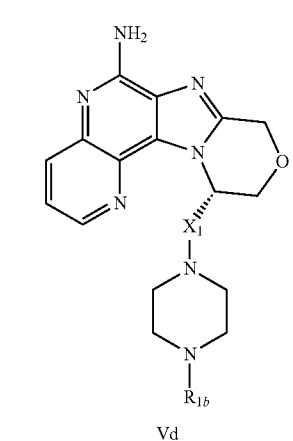 |
| —CH₂— | —NH—C(O)—CH(CH₃)₂ |
| —CH₂— | —NH—C(O)—CH₃ |
| —CH₂— | 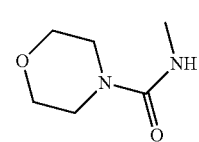 |
| —CH₂— | 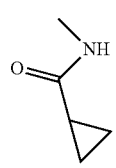 |
| | 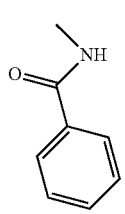 |

Certain exemplary compounds, including some of those described above in the Examples, have the following Formulas (IIId, IVd, or Vd) and the following $X_1$ and $R_{1b}$ substituents, wherein each line of the table is matched with Formula IIId, IVd, or Vd to represent a specific embodiment of the invention.

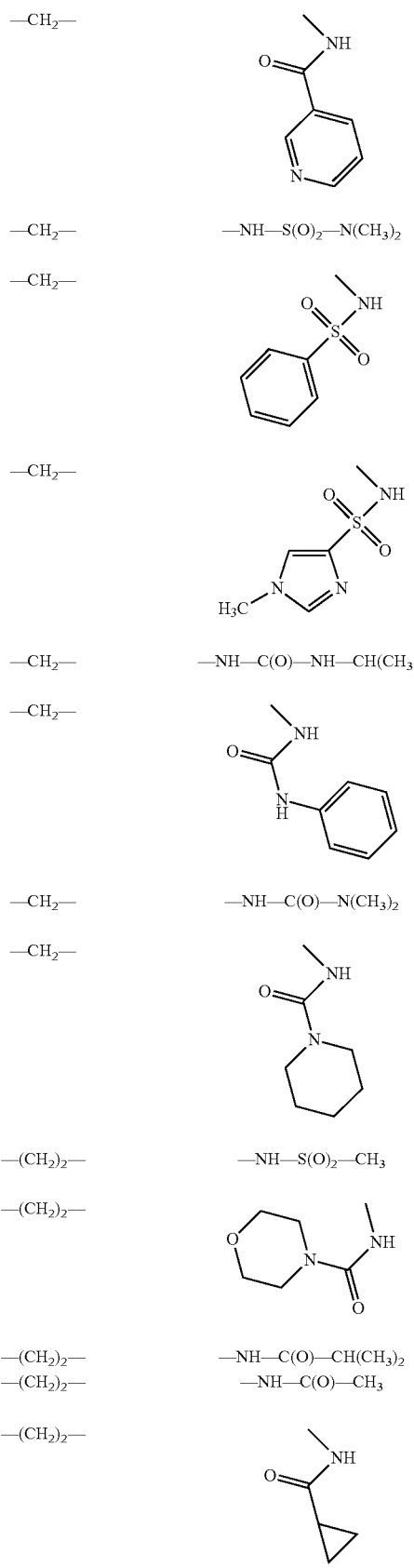
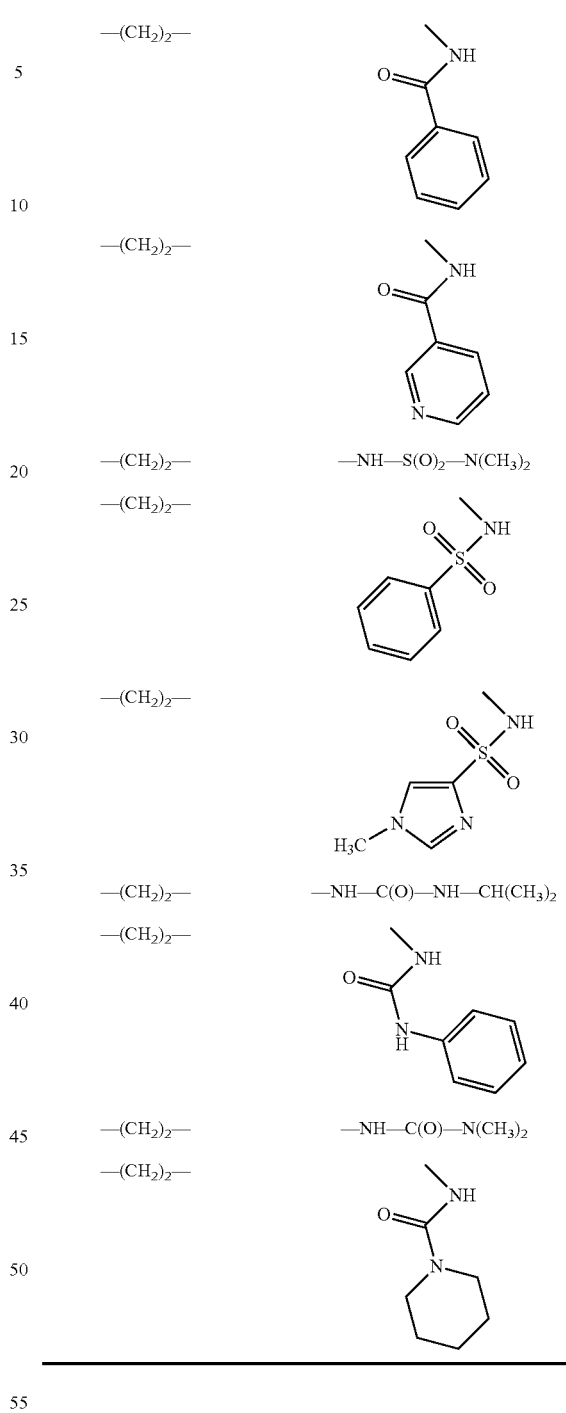

CYTOKINE INDUCTION IN HUMAN CELLS

Compounds of the invention, particularly compounds or salts of the Formulas II, IIa, III, IV, V, VI, and VII wherein Z is —O—, have been found to induce cytokine biosynthesis when tested using the method described below.

An in vitro human blood cell system is used to assess cytokine induction. Activity is based on the measurement of interferon (α) and tumor necrosis factor (α) (IFN-α and TNF-α, respectively) secreted into culture media as described by Testerman et al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM. Controls include cell samples with media only, cell samples with DMSO only (no compound), and cell samples with reference compound.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (usually 30-0.014 µM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (molar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

CYTOKINE INDUCTION IN HUMAN CELLS

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 µM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 µM) than the final tested concentration range.

Incubation

Compound solution is then added to the wells containing the PBMC suspension bringing the test compound concentrations to the desired range (usually 30-0.014 µM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (molar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Certain compounds of the invention, particularly compounds or salts of Formulas II-1, II-1a, III-1, IV-1, V-1, VI-1, and VII-1, or compounds or salts of Formulas II, IIa, III, IV, V, VI, and VII wherein Z is —N(—Y—$R_2$)—, may modulate cytokine biosynthesis by inhibiting production of tumor necrosis factor α (TNF-α) when tested using the method described below.

TNF-α INHIBITION IN MOUSE CELLS

The mouse macrophage cell line Raw 264.7 is used to assess the ability of compounds to inhibit tumor necrosis factor-α (TNF-α) production upon stimulation by lipopolysaccharide (LPS).

Single Concentration Assay:

Blood Cell Preparation for Culture

Raw cells (ATCC) are harvested by gentle scraping and then counted. The cell suspension is brought to $3 \times 10^5$ cells/mL in RPMI with 10% fetal bovine serum (FBS). Cell suspension (100 µL) is added to 96-well flat bottom sterile tissues culture plates (Becton Dickinson Labware, Lincoln Park, N.J.). The final concentration of cells is $3 \times 10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 µM. LPS (Lipopolysaccharide from *Salmonella typhimurium*, Sigma-Aldrich) is diluted with colorless RPMI to the $EC_{70}$ concentration as measured by a dose response assay.

Incubation

A solution of test compound (1 µl) is added to each well. The plates are mixed on a microtiter plate shaker for 1 minute and then placed in an incubator. Twenty minutes later the solution of LPS (1 µL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:

Blood Cell Preparation for Culture

Raw cells (ATCC) are harvested by gentle scraping and then counted. The cell suspension is brought to $4 \times 10^5$ cells/mL in RPMI with 10% FBS. Cell suspension (250 µL) is added to 48-well flat bottom sterile tissues culture plates (Costar, Cambridge, Mass.). The final concentration of cells is $1 \times 10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 µM. LPS (Lipopolysaccaride from *Salmonella typhimurium*, Sigma-Aldrich) is diluted with colorless RPMI to the $EC_{70}$ concentration as measured by dose response assay.

Incubation

A solution of test compound (200 μL) is added to each well. The plates are mixed on a microtiter plate shaker for 1 minute and then placed in an incubator. Twenty minutes later the solution of LPS (200 μL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound selected from the group consisting of:
   N-{[(11S)-6-amino-10,11-dihydro-8H-[1,4]oxazino[4',3': 1,2]imidazo[4,5-c]quinolin-11-yl] methyl}methanesulfonamide;
   N-{3-[(11S)-6-amino-10,11-dihydro-8H-[1,4]oxazino[4', 3':1,2]imidazo[4,5-c]quinolin-11-yl] propyl}methanesulfonamide;
   N-{3-[(11S)-6-amino-10,11-dihydro-8H-[1,4]oxazino[4', 3':1,2]imidazo[4,5-c]quinolin-11-yl] propyl}morpholine-4-carboxamide;
   N-{3-[(11S)-6-amino-10,11-dihydro-8H-[1,4]oxazino[4', 3':1,2]imidazo[4,5-c]quinolin-11-yl]propyl}-2-methyl-propanamide;
   N-{3-[(11S)-6-amino-10,11-dihydro-8H-[1,4]oxazino[4', 3':1,2]imidazo[4,5-c]quinolin-11-yl]propyl}acetamide;
   N-{3-[(11S)-6-amino-10,11-dihydro-8H-[1,4]oxazino[4', 3':1,2]imidazo[4,5-c]quinolin-11-yl] propyl}cyclopropanecarboxamide;
   N-{3-[(11S)-6-amino-10,11-dihydro-8H-[1,4]oxazino[4', 3':1,2]imidazo[4,5-c]quinolin-11-yl] propyl}benzamide;
   N-{3-[(11S)-6-amino-10,11-dihydro-8H-[1,4]oxazino[4', 3':1,2]imidazo[4,5-c]quinolin-11-yl] propyl}nicotinamide;
   N'-{3-[(11S)-6-amino-10,11-dihydro-8H-[1,4]oxazino [4',3':1,2]imidazo[4,5-c]quinolin-11-yl]propyl}-N,N-dimethylsulfamide;
   N-{3-[(11S)-6-amino-10,11-dihydro-8H-[1,4]oxazino[4', 3':1,2]imidazo[4,5-c]quinolin-11-yl] propyl}benzenesulfonamide;
   N-{3-[(11S)-6-amino-10,11-dihydro-8H-[1,4]oxazino[4', 3':1,2]imidazo[4,5-c]quinolin-11-yl]propyl}-1-methyl-imidazole-4-sulfonamide;
   N'-{3-[(11S)-6-amino-10,11-dihydro-8H-[1,4]oxazino [4',3':1,2]imidazo[4,5-c]quinolin-11-yl]propyl}-N-(1-methylethyl)urea;
   N'-{3-[(11S)-6-amino-10,11-dihydro-8H-[1,4]oxazino [4',3':1,2]imidazo[4,5-c]quinolin-11-yl]propyl}-N-phenylurea;
   N'-{3-[(11S)-6-amino-10,11-dihydro-8H-[1,4]oxazino [4',3':1,2]imidazo[4,5-c]quinolin-11-yl]propyl}-N,N-dimethylurea;
   N-{3-[(11S)-6-amino-10,11-dihydro-8H-[1,4]oxazino[4', 3':1,2]imidazo[4,5-c]quinolin-11-yl] propyl}piperidine-1-carboxamide;
   (11R)-11-[(methylthio)methyl]-10,11-dihydro-8H-[1,4] oxazino[4',3':1,2]imidazo[4,5-c]quinolin-6-amine; and
   (11R)-11-[(methylsulfonyl)methyl]-10,11-dihydro-8H-[1,4]oxazino[4',3':1,2]imidazo[4,5-c]quinolin-6-amine;
   or a pharmaceutically acceptable salt thereof.

2. The compound of claim 1, selected from the group consisting of:
   N-{[(11S)-6-amino-10,11-dihydro-8H-[1,4]oxazino[4',3': 1,2]imidazo[4,5-c]quinolin-11-yl] methyl}methanesulfonamide;
   N-{3-[(11S)-6-amino-10,11-dihydro-8H-[1,4]oxazino[4', 3':1,2]imidazo[4,5-c]quinolin-11-yl] propyl}methanesulfonamide;
   N-{3-[(11S)-6-amino-10,11-dihydro-8H-[1,4]oxazino[4', 3':1,2]imidazo[4,5-c]quinolin-11-yl] propyl}morpholine-4-carboxamide;
   N-{3-[(11S)-6-amino-10,11-dihydro-8H-[1,4]oxazino[4', 3':1,2]imidazo[4,5-c]quinolin-11-yl]propyl}-2-methyl-propanamide;
   (11R)-11-[(methylthio)methyl]-10,11-dihydro-8H-[1,4] oxazino[4',3':1,2]imidazo[4,5-c]quinolin-6-amine; and
   (11R)-11-[(methylsulfonyl)methyl]-10,11-dihydro-8H-[1,4]oxazino[4',3':1,2]imidazo[4,5-c]quinolin-6-amine;
   or a pharmaceutically acceptable salt thereof.

3. The compound of claim 2, selected from the group consisting of:
   N-{[(11S)-6-amino-10,11-dihydro-8H-[1,4]oxazino[4',3': 1,2]imidazo[4,5-c]quinolin-11-yl] methyl}methanesulfonamide; and
   N-{3-[(11S)-6-amino-10,11-dihydro-8H-[1,4]oxazino[4', 3':1,2]imidazo[4,5-c]quinolin-11-yl] propyl}methanesulfonamide;
   or a pharmaceutically acceptable salt thereof.

4. The compound of claim 3, wherein the compound is N-{3-[(11S)-6-amino-10,11-dihydro-8H-[1,4]oxazino[4',3': 1,2]imidazo[4,5-c]quinolin-11-yl] propyl}methanesulfonamide or a pharmaceutically acceptable salt thereof.

5. A pharmaceutical composition comprising a therapeutically effective amount of a compound or salt of claim 2 and a pharmaceutically acceptable carrier.

6. A method of inducing cytokine biosynthesis in an animal comprising administering an effective amount of a compound or salt of claim 2 to the animal.

7. The compound of claim 1, selected from the group consisting of:
   N-{3-[(11S)-6-amino-10,11-dihydro-8H-[1,4]oxazino[4', 3':1,2]imidazo[4,5-c]quinolin-11-yl]propyl}-2-methyl-propanamide;
   N-{3-[(11S)-6-amino-10,11-dihydro-8H-[1,4]oxazino[4', 3':1,2]imidazo[4,5-c]quinolin-11-yl]propyl}acetamide;
   N-{3-[(11S)-6-amino-10,11-dihydro-8H-[1,4]oxazino[4', 3':1,2]imidazo[4,5-c]quinolin-11-yl] propyl}cyclopropanecarboxamide;
   N-{3-[(11S)-6-amino-10,11-dihydro-8H-[1,4]oxazino[4', 3':1,2]imidazo[4,5-c]quinolin-11-yl] propyl}benzamide; and
   N-{3-[(11S)-6-amino-10,11-dihydro-8H-[1,4]oxazino[4', 3':1,2]imidazo[4,5-c]quinolin-11-yl] propyl}nicotinamide;
   or a pharmaceutically acceptable salt thereof.

8. The compound of claim 1, selected from the group consisting of:
   N-{3-[(11S)-6-amino-10,11-dihydro-8H-[1,4]oxazino[4', 3':1,2]imidazo[4,5-c]quinolin-11-yl] propyl}morpholine-4-carboxamide;
   N'-{3-[(11S)-6-amino-10,11-dihydro-8H-[1,4]oxazino [4',3':1,2]imidazo[4,5-c]quinolin-11-yl]propyl}-N-(1-methylethyl)urea;

N'-{3-[(11S)-6-amino-10,11-dihydro-8H-[1,4]oxazino[4',3':1,2]imidazo[4,5-c]quinolin-11-yl]propyl}-N-phenylurea;

N'-{3-[(11S)-6-amino-10,11-dihydro-8H-[1,4]oxazino[4',3':1,2]imidazo[4,5-c]quinolin-11-yl]propyl}-N,N-dimethylurea; and N-{3-[(11S)-6-amino-10,11-dihydro-8H-[1,4]oxazino[4',3':1,2]imidazo[4,5-c]quinolin-11-yl]propyl}piperidine-1-carboxamide;

or a pharmaceutically acceptable salt thereof.

9. The compound of claim 1, selected from the group consisting of:

N'-{3-[(11S)-6-amino-10,11-dihydro-8H-[1,4]oxazino[4',3':1,2]imidazo[4,5-c]quinolin-11-yl]propyl}-N,N-dimethylsulfamide;

N-{3-[(11S)-6-amino-10,11-dihydro-8H-[1,4]oxazino[4',3':1,2]imidazo[4,5-c]quinolin-11-yl]propyl}benzenesulfonamide;

(11R)-11-[(methylthio)methyl]-10,11-dihydro-8H-[1,4]oxazino[4',3':1,2]imidazo[4,5-c]quinolin-6-amine; and (11R)-11-[(methylsulfonyl)methyl]-10,11-dihydro-8H-[1,4]oxazino[4',3':1,2]imidazo[4,5-c]quinolin-6-amine;

or a pharmaceutically acceptable salt thereof.

10. A pharmaceutical composition comprising a therapeutically effective amount of a compound or salt of claim 1 and a pharmaceutically acceptable carrier.

11. A method of inducing cytokine biosynthesis in an animal comprising administering an effective amount of a compound or salt of claim 1 to the animal.

12. A compound selected from the group consisting of:

N-{3-[(11S)-6-amino-2,3,4,8,10,11-hexahydro-1H-[1,4]oxazino[4',3':1,2]imidazo[4,5-c]quinolin-11-yl]propyl}methanesulfonamide;

N-{3-[(11S)-6-amino-2,3,4,8,10,11-hexahydro-1H-[1,4]oxazino[4',3':1,2]imidazo[4,5-c]quinolin-11-yl]propyl}morpholine-4-carboxamide;

N-{3-[(11S)-6-amino-2,3,4,8,10,11-hexahydro-1H-[1,4]oxazino[4',3':1,2]imidazo[4,5-c]quinolin-11-yl]propyl}acetamide;

N-{3-[(11S)-6-amino-2,3,4,8,10,11-hexahydro-1H-[1,4]oxazino[4',3':1,2]imidazo[4,5-c]quinolin-11-yl]propyl}cyclopropanecarbocamide;

N'-{3-[(11S)-6-amino-2,3,4,8,10,11-hexahydro-1H-[1,4]oxazino[4',3':1,2]imidazo[4,5-c]quinolin-11-yl]propyl}-N,N-dimethylsulfamide;

N-{3-[(11S)-6-amino-2,3,4,8,10,11-hexahydro-1H-[1,4]oxazino[4',3':1,2]imidazo[4,5-c]quinolin-11-yl]propyl}benzenesulfonamide;

N-{3-[(11S)-6-amino-2,3,4,8,10,11-hexahydro-1H-[1,4]oxazino[4',3':1,2]imidazo[4,5-c]quinolin-11-yl]propyl}-1-methyl-imidazole-4-sulfonamide;

N'-{3-[(11S)-6-amino-2,3,4,8,10,11-hexahydro-1H-[1,4]oxazino[4',3':1,2]imidazo[4,5-c]quinolin-11-yl]propyl}-N-(1-methylethyl)urea;

N'-{3-[(11S)-6-amino-2,3,4,8,10,11-hexahydro-1H-[1,4]oxazino[4',3':1,2]imidazo[4,5-c]quinolin-11-yl]propyl}phenylurea;

N'-{3-[(11S)-6-amino-2,3,4,8,10,11-hexahydro-1H-[1,4]oxazino[4',3':1,2]imidazo[4,5-c]quinolin-11-yl]propyl}-N,N-dimethylurea; and N-{3-[(11S)-6-amino-2,3,4,8,10,11-hexahydro-1H-[1,4]oxazino[4',3':1,2]imidazo[4,5-c]quinolin-11-yl]propyl}piperidine-1-carboxamide;

or a pharmaceutically acceptable salt thereof.

13. The compound of claim 12, selected from the group consisting of:

N-{3-[(11S)-6-amino-2,3,4,8,10,11-hexahydro-1H-[1,4]oxazino[4',3':1,2]imidazo[4,5-c]quinolin-11-yl]propyl}methanesulfonamide; and N-{3-[(11S)-6-amino-2,3,4,8,10,11-hexahydro-1H-[1,4]oxazino[4',3':1,2]imidazo[4,5-c]quinolin-11-yl]propyl}morpholine-4-carboxamide;

or a pharmaceutically acceptable salt thereof.

14. A pharmaceutical composition comprising a therapeutically effective amount of a compound or salt of claim 12 and a pharmaceutically acceptable carrier.

15. A method of inducing cytokine biosynthesis in an animal comprising administering an effective amount of a compound or salt of claim 12 to the animal.

* * * * *